(12) United States Patent
Moffat et al.

(10) Patent No.: US 8,044,211 B2
(45) Date of Patent: Oct. 25, 2011

(54) P38 MAP KINASE INHIBITORS

(75) Inventors: David Charles Festus Moffat, Abingdon (GB); Stephane Pintat, Abingdon (GB); Stephen Davies, Abingdon (GB)

(73) Assignee: Chroma Therapeutics Ltd. (GB)

( * ) Notice: Subject to any disclaimer, the term of this patent is extended or adjusted under 35 U.S.C. 154(b) by 462 days.

(21) Appl. No.: 12/299,333

(22) PCT Filed: May 1, 2007

(86) PCT No.: PCT/GB2007/001596
§ 371 (c)(1),
(2), (4) Date: Nov. 3, 2008

(87) PCT Pub. No.: WO2007/129040
PCT Pub. Date: Nov. 15, 2007

(65) Prior Publication Data
US 2009/0099185 A1    Apr. 16, 2009

(30) Foreign Application Priority Data

May 4, 2006  (GB) .................................. 0608855.3
Jul. 13, 2006  (GB) .................................. 0613914.1

(51) Int. Cl.
*C07D 213/72* (2006.01)
*C07D 239/02* (2006.01)
*A61K 31/505* (2006.01)
*A61K 31/44* (2006.01)

(52) U.S. Cl. ......... 546/297; 544/301; 514/274; 514/349

(58) Field of Classification Search ........................ None
See application file for complete search history.

(56) References Cited

FOREIGN PATENT DOCUMENTS

WO    03/076405 A    9/2003

*Primary Examiner* — Janet Andres
*Assistant Examiner* — Heidi Reese
(74) *Attorney, Agent, or Firm* — Banner & Witcoff, Ltd.

(57) ABSTRACT

Compounds of formula (I) are inhibitors of p38 MAP kinase, and are therefore of utility in the treatment of, inter alia, inflammatory conditions including rheumatoid arthritis and COPD:

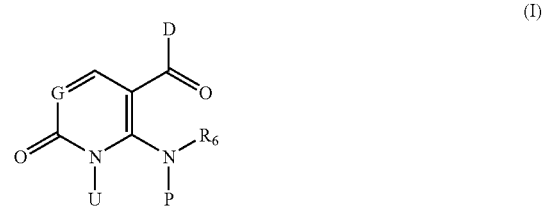

(I)

wherein: G is —N= or —CH=; D is an optionally substituted divalent mono- or bi-cyclic aryl or heteroaryl radical having 5-13 ring members; $R_6$ is hydrogen or optionally substituted $C_1$-$C_3$ alkyl; P represents hydrogen and U represents a radical of formula (IA); or U represents hydrogen and P represents a radical of formula -A-$(CH_2)_z$—$X^1$-$L^1$-Y—NH—$CHR_1R_2$ wherein A represents an optionally substituted divalent mono- or bicyclic carbocyclic or heterocyclic radical having 5-13 ring members; z, Y, $L^1$, and $X^1$ are as defined in the specification; $R_1$ is a carboxylic acid group (—COOH), or an ester group which is hydrolysable by one or more intracellular esterase enzymes to a carboxylic acid group; and $R_2$ is the side chain of a natural or non-natural alpha amino acid.

28 Claims, No Drawings

P38 MAP KINASE INHIBITORS

CROSS REFERENCE TO RELATED APPLICATIONS

This application is a National Stage application of co-pending PCT application PCT/GB2007/001596 filed May 1, 2007, which claims the benefit of Great Britain application number 0608855.3 filed May 4, 2006 and Great Britain application number 0613914.1 filed Jul. 13, 2006. These applications are incorporated herein by reference in their entireties.

This invention relates to a series of amino acid and amino acid ester compounds, to compositions containing them, to processes for their preparation and to their use in medicine as p38 MAP kinase inhibitors for the treatment of autoimmune and inflammatory diseases, including rheumatoid arthritis, psoriasis, inflammatory bowel disease, Crohns disease, ulcerative colitis, chronic obstructive pulmonary disease, asthma, multiple sclerosis, diabetes, atopic dermatitis, graft versus host disease, systemic lupus erythematosus and others.

BACKGROUND OF THE INVENTION

Inappropriate activation of leukocytes including monocytes, macrophages and neutrophils leading to the production of elevated levels cytokines such as TNF-α, IL1-β and IL-8, is a feature of the pathogenesis of several inflammatory diseases including rheumatoid arthritis, ulcerative colitis, Crohn's disease, chronic obstructive pulmonary disease (COPD), asthma and psoriasis. The production of cytokines by inflammatory cells is a result of response to a variety of external stimuli, leading to the activation of a number of intracellular signalling mechanisms. Prominent amongst these is the mitogen-activated protein kinase (MAPK) superfamily consisting of highly conserved signalling kinases that regulate cell growth, differentiation and stress responses. Mammalian cells contain at least three families of MAPKs: the p42/44 extracellular signal-regulated kinase (ERK) MAPKs, c-Jun $NH_2$-terminal kinases (JNKs) and p38 MAPK (also termed p38a/Mpk2/RK/SAPK2a/CSBP1/2). p38 MAPK was first cloned following its identification as a kinase that is tyrosine phosphorylated after stimulation of monocytes by lipopolysaccharide (LPS) [Han et al, Science 1994, 265, 808]. Additional homologues of mammalian p38 have been described and include p38β [Jiang et al, J. Biol. Chem., 1996, 271, 17920], p38γ [Li et al, Biochem. Biophys. Res. Commun., 1996, 228, 334] and p38δ [Jiang et al, J. Biol. Chem. 1997, 272, 30122]. While p38α and p38β are ubiquitously expressed, p38γ is restricted primarily to skeletal muscle and p38δ is predominantly expressed in lung and kidney.

The release of cytokines by host defense cells and the response of leukocytes to cytokines and other pro-inflammatory stresses are to varying extent regulated by p38 MAPK [Cuenda et al, FEBS Lett, 1995, 364, 229-233]. In other cell types, p38 MAPK controls stress responses such as the production of IL-8 by bronchial epithelial cells stimulated by TNF-α, and the up-regulation of the cell adhesion molecule ICAM-1 in LPS-stimulated endothelial cells. Upon activation, via dual phosphorylation of a TGY motif by the dual specificity kinases MKK3 and MKK6, p38 MAPK exerts its effects through phosphorylation of transcription factors and other kinases. MAP kinase-activated protein kinase-2 (MAP-KAPK-2) has been identified as a target for p38 phosphorylation. It has been demonstrated that mice [Kotlyarov et al, Nat. Cell Biol. 1999, 1, 94-97] lacking MAPKAP-K2 release reduced levels of TNF-α, IL-1β, IL-6, IL-10 and IFN-γ in response to LPS/galactosamine mediated endotoxic shock. The regulation of the levels of these cytokines as well as COX-2 is at the mRNA level. TNF-α levels are regulated through translational control via AU-rich elements of the 3'-UTR of TNF-α mRNA, with MAPKAP-K2 signalling increasing TNF-α mRNA translation. MAPKAP-K2 signalling leads to increased mRNA stability for COX-2, IL-6 and macrophage inflammatory protein. MAPKAP K2 determines the cellular location of p38 MAPK as well as transducing p38 MAPK signalling, possessing a nuclear localisation signal at its carboxyl terminus and a nuclear export signal as part of its autoinhibitory domain [Engel et al, EMBO J. 1998, 17, 3363-3371]. In stressed cells, MAPKAP-K2 and p38 MAPK migrate to the cytoplasm from the nucleus, this migration only occurring when p38 MAPK is catalytically active. It is believed that this event is driven by the exposure of the MAP-KAP-K2 nuclear export signal, as a result of phosphorylation by p38 MAPK [Meng et al, J. Biol. Chem. 2002, 277, 37401-37405]. Additionally p38 MAPK either directly or indirectly leads to the phosphorylation of several transcription factors believed to mediate inflammation, including ATF1/2 (activating transcription factors 1/2), CHOP-10/GADD-153 (growth arrest and DNA damage inducible gene 153), SAP-1 (serum response factor accessory protein-1) and MEF2C (myocyte enhancer factor-2) [Foster et al, Drug News Perspect. 2000, 13, 488-497].

It has been demonstrated in several instances that the inhibition of p38 MAPK activity by small molecules, is useful for the treatment of several disease states mediated by inappropriate cytokine production including rheumatoid arthritis, COPD, asthma and cerebral ischemia. This modality has been the subject of several reviews [Salituro et al, Current Medicinal Chemistry, 1999, 6, 807-823 and Kumar et al, Nature Reviews Drug Discovery 2003, 2, 717-726].

Inhibitors of p38 MAPK have been shown to be efficacious in animal models of rheumatoid arthritis, such as collagen-induced arthritis in rat [Revesz et al, Biorg. Med. Chem. Lett., 2000, 10, 1261-1364] and adjuvant-induced arthritis in rat [Wadsworth et al, J. Pharmacol. Exp. Ther., 1999, 291, 1685-1691]. In murine models of pancreatitis-induced lung injury, pretreatment with a p38 MAPK inhibitor reduced TNF-α release in the airways and pulmonary edema [Denham et al, Crit. Care Med., 2000, 29, 628 and Yang et al, Surgery, 1999, 126, 216]. Inhibition of p38 MAPK before ovalbumin (OVA) challenge in OVA-sensitized mice decreased cytokine and inflammatory cell accumulation in the airways in an allergic airway model of inflammation, [Underwood et al, J. Pharmacol. Exp. Ther., 2000, 293, 281]. Increased activity of p38 MAP kinase has been observed in patients suffering from inflammatory bowel disease [Waetzig et al, J. Immunol, 2002, 168, 5432-5351]. p38 MAPK inhibitors have been shown to be efficacious in rat models of cardiac hypertrophy [Behr et al, Circulation, 2001, 104, 1292-1298] and cerebral focal ischemia [Barone et al, J. Pharmacol. Exp. Ther., 2001, 296, 312-321].

We have now discovered a group of compounds which are potent and selective inhibitors of p38 MAPK (p38α,β,γ and δ) and the isoforms and splice variants thereof especially p38α, p38β and p38β2. The compounds are thus of use in medicine, for example in the treatment and prophylaxis of immune and inflammatory disorders described herein. The compounds are characterised by the presence in the molecule of an amino acid motif or an amino acid ester motif which is hydrolysable by an intracellular carboxylesterase. Compounds of the invention having the lipophilic amino acid ester motif cross the cell membrane, and are hydrolysed to the acid by the intracellular carboxylesterases. The polar hydrolysis product accumulates in the cell since it does not readily cross the cell membrane. Hence the p38 MAP kinase activity of the compound is prolonged and enhanced within the cell. The compounds of the invention are related to the p38 MAP kinase inhibitors encompassed by the disclosures in International Patent Application WO03076405 but differ therefrom in that the present compounds have the amino acid ester motif referred to above.

DETAILED DESCRIPTION OF THE INVENTION

According to the invention there is provided a compound of formula (I):

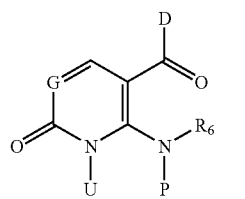

(I)

wherein:
G is —N= or —CH=
D is an optionally substituted divalent mono- or bicyclic aryl or heteroaryl radical having 5-13 ring members;
$R_6$ is hydrogen or optionally substituted $C_1$-$C_3$ alkyl;
P represents hydrogen and U represents a radical of formula (IA); or U represents hydrogen and P represents a radical of formula (IA);

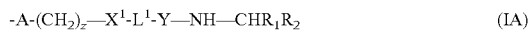

wherein
A represents an optionally substituted divalent mono- or bicyclic carbocyclic or heterocyclic radical having 5-13 ring members;
z is 0 or 1;
Y is a bond, —C(=O)—, —S(=O)$_2$—, —C(=O)NR$_3$—, —C(=S)—NR$_3$, —C(=NH)NR$_3$ or —S(=O)$_2$NR$_3$— wherein $R_3$ is hydrogen or optionally substituted $C_1$-$C_6$ alkyl;
$L^1$ is a divalent radical of formula -(Alk$^1$)$_m$(O)$_n$(Alk$^2$)$_p$— wherein
  m, n and p are independently 0 or 1,
  Q is (i) an optionally substituted divalent mono- or bicyclic carbocyclic or heterocyclic radical having 5-13 ring members, or (ii), in the case where both m and p are 0, a divalent radical of formula —X$^2$-Q$^1$- or -Q$^1$-X$^2$— wherein X$^2$ is —O—, S— or NR$^A$— wherein R$^A$ is hydrogen or optionally substituted $C_1$-$C_3$ alkyl, and Q$^1$ is an optionally substituted divalent mono- or bicyclic carbocyclic or heterocyclic radical having 5-13 ring members,
  Alk$^1$ and Alk$^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—), thioether (—S—) or amino (—NR$^A$—) link wherein R$^A$ is hydrogen or optionally substituted $C_1$-$C_3$ alkyl; and
X$^1$ represents a bond; —C(=O); or —S(=O)$_2$—; —NR$_4$C(=O)—, —C(=O)NR$_4$—, —NR$_4$C(=O)NR$_5$—, —NR$_4$S(=O)$_2$—, or —S(=O)$_2$NR$_4$— wherein $R_4$ and $R_5$ are independently hydrogen or optionally substituted $C_1$-$C_6$ alkyl.

$R_1$ is a carboxylic acid group (—COOH), or an ester group which is hydrolysable by one or more intracellular esterase enzymes to a carboxylic acid group; and
$R_2$ is the side chain of a natural or non-natural alpha amino acid.

Compounds of formula (I) above may be prepared in the form of salts, especially pharmaceutically acceptable salts, N-oxides, hydrates, and solvates thereof. Any claim to a compound herein, or reference herein to "compounds of the invention", "compounds with which the invention is concerned", "compounds of formula (I)" and the like, includes salts, N-oxides, hydrates, and solvates of such compounds.

Although the above definition potentially includes molecules of high molecular weight, it is preferable, in line with general principles of medicinal chemistry practice, that the compounds with which this invention is concerned should have molecular weights of no more than 600.

In another broad aspect the invention provides the use of a compound of formula (I) as defined above, or an N-oxide, salt, hydrate or solvate thereof in the preparation of a composition for inhibiting the activity p38 MAP kinase enzyme.

The compounds with which the invention is concerned may be used for the inhibition of p38 MAP kinase enzyme activity in vitro or in vivo.

In one aspect of the invention, the compounds of the invention may be used in the preparation of a composition for the treatment of autoimmune or inflammatory disease, particularly those mentioned above in which p38 MAP kinase activity plays a role.

In another aspect, the invention provides a method for the treatment of the foregoing disease types, which comprises administering to a subject suffering such disease an effective amount of a compound of formula (I) as defined above.

Terminology

The term "ester" or "esterified carboxyl group" means a group $R^xO(C=O)$— in which $R^x$ is the group characterising the ester, notionally derived from the alcohol $R^xOH$.

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences.

As used herein the term "($C_a$-$C_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent ($C_a$-$C_b$)alkenylene radical" means a hydrocarbon chain having from a to b carbon atoms, at least one double bond, and two unsatisfied valences.

As used herein the term "$C_a$-$C_b$ alkynyl" wherein a and b are integers refers to straight chain or branched chain hydrocarbon groups having from a to b carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_a$-$C_b$)alkynylene radical" wherein a and b are integers refers to a divalent hydrocarbon chain having from a to b carbon atoms, and at least one triple bond.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

A "divalent phenylene, pyridinylene, pyrimidinylene, or pyrazinylene radical" is a benzene, pyridine, pyrimidine or pyrazine ring, with two unsatisfied valencies, and includes 1,3-phenylene, 1,4-phenylene, and the following:

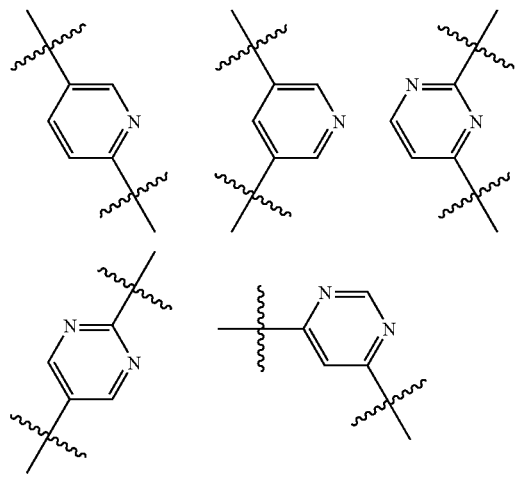

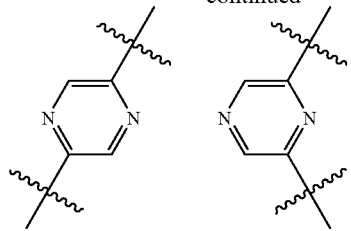

-continued

Unless otherwise specified in the context in which it occurs, the term "substituted" as applied to any moiety herein means substituted with up to four compatible substituents, each of which independently may be, for example, ($C_1$-$C_6$) alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, phenyl, halo (including fluoro, bromo and chloro), trifluoromethyl, trifluoromethoxy, nitro, nitrile (—CN), oxo, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a ($C_1$-$C_6$)alkyl, ($C_3$-$C_6$)cycloalkyl, phenyl or monocyclic heteroaryl having 5 or 6 ring atoms. An "optional substituent" may be one of the foregoing substituent groups.

The term "side chain of a natural or non-natural alpha-amino acid" refers to the group R$^Y$ in a natural or non-natural amino acid of formula NH$_2$—CH(R$^Y$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When R$_2$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1$-$C_6$ alkyl ester), amino groups may be converted to amides (for example as a NHCOC$_1$-$C_6$ alkyl amide) or carbamates (for example as an NHC(=O)OC$_1$-$C_6$ alkyl or NHC(=O)OCH$_2$Ph carbamate), hydroxyl groups may be converted to ethers (for example an OC$_1$-$C_6$ alkyl or a O($C_1$-$C_6$ alkyl)phenyl ether) or esters (for example a OC(=O)C$_1$-$C_6$ alkyl ester) and thiol groups may be converted to thioethers (for example a tert-butyl or benzyl thioether) or thioesters (for example a SC(=O)C$_1$-$C_6$ alkyl thioester). Examples of side chains of non-natural alpha amino acids include those referred to below in the discussion of suitable R$_2$ groups for use in compounds of the present invention.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulphonic, glutamic, lactic, and mandelic acids and the like. For a review on suitable salts, see Handbook of Pharmaceutical Salts: Properties, Selection, and Use by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds of the invention which contain one or more actual or potential chiral centres, because of the presence of asymmetric carbon atoms, can exist as enantiomers or as a number of diastereoisomers with R or S stereochemistry at each chiral centre. The invention includes all such enantiomers and diastereoisomers and mixtures thereof.

As mentioned, the esters of the invention are converted by intracellular esterases to the carboxylic acids. Both the esters and carboxylic acids may have p38 MAP kinase inhibitory activity in their own right. The compounds of the invention therefore include not only the ester, but also the corresponding carboxylic acid hydrolysis products.

In the compounds with which the invention is concerned:
The Group D

D is an optionally substituted divalent mono- or bicyclic aryl or heteroaryl radical having 5-13 ring members. At present it is preferred that B be optionally substituted phenyl or optionally substituted pyridinyl. Preferred optional substituents in B include chloro, fluoro, methyl, methoxy and trifluoromethyl, for example when B is 2,4-difluorophenyl.
The Substituent $R_6$ $R_6$ is hydrogen or optionally substituted $C_1$-$C_3$ alkyl. Presently it is preferred that $R_6$ be hydrogen or methyl.
P/U Regioisomers Presently it is preferred that P be hydrogen and U be a radical of formula (IA) as defined above.
The Radical A In the radical of formula (IA), it is currently preferred that A be optionally substituted 1,4 phenylene. In that case preferred optional substituents include fluoro and chloro. A may also be, for example, any of the following, optionally substituted:

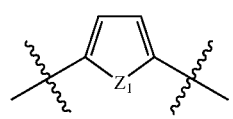
A

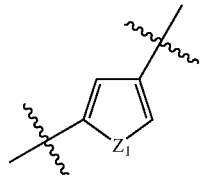
B

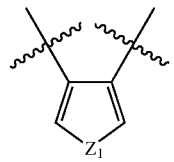
C

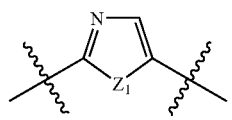
D

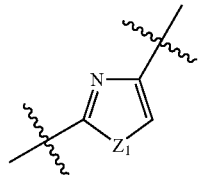
E

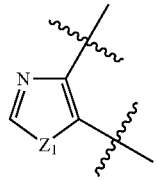
F

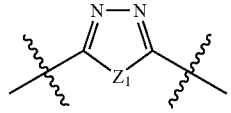
G

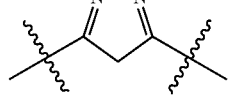
H

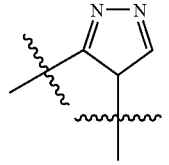
I

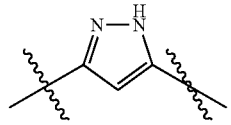
K

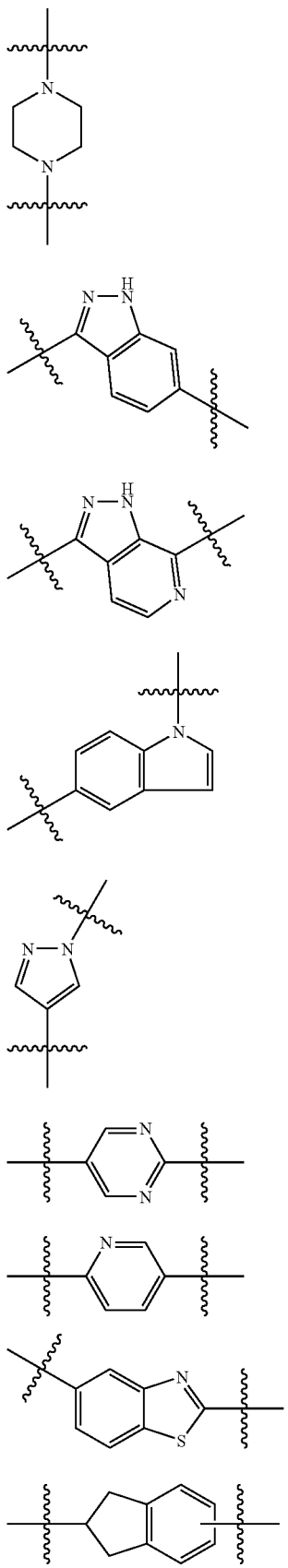
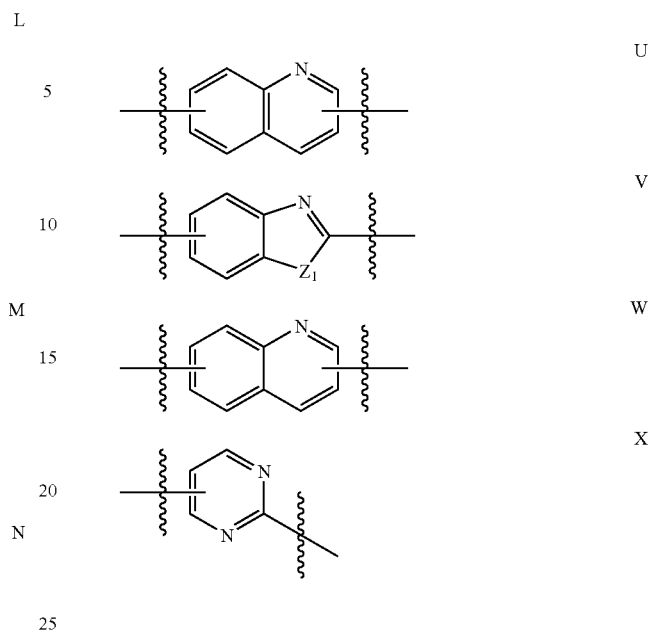
wherein $Z_1$ is NH, S or O.
A particularly preferred sub-group of compounds of the invention consists of those of formula (IIA), (IIB) and (IIC):
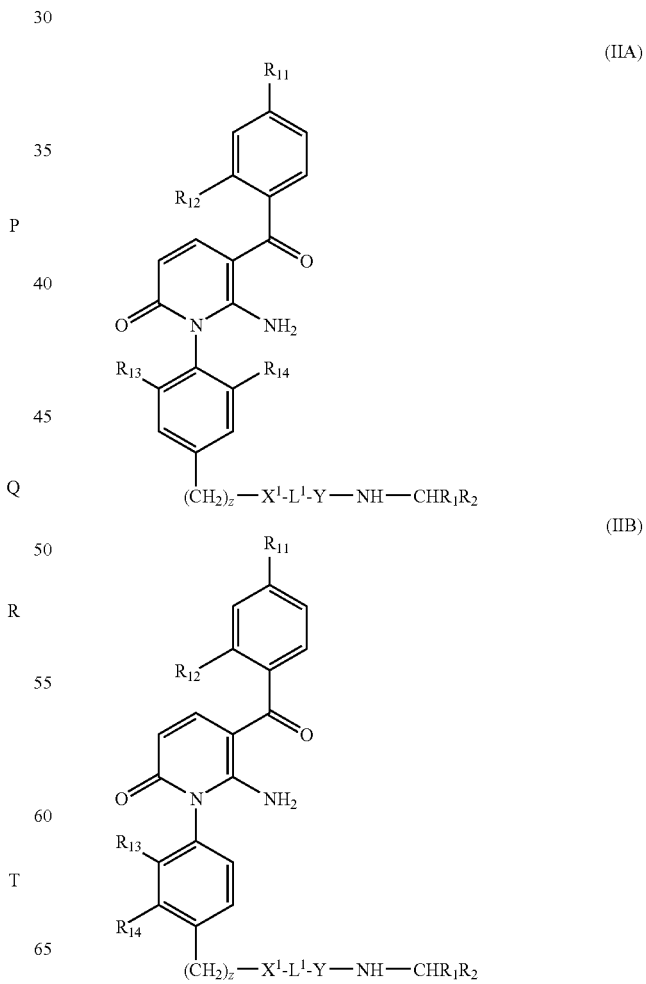

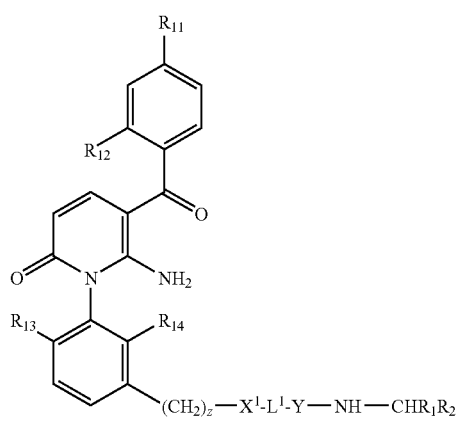

(IIC)

wherein
$R_{11}$=F, $R_{12}$=H, $R_{13}$=H and $R_{14}$=H; or
$R_{11}$=F, $R_{12}$=F, $R_{13}$=H and $R_{14}$=H; or
$R_{11}$=F, $R_{12}$=H, $R_{13}$=F and $R_{14}$=F; or
$R_{11}$=F, $R_{12}$=F, $R_{13}$=F and $R_{14}$=F; or
$R_{11}$=F, $R_{12}$=F, $R_{13}$=F and $R_{14}$=H
and wherein z, $X^1$, $L^1$, Y, $R^1$ and $R^2$ are as defined above with reference to formula (I), and as further discussed below.

The Radical —Y-$L^1$-$X^1$—[CH$_2$]$_z$—

This radical (or bond) arises from the particular chemistry strategy chosen to link the amino acid ester motif $R_1$CH($R_2$)NH— to the ring system A. Clearly the chemistry strategy for that coupling may vary widely, and thus many combinations of the variables Y, $L^1$, $X^1$ and z are possible. The precise combination of variables making up the linking chemistry between the amino acid ester motif and the ring system A will often be irrelevant to the primary binding mode of the compound as a whole. On the other hand, that linkage chemistry will in some cases pick up additional binding interactions with the enzyme. It should also be noted that the benefits of the amino acid ester motif (facile entry into the cell, esterase hydrolysis within the cell, and accumulation within the cell of active carboxylic acid hydrolysis product) are best achieved when the linkage between the amino acid ester motif and the ring system A is not a substrate for peptidase activity within the cell, which might result in cleavage of the amino acid from the molecule. Of course, stability to intracellular peptidases is easily tested by incubating the compound with disrupted cell contents, and analysing for any such cleavage.

With the foregoing general observations in mind, taking the variables making up the radical —Y-$L^1$-$X^1$—[CH$_2$]$_z$— in turn:
z may be 0 or 1, so that a methylene radical linked to the ring system A is optional;
specific preferred examples of Y when macrophage selectivity is not required include —C(=O)—, —C(=O)NH—, and —C(=O)O—; Where macrophage selectivity is required any of the other options for Y, including the case where Y is a bond, are appropriate.
In the radical $L^1$, examples of Alk$^1$ and Alk$^2$ radicals, when present, include —CH$_2$—, —CH$_2$CH$_2$—, —CH$_2$CH$_2$CH$_2$—, —CH$_2$CH$_2$CH$_2$CH$_2$—, —CH=CH—, —CH=CHCH$_2$—, —CH$_2$CH=CH—, CH$_2$CH=CHCH$_2$—, —C≡C—, —C≡CCH$_2$—, CH$_2$C≡C—, and CH$_2$C≡CCH$_2$. Additional examples of Alk$^1$ and Alk$^2$ include —CH$_2$W—, —CH$_2$CH$_2$W—, —CH$_2$CH$_2$WCH$_2$—, —CH$_2$CH$_2$WCH(CH$_3$)—, —CH$_2$WCH$_2$CH$_2$—, —CH$_2$WCH$_2$CH$_2$WCH$_2$— and —WCH$_2$CH$_2$— where W is —O—, —S—, —NH—, —N(CH$_3$)—, or —CH$_2$CH$_2$N(CH$_2$CH$_2$OH)CH$_2$—. Further examples of Alk$^1$ and Alk$^2$ include divalent cyclopropyl, cyclopentyl and cyclohexyl radicals.

In $L^1$, when n is 0, the radical is a hydrocarbon chain (optionally substituted and perhaps having an ether, thioether or amino linkage). Presently it is preferred that there be no optional substituents in $L^1$. When both m and p are 0, $L^1$ is a divalent mono- or bicyclic carbocyclic or heterocyclic radical with 5-13 ring atoms (optionally substituted). When n is 1 and at least one of m and p is 1, $L^1$ is a divalent radical including a hydrocarbon chain or chains and a mono- or bicyclic carbocyclic or heterocyclic radical with 5-13 ring atoms (optionally substituted). When present, Q may be, for example, a divalent phenyl, naphthyl, cyclopropyl, cyclopentyl, or cyclohexyl radical, or a mono-, or bi-cyclic heterocyclic radical having 5 to 13 ring members, such as piperidinyl, piperazinyl, indolyl, pyridyl, thienyl, or pyrrolyl radical, but 1,4-phenylene is presently preferred.

Specifically, in some embodiments of the invention, $L^1$, m and p may be 0 with n being 1. In other embodiments, n and p may be 0 with m being 1. In further embodiments, m, n and p may be all 0. In still further embodiments m may be 0, n may be 1 with Q being a monocyclic heterocyclic radical, and p may be 0 or 1. Alk$^1$ and Alk$^2$, when present, may be selected from —CH$_2$—, —CH$_2$CH$_2$—, and —CH$_2$CH$_2$CH$_2$— and Q may be 1,4-phenylene.

Specific examples of the radical —Y-$L^1$-$X^1$— [CH$_2$]$_z$— include —C(=O)— and —C(=O)NH— as well as —(CH$_2$)$_v$—, —(CH$_2$)$_v$O—, —C(=O)—(CH$_2$)$_v$—, —C(=O)—(CH$_2$)$_v$O—, —C(=O)—NH—(CH$_2$)$_w$—, —C(=O)—NH—(CH$_2$)$_w$O—

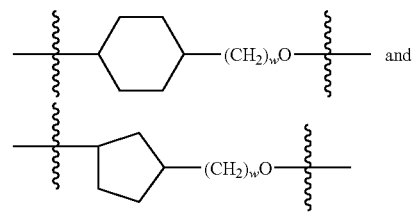

wherein v is 1, 2, 3 or 4 and w is 1, 2 or 3, such as —Y-$L^1$-$X^1$—[CH$_2$]$_z$—, is —CH$_2$—, —CH$_2$CH$_2$—, —CH$_2$CH$_2$CH$_2$—, —CH$_2$CH$_2$CH$_2$CH$_2$—, —CH$_2$O—, —CH$_2$CH$_2$O—, —CH$_2$CH$_2$CH$_2$O—, —CH$_2$CH$_2$CH$_2$CH$_2$O—, —C(=O)—CH$_2$—, —C(=O)—CH$_2$O—, —C(=O)—NH—CH$_2$—, or —C(=O)—NH—CH$_2$O—.

The Group $R_1$

In one class of compounds of the invention, $R_1$ is a carboxylic acid group. Although compounds of this class may be administered as the carboxylic acid or a salt thereof, it is preferred that they be generated in the cell by the action of an intracellular esterase on a corresponding compound in which $R_1$ is an ester group.

The ester group $R_1$ must be one which in the compound of the invention is hydrolysable by one or more intracellular carboxylesterase enzymes to a carboxylic acid group. Intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes, other enzymes such as biphenylhydrolase (BPH) may also have a role in hydrolysing the ester. In general, if the carboxylesterase hydrolyses the free amino acid ester to the parent acid it will also hydrolyse the ester motif when covalently conjugated to the inhibitor. Hence, the broken cell assay and/or the isolated carboxylesterase assay described herein provide a straightforward, quick and simple first screen for esters which have the required hydrolysis profile. Ester motifs selected in that way may then be re-assayed in the same carboxylesterase assay when conjugated to the inhibitor via the chosen conjugation chemistry, to confirm that it is still a carboxylesterase substrate in that background.

Subject to the requirement that they be hydrolysable by intracellular carboxylesterase enzymes, examples of particular ester groups $R_1$ include those of formula —(C=O)$OR_{14}$ wherein $R_{14}$ is $R_8R_9R_{10}$C— wherein
(i) $R_8$ is hydrogen or optionally substituted $(C_1-C_3)$alkyl-$(Z^1)_a$-[$(C_1-C_3)$alkyl]$_b$- or $(C_2-C_3)$alkenyl-$(Z^1)_a$-[$(C_1-C_3)$alkyl]$_b$- wherein a and b are independently 0 or 1 and $Z^1$ is —O—, —S—, or —$NR_{11}$— wherein $R_{11}$ is hydrogen or $(C_1-C_3)$alkyl; and $R_9$ and $R_{10}$ are independently hydrogen or $(C_1-C_3)$alkyl-;
(ii) $R_8$ is hydrogen or optionally substituted $R_{12}R_{13}$N—$(C_1-C_3)$alkyl- wherein $R_{12}$ is hydrogen or $(C_1-C_3)$alkyl and $R_{13}$ is hydrogen or $(C_1-C_3)$alkyl; or $R_{12}$ and $R_{13}$ together with the nitrogen to which they are attached form an optionally substituted monocyclic heterocyclic ring of 5- or 6-ring atoms or bicyclic heterocyclic ring system of 8 to 10 ring atoms, and $R_9$ and $R_{10}$ are independently hydrogen or $(C_1-C_3)$alkyl-; or
(iii) $R_8$ and $R_9$ taken together with the carbon to which they are attached form an optionally substituted monocyclic carbocyclic ring of from 3 to 7 ring atoms or bicyclic carbocyclic ring system of 8 to 10 ring atoms, and $R_{10}$ is hydrogen.

Within these classes, $R_{10}$ is often hydrogen. Specific examples of $R_{14}$ include methyl, ethyl, n- or iso-propyl, n-, sec- or tert-butyl, cyclohexyl, allyl, phenyl, benzyl, 2-, 3- or 4-pyridylmethyl, N-methylpiperidin-4-yl, tetrahydrofuran-3-yl or methoxyethyl. Currently preferred is where $R_{14}$ is cyclopentyl.

Macrophages are known to play a key role in inflammatory disorders through the release of cytokines in particular TNFα and IL-1 (van Roon et al, Arthritis and Rheumatism, 2003, 1229-1238). In rheumatoid arthritis they are major contributors to the maintenance of joint inflammation and joint destruction. Macrophages are also involved in tumour growth and development (Naldini and Carraro, Curr Drug Targets Inflamm Allergy, 2005, 3-8). Hence agents that selectively target macrophage cell proliferation could be of value in the treatment of cancer and autoimmune disease. Targeting specific cell types would be expected to lead to reduced side-effects. The inventors have discovered a method of targeting p38 kinase inhibitors to macrophages which is based on the observation that the way in which the esterase motif is linked to the p38 kinase inhibitor determines whether it is hydrolysed, and hence whether or not it accumulates in different cell types. Specifically it has been found that macrophages contain the human carboxylesterase hCE-1 whereas other cell types do not. In the general formula (I) when the nitrogen of the esterase motif $R_1$CH($R_2$)NH— is not directly linked to a carbonyl (—C(=O)—), ie when Y is not a —C(=O), —C(=O)O— or —C(=O)$NR_3$— radical, the ester will only be hydrolysed by hCE-1 and hence the inhibitors will only accumulate in macrophages. Herein, unless "monocyte" or "monocytes" is specified, the term macrophage or macrophages will be used to denote macrophages (including tumour associated macrophages) and/or monocytes.

The Amino Acid Side Chain $R_2$

Subject to the requirement that the ester group $R_1$ be hydrolysable by intracellular carboxylesterase enzymes, the identity of the side chain group $R_2$ is not critical.

Examples of amino acid side chains include
$C_1-C_6$ alkyl, phenyl, 2-, 3-, or 4-hydroxyphenyl, 2-, 3-, or 4-methoxyphenyl, 2-, 3-, or 4-pyridylmethyl, benzyl, phenylethyl, 2-, 3-, or 4-hydroxybenzyl, 2-, 3-, or 4-benzyloxybenzyl, 2-, 3-, or 4-$C_1-C_6$ alkoxybenzyl, and benzyloxy($C_1$-$C_6$alkyl)-groups;

the characterising group of a natural α amino acid, in which any functional group may be protected;

groups -[Alk]$_n R_6$ where Alk is a $(C_1-C_6)$alkyl or $(C_2-C_6)$ alkenyl group optionally interrupted by one or more —O—, or —S— atoms or —N($R_7$)— groups [where $R_7$ is a hydrogen atom or a $(C_1-C_6)$alkyl group], n is 0 or 1, and $R_6$ is an optionally substituted cycloalkyl or cycloalkenyl group;

a benzyl group substituted in the phenyl ring by a group of formula —$OCH_2COR_{15}$ where $R_{15}$ is hydroxyl, amino, $(C_1-C_6)$alkoxy, phenyl$(C_1-C_6)$alkoxy, $(C_1-C_6)$alkylamino, di$((C_1-C_6)$alkyl)amino, phenyl$(C_1-C_6)$alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid;

a heterocyclic$(C_1-C_6)$alkyl group, either being unsubstituted or mono- or di-substituted in the heterocyclic ring with halo, nitro, carboxy, $(C_1-C_6)$alkoxy, cyano, $(C_1-C_6)$alkanoyl, trifluoromethyl$(C_1-C_6)$alkyl, hydroxy, formyl, amino, $(C_1-C_6)$ alkylamino, di-$(C_1-C_6)$alkylamino, mercapto, $(C_1-C_6)$alkylthio, hydroxy$(C_1-C_6)$alkyl, mercapto$(C_1-C_6)$alkyl or $(C_1-C_6)$alkylphenylmethyl; and a group —$CR_aR_bR_c$ in which:
each of $R_a$, $R_b$ and $R_c$ is independently hydrogen, $(C_1-C_6)$ alkyl, $(C_2-C_6)$alkenyl, $(C_2-C_6)$alkynyl, phenyl$(C_1-C_6)$ alkyl, $(C_3-C_8)$cycloalkyl; or $R_c$ is hydrogen and $R_a$ and $R_b$ are independently phenyl or heteroaryl such as pyridyl; or $R_c$ is hydrogen, $(C_1-C_6)$alkyl, $(C_2-C_6)$alkenyl, $(C_2-C_6)$ alkynyl, phenyl$(C_1-C_6)$alkyl, or $(C_3-C_8)$cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently $(C_1-C_6)$alkyl, $(C_2-C_6)$ alkenyl, $(C_2-C_6)$alkynyl, phenyl$(C_1-C_6)$alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —$CO_2$H, $(C_1-C_4)$perfluoroalkyl, —$CH_2$OH, —$CO_2(C_1-C_6)$alkyl, —O$(C_1-C_6)$alkyl, —O$(C_2-C_6)$alkenyl, —S$(C_1-C_6)$ alkyl, —SO$(C_1-C_6)$alkyl, —$SO_2(C_1-C_6)$alkyl, —S$(C_2-C_6)$alkenyl, —SO$(C_2-C_6)$alkenyl, —$SO_2(C_2-C_6)$alkenyl or a group -$Q^2$-W wherein $Q^2$ represents a bond or —O—, —S—, —SO— or —$SO_2$— and W represents a phenyl, phenylalkyl, $(C_3-C_8)$cycloalkyl, $(C_3-C_8)$cycloalkylalkyl, $(C_4-C_8)$cycloalkenyl, $(C_4-C_8)$cycloalkenylalkyl, heteroaryl or heteroarylalkyl group, which group W may optionally be substituted by one or more substituents independently selected from, hydroxyl, halogen, —CN, —CO$_2$H, —CO$_2$(C$_1$-C$_6$)alkyl, —CONH$_2$, —CONH(C$_1$-C$_6$)alkyl, —CONH(C$_1$-C$_6$alkyl)$_2$, —CHO, —CH$_2$OH, (C$_1$-C$_4$)perfluoroalkyl, —O(C$_1$-C$_6$)alkyl, —S(C$_1$-C$_6$)alkyl, —SO(C$_1$-C$_6$)alkyl, —SO$_2$(C$_1$-C$_6$)alkyl, —NO$_2$, —NH$_2$, —NH(C$_1$-C$_6$) alkyl, —N((C$_1$-C$_6$)alkyl)$_2$, —NHCO(C$_1$-C$_6$)alkyl, (C$_1$-C$_6$)alkyl, (C$_2$-C$_6$)alkenyl, (C$_2$-C$_6$)alkynyl, (C$_3$-C$_8$)cycloalkyl, (C$_4$-C$_8$)cycloalkenyl, phenyl or benzyl.

Examples of particular R$_2$ groups include hydrogen (the glycine "side chain"), benzyl, phenyl, cyclohexylmethyl, cyclohexyl, pyridin-3-ylmethyl, tert-butoxymethyl, iso-butyl, sec-butyl, tert-butyl, 1-benzylthio-1-methylethyl, 1-methylthio-1-methylethyl, 1-mercapto-1-methylethyl, and phenylethyl. Presently preferred R$_2$ groups include phenyl, benzyl, iso-butyl, cyclohexyl and t-butoxymethyl.

For compounds of the invention which are to be administered systemically, esters with a slow rate of carboxylesterase cleavage are preferred, since they are less susceptible to presystemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. In the compounds of this invention, if the carbon adjacent to the alpha carbon of the alpha amino acid ester ester is monosubstituted, ie R$_2$ is CH$_2$R$^z$ (R$^z$ being the mono-substituent) then the esters tend to be cleaved more rapidly than if that carbon is di- or tri-substituted, as in the case where R$_2$ is, for example, phenyl or cyclohexyl.

As mentioned above, the compounds with which the invention is concerned are inhibitors of p38 MAK kinase activity, and are therefore of use in the treatment of diseases such as psoriasis, inflammatory bowel disease, Crohns disease, ulcerative colitis, chronic obstructive pulmonary disease, asthma, multiple sclerosis, diabetes, atopic dermatitis, graft versus host disease, or systemic lupus erythematosus and rheumatoid arthritis, in which p38 MAP kinase activity plays a part.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agent can be dissolved in the vehicle.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "*Advanced organic chemistry*", 4$^{th}$ Edition (Wiley), J March, "*Comprehensive Organic Transformation*", 2$^{nd}$ Edition (Wiley), R. C. Larock, "*Handbook of Heterocyclic Chemistry*", 2$^{nd}$ Edition (Pergamon), A. R. Katritzky), review articles such as found in "*Synthesis*", "*Acc. Chem. Res.*", "*Chem.

*Rev"*, or primary literature sources identified by standard literature searches online or from secondary sources such as *"Chemical Abstracts"* or *"Beilstein"*.

The compounds of the invention may be prepared by a number of processes generally described below and more specifically in the Examples hereinafter. In the reactions described below, it may be necessary to protect reactive functional groups, for example hydroxyl, amino and carboxy groups, where these are desired in the final product, to avoid their unwanted participation in the reactions [see for example Greene, T. W., "Protecting Groups in Organic Synthesis", John Wiley and Sons, 1999]. Conventional protecting groups may be used in conjunction with standard practice. In some instances deprotection may be the final step in the synthesis of a compound of general formula (I) and the processes according to the invention described herein after are understood to extend to such removal of protecting groups.

Examples of such methods that may be employed to the synthesis of compounds of general formula (I) are set out, but not limited to the reactions shown in Scheme 1 below.

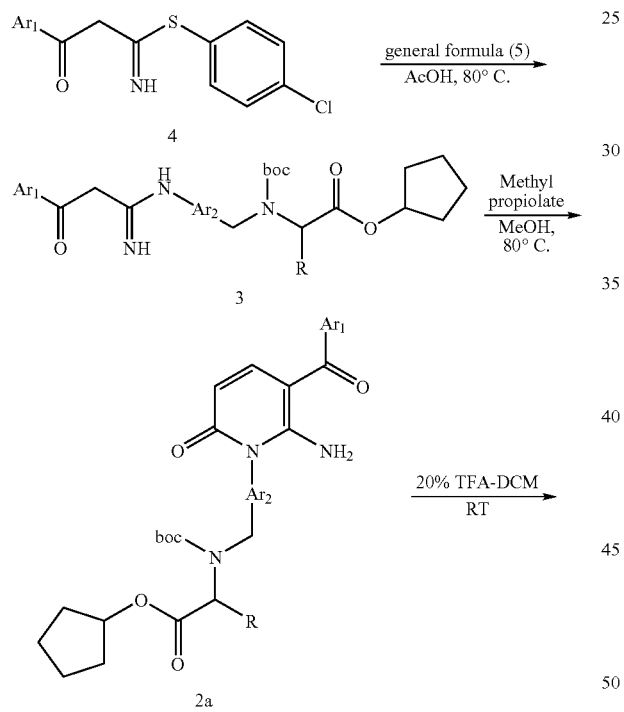

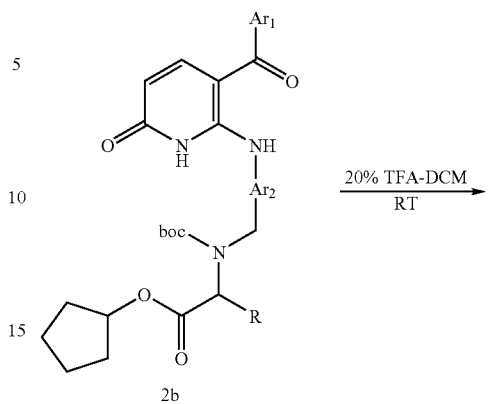

Thus, amino esters of general formula (A) may be prepared by treatment of the tert-butylcarbamate of general formula (2a) with trifluoroacetic acid in dichloromethane. Intermediates of general formula (2) may be prepared by methods described in WO 03/076405 and references therein. Amino esters of general formula (2b) may be formed as a bi-product in the synthesis of compounds of formula (2a) and treated with trifluoroacetic acid to give compounds of general formula (B).

Intermediate esters of general formula (5) may be prepared by the procedures shown in Scheme 2.

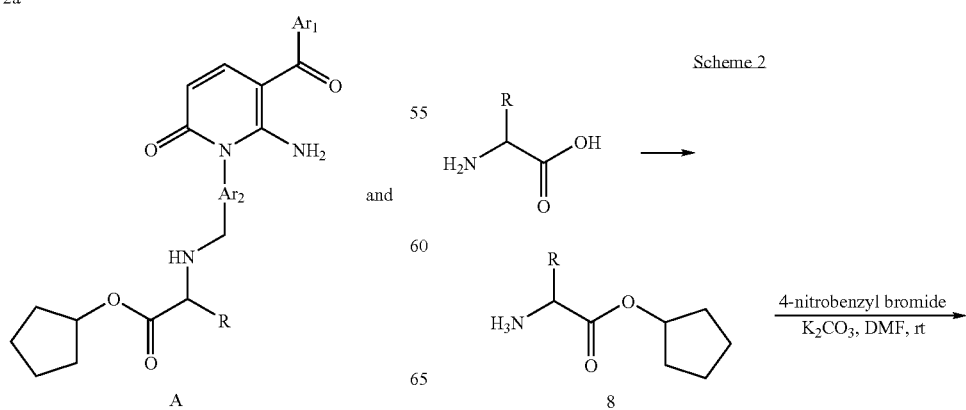

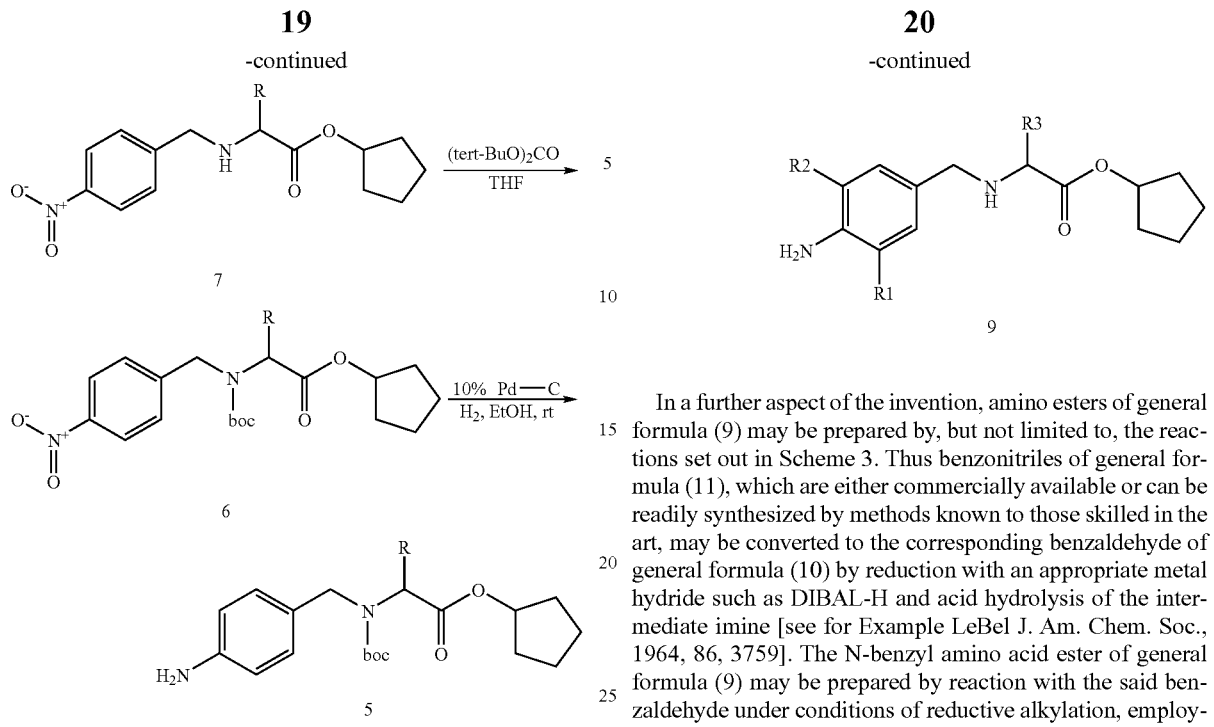

Hydrogenation of the nitrobenzyl intermediate (6) over palladium-carbon catalyst in THF provides amines of general formula (5). Intermediates of formula (6) may be prepared by the reaction of the corresponding amine with di-tert-butoxycarbonate in inert solvent such as THF at ambient temperature. Intermediates of general formula (7) may be produced by the alkylation of amino esters of formula (8) with 4-nitrobenzyl bromide. The reaction may be performed in a dialkylamide solvent such as DMF in the presence of an inorganic base such as potassium or ceasium carbonate Such reactions are set forth in March's *Advanced Organic Chemistry* [John Wiley and Sons, 1992].

An alternative general method for the synthesis of N-benzylamino acid esters of general formula (9), where further functionalisation is required on the aryl ring of the benzyl substituent is set out in Scheme 3.

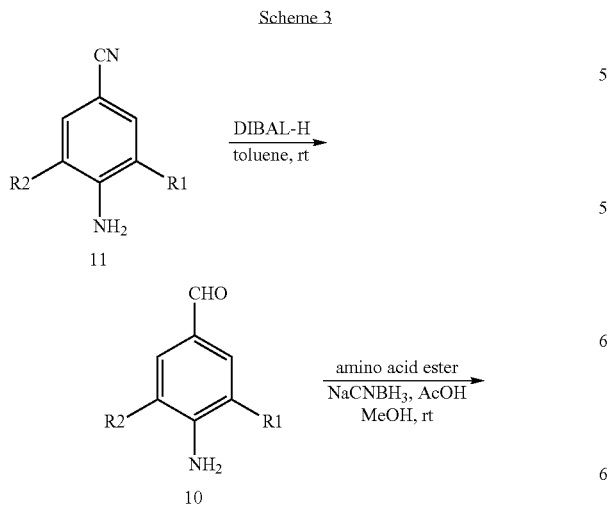

In a further aspect of the invention, amino esters of general formula (9) may be prepared by, but not limited to, the reactions set out in Scheme 3. Thus benzonitriles of general formula (11), which are either commercially available or can be readily synthesized by methods known to those skilled in the art, may be converted to the corresponding benzaldehyde of general formula (10) by reduction with an appropriate metal hydride such as DIBAL-H and acid hydrolysis of the intermediate imine [see for Example LeBel J. Am. Chem. Soc., 1964, 86, 3759]. The N-benzyl amino acid ester of general formula (9) may be prepared by reaction with the said benzaldehyde under conditions of reductive alkylation, employing borohydride reagents such as NaBH$_3$CN or NaBH(OAc)$_3$ under acidic conditions in a protic solvent such as methanol [see for example Borsch et al, J. Am. Chem. Soc., 1971, 93, 2897].

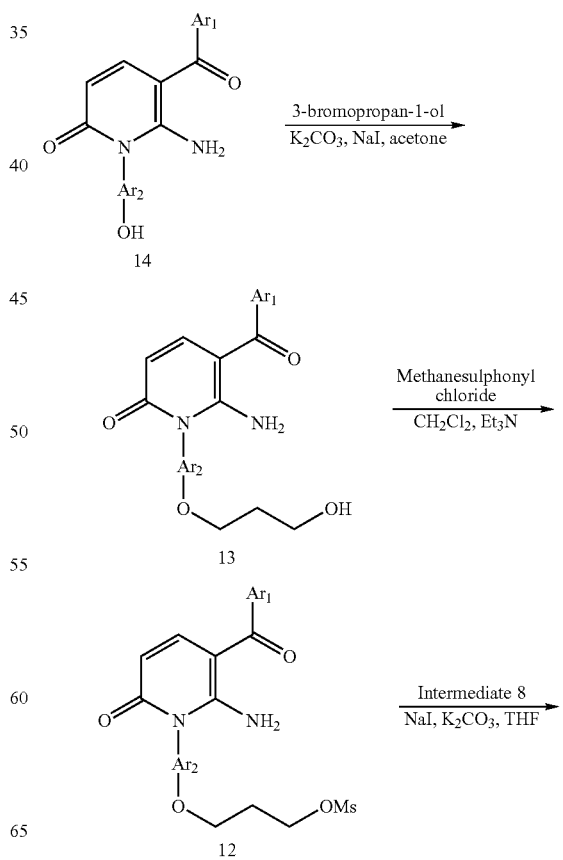

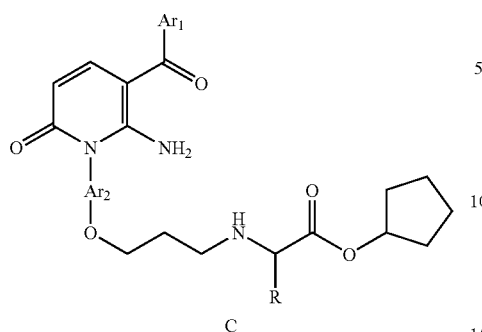

C

In a further aspect of the invention, compounds of general formula (C) may be prepared by methods set out in Scheme 4, from the alkylation of intermediates of general formula (8) with mesylates of general formula (12). The alkylation may be carried out in an inert ether solvent such as THF, in the presence of sodium iodide and inorganic bases such as potassium carbonate. It will be recognized by those skilled in the art that the corresponding alkylbromides or alkylchlorides will be of utility in this process. The preparation of mesylate (12) may be performed by treatment of the primary alcohol (13) with methanesulphonyl chloride in an inert solvent such as dichloromethane and in the presence of organic base such as triethylamine. Compounds of general formula (14) may be prepared by methods described in WO 03/076405 and references therein.

In a further aspect to the invention compounds of general formula (D) may be prepared by, but not limited to, the reactions in Scheme 5.

Scheme 5

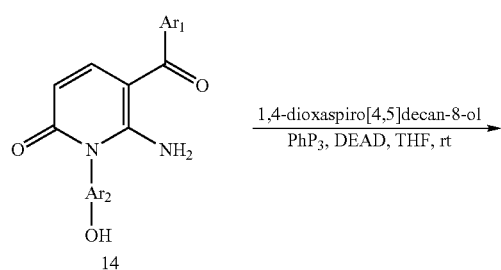

14

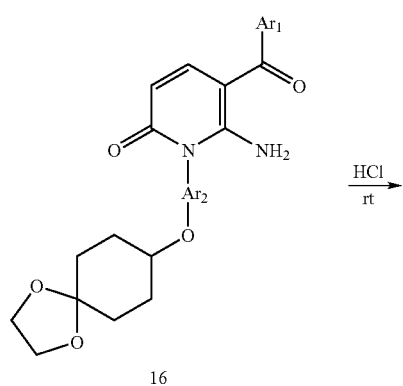

16

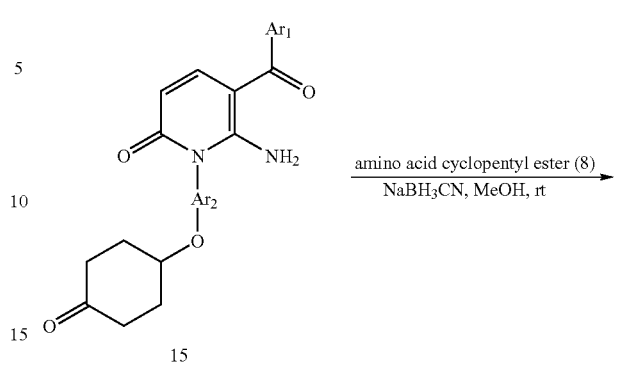

15

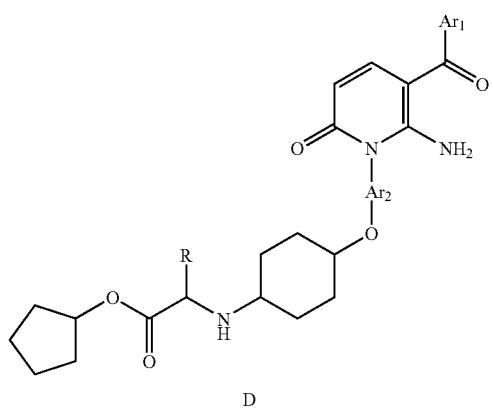

D

Thus, alcohols of general formula (14) can be alkylated with an appropriately protected cycloalkanol derivative such as 1,4-dioxaspiro[4,5]decan-8-ol using triphenylphosphine and a dialkyl azadicarboxylate such as DEAD in an inert ethereal solvent [see for example Mitsunobu et al, Bull. Chem. Soc. Jpn., 1967, 40, 2380]. Ketals of general formula (16) may be deprotected to the corresponding ketone under aqueous acidic conditions. Reductive amination of compounds of formula (16) may be achieved by treatment with amino acid esters of general formula (8) in the presence of borohydride reagents such as sodium cyanoborohydride and sodium triacetoxyborohydride under acid conditions to give compounds of general formula (D).

In a further aspect to the invention compounds of general formula (E) may be prepared by, but not limited to, the reactions in Scheme 6.

Scheme 6

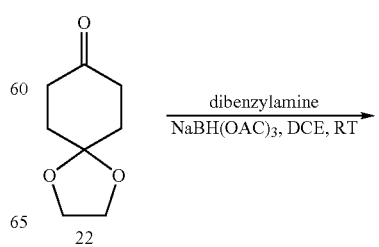

22

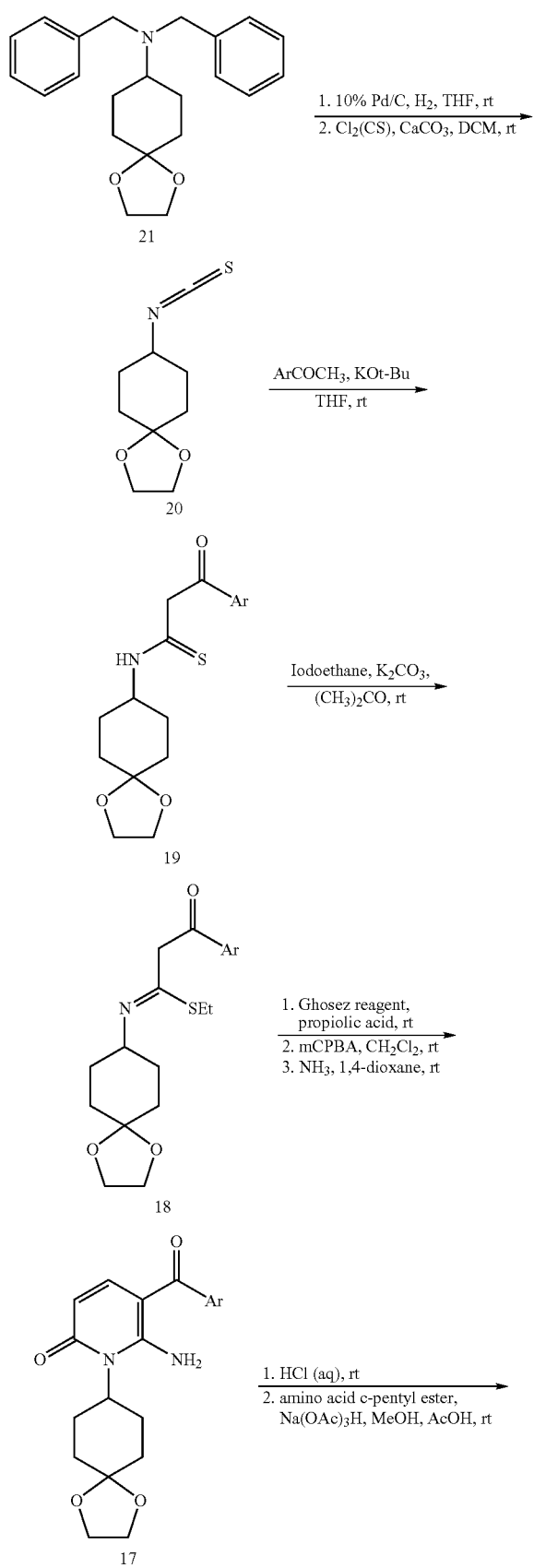

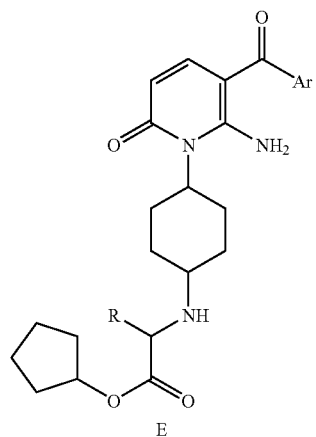

E

Reductive amination of compounds of formula (22) may be achieved by treatment with dibenzylamine in the presence of borohydride reagents such as sodium cyanoborohydride and sodium triacetoxyborohydride under acid conditions to give compounds of general formula (21). Hydrogenation of (21) and subsequent reaction with thiophosgene can give the isocyanate of general formula (20). Compounds of general formula (19) may be prepared by reaction of (20) with the corresponding acetophenone using sodium tert-butoxide. Alkylation of (19) with iodoethane may be carried out using an inorganic base such as potassium carbonate in a solvent such as acetone. Compounds of general formula (18) may be subjected to cyclisation, oxidation and then subsequent ammonia displacement to give ketals of general formula (17). Thus ketals of general formula (17) may be deprotected to the corresponding cyclohexanone intermediate under aqueous acidic conditions, the cyclohexanone then reacted with amino acid esters of general formula (8) under conditions of reductive amination employing borohydride reagents such as sodium cyanoborohydride and sodium triacetoxyborohydride.

In another aspect of the invention, amino acids of general formula (F) may be prepared by, but not restricted to methods set out in Scheme 7.

Scheme 7

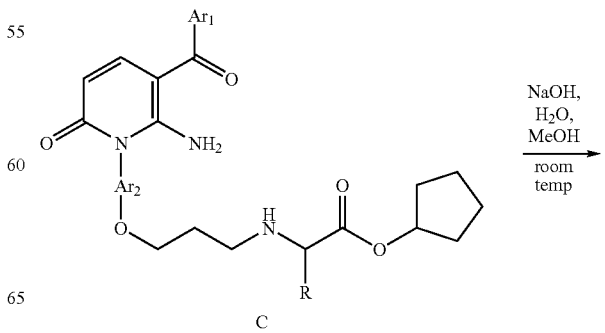

C

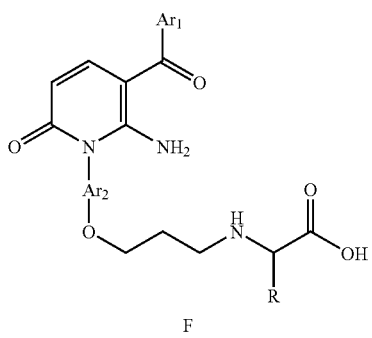

F

Thus, for example, amino acid esters of general formula (C) may be hydrolysed to the corresponding amino acids (F) by treatment with aqueous sodium or potassium hydroxide, or any appropriate base, at ambient temperature in a co-solvent such as methanol or ethanol.

In another aspect of the invention, amino acids of general formula (G) may be prepared by, but not restricted to methods set out in Scheme 8.

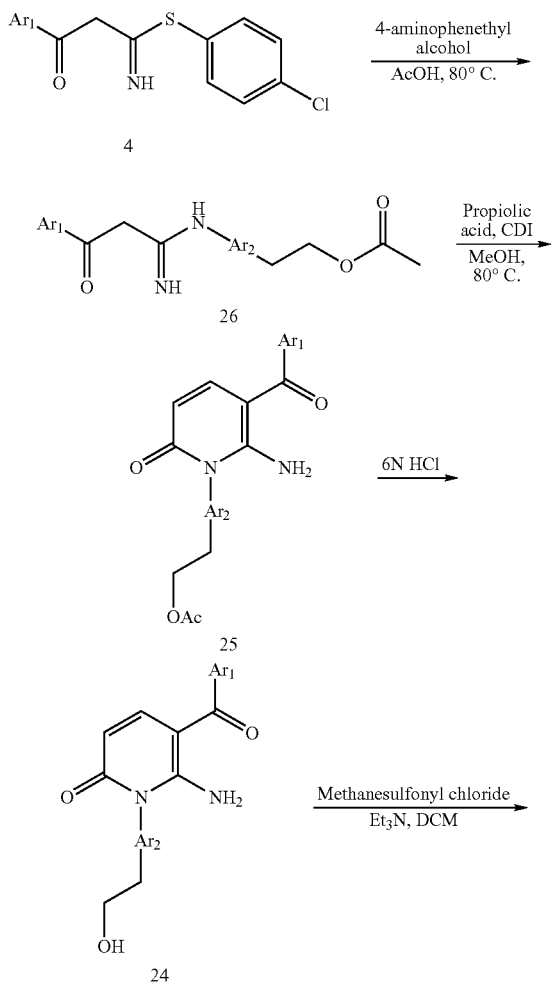

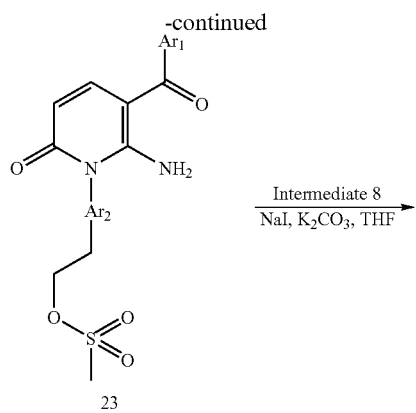

G

Thus, amino esters of general formula G may be prepared by the alkylation of intermediates of general formula (8) with mesylates of general formula (23). The alkylation may be carried out in an inert ether solvent such as THF, in the presence of sodium iodide and inorganic bases such as potassium carbonate. The preparation of mesylate (23) may be performed by treatment of the primary alcohol (24) with methanesulphonyl chloride in an inert solvent such as dichloromethane and in the presence of organic base such as triethylamine. The alcohol (24) may be prepared by deprotection of the acetyl group of intermediate (25) under acidic conditions such as HCl. Intermediates of general formula (4), (25) and (26) may be prepared by similar methods described in WO 03/076405 and references therein.

The following examples illustrate the invention. All temperatures are in ° C. The following abbreviations are used:
MeOH=methanol
EtOH=ethanol
EtOAc=ethyl acetate
Boc=tert-butoxycarbonyl
CDI=1,1'-carbonyl diimidazole
DCM=dichloromethane
DMF=dimethylformamide
DMSO=dimethyl sulfoxide
TFA=trifluoroacetic acid
THF=tetrahydrofuran
$Na_2CO_3$=sodium carbonate
HCl=hydrochloric acid
DIPEA=diisopropylethylamine
NaH=sodium hydride
NaOH=sodium hydroxide
$NaHCO_3$=sodium hydrogen carbonate
Pd/C=palladium on carbon
TME=tert-butyl methyl ether
$N_2$=nitrogen Na₂SO₄=sodium sulphate
Et₃N=triethylamine
NH₃=ammonia
TMSCl=trimethylchlorosilane
TBME=tertiary butyl methyl ether
NH₄Cl=ammonium chloride
LiAlH₄=lithium aluminium hydride
MgSO₄=magnesium sulfate
ⁿBuLi=n-butyllithium
CO₂=carbon dioxide
EDCI=N-(3-Dimethylaminopropyl)-A-ethylcarbodiimide hydrochloride
Et₂O=diethyl ether
LiOH=lithium hydroxide
HOBt=1-hydroxybenzotriazole
ELS=Evaporative Light Scattering
TLC=thin layer chromatography
ml=milliliter(s)
g=gram(s)
mg=milligram(s)
mol=moles
mmol=millimole(s)
LCMS=high performance liquid chromatography/mass spectrometry
NMR=nuclear magnetic resonance
RT=room temperature Microwave irradiation was carried out using a CEM Discover focused microwave reactor. Solvents were removed using a GeneVac Series I without heating or a Genevac Series II with VacRamp at 30° C. or a Buchi rotary evaporator. Purification of compounds by flash chromatography column was performed using silica gel, particle size 40-63 μm (230-400 mesh) obtained from Silicycle. Purification of compounds by preparative HPLC was performed on Gilson systems using reverse phase ThermoHypersil-Keystone Hyperprep HS C18 columns (12 μm, 100×21.2 mm), gradient 20-100% B (A=water/0.1% TFA, B=acetonitrile/0.1% TFA) over 9.5 min, flow=30 ml/min, injection solvent 2:1 DMSO: acetonitrile (1.6 ml), UV detection at 215 nm.

¹H NMR spectra were recorded on a Bruker 400 MHz AV or a Bruker 300 MHz AV spectrometer in deuterated solvents. Chemical shifts (δ) are in parts per million. Thin-layer chromatography (TLC) analysis was performed with Kieselgel 60 F₂₅₄ (Merck) plates and visualized using UV light.

Analytical HPLCMS was performed on Agilent HP1100, Waters 600 or Waters 1525 LC systems using reverse phase Hypersil BDS C18 columns (5 μm, 2.1×50 mm), gradient 0-95% B (A=water/0.1% TFA, B=acetonitrile/0.1% TFA) over 2.10 min, flow=1.0 ml/min. UV spectra were recorded at 215 nm using a Gilson G1315A Diode Array Detector, G1214A single wavelength UV detector, Waters 2487 dual wavelength UV detector, Waters 2488 dual wavelength UV detector, or Waters 2996 diode array UV detector. Mass spectra were obtained over the range m/z 150 to 850 at a sampling rate of 2 scans per second or 1 scan per 1.2 seconds using Micromass LCT with Z-spray interface or Micromass LCT with Z-spray or MUX interface. Data were integrated and reported using OpenLynx and OpenLynx Browser software.

Intermediates

Intermediate 1A Cyclopentyl(S)-2-[(4-Aminobenzyl)-tert-butoxycarbonyl amino]-4-methylpentanoate

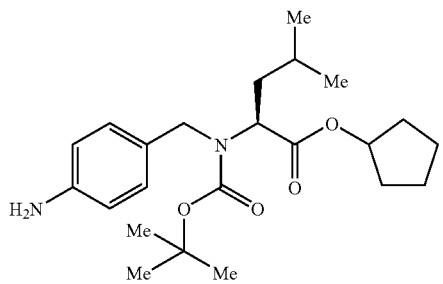

Cyclopentyl(S)-2-[tert-Butoxycarbonyl-(4-nitrobenzyl) amino]-4-methylpentanoate (3.8 g, 8.74 mmol) was dissolved in EtOH (100 ml) before addition of Pd/C (10% wet) catalyst (100 mg) and hydrogenated under balloon pressure at room temperature for 18 h. The reaction mixture was filtered through a pad of celite and evaporated to dryness to give a pink coloured solid (3.15 g, 89% yield). LCMS purity 100%, m/z 405 [M+H]⁺.

The nitrobenzyl carbamate starting material for this procedure was prepared as follows:

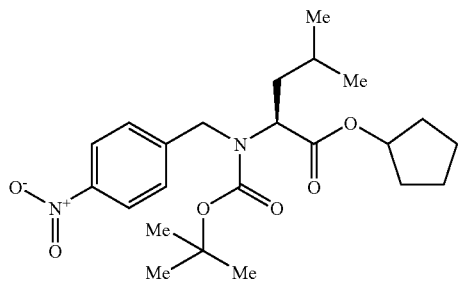

Cyclopentyl(S)-(4-nitrobenzyl)amino]-4-methylpentanoate (15.8 g, 47.4 mmol) was dissolved in THF (250 ml) before addition of potassium carbonate (7.58 g, 56.9 mmol) and water (150 ml). Di-tert-butyldicarbonate (15.5 g, 71.1 mmol) was added and the reaction mixture heated to 50° C. for 18 h. The reaction mixture was concentrated under reduced pressure to remove volatiles giving an aqueous residue which was extracted with EtOAc (200 ml). The EtOAc layer was washed consecutively with 0.1 M HCl (150 ml), sat. aq. NaHCO₃ and water (150 ml). The organic layer was dried (Na₂SO₄), filtered and concentrated to dryness. After purification by flash column chromatography (10% EtOAc/hexane) the product was isolated (9.36 g, 46% yield). LC purity 94%, m/z 435 [M+H]⁺.

The nitrobenzylamino starting material used in this procedure was prepared as follows

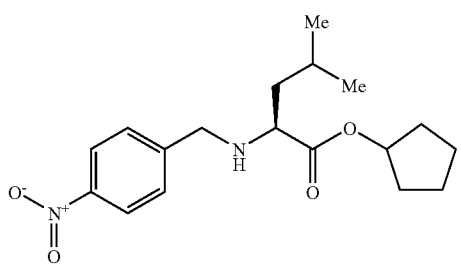

4-Nitrobenzyl bromide (11 g, 50 mmol) was dissolved in DMF (180 ml) and potassium carbonate (13.6 g, 99 mmol) added, followed by L-leucine cyclopentyl ester (Intermediate 8) (16 g, 43 mmol). The reaction was stirred for 18 h at RT. The residue was diluted with EtOAc (500 ml) and washed with water (3×100 ml), dried (Na$_2$SO$_4$) filtered and concentrated to dryness to give the crude product (15.8 g) which was used in the next step without further purification. LCMS purity 60%, m/z 335 [M+H]$^+$.

The following compounds were prepared in a similar manner:

Intermediate 1B Cyclopentyl(S)-2-[(4-Aminobenzyl)-tert-butoxycarbonyl amino]-3-phenylpropionate

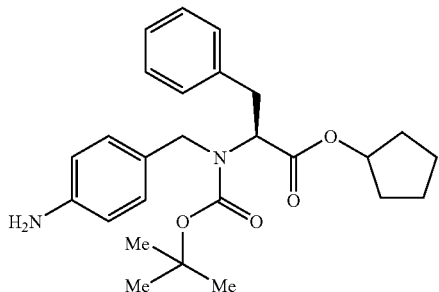

LCMS purity 75%, m/z 439 [M+H]$^+$.

Intermediate 1C Cyclopentyl(S)-[(4-Aminobenzyl)-tert-butoxycarbonyl amino]-phenylacetate

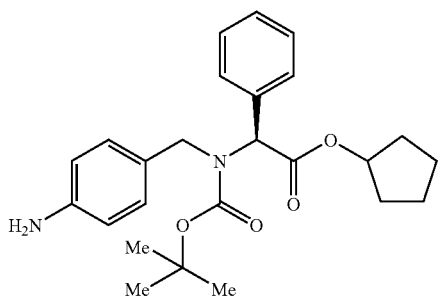

LCMS purity 100%, m/z 425 [M+H]$^+$.

Intermediate 1D Cyclopentyl(S)-2-[(4-Amino-3,5-difluorobenzyl)-tert-butoxycarbonyl amino]-4-methylpentanoate

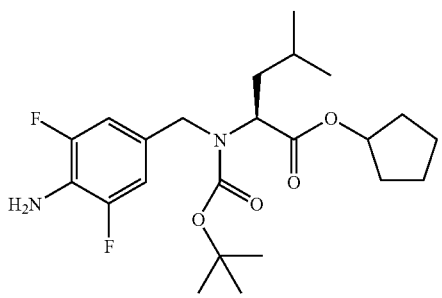

Cyclopentyl 2(S)-(4-amino-3,5-difluorobenzyl)amino]-4-methylpentanoate (2.54 g crude, assume 5.73 mmol) was dissolved in a mixture of THF (25 ml) and water (25 ml). K$_2$CO$_3$ (5.15 g, 37.3 mmol) and Boc$_2$O (8.14 g, 37.2 mmol) were added and stirring at RT was continued for 18 h. The volatiles were removed under reduced pressure and the residual aqueous layer was extracted with EtOAc (50 ml). The organic layer dried (Na$_2$SO$_4$), filtered and concentrated under reduced pressure. Purification by flash chromatography (5% EtOAc/heptane) gave the N-Boc-protected product (1.0 g, 40%). LCMS purity 89% m/z 441 [M+H]$^+$.

The benzylamino carbamate used as starting material was prepared as follows

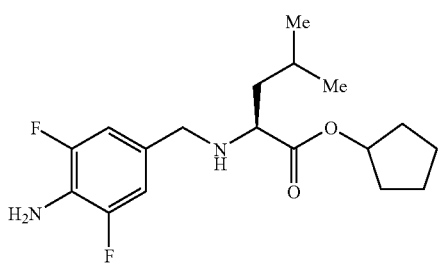

To a solution of 4-amino-3,5-difluorobenzaldehyde (0.90 g, 5.73 mmol) in 1/1 MeOH/DMF (16 ml), L-leucine cyclopentyl ester (Intermediate 8) (3.19 g, 8.59 mmol) and K$_2$CO$_3$ (1.19 g, 8.59 mmol) were added. The reaction mixture was adjusted to pH 5-6 using glacial acetic acid (dropwise) and was stirred for 1 h before addition of NaCNBH$_3$ (0.72 g, 11.46 mmol). Stirring was continued at room temperature for 18 h. The reaction mixture was concentrated to remove MeOH, diluted with EtOAc (20 ml), washed with NaHCO$_3$ (5 ml) followed by water (10 ml). The organic layer dried (Na$_2$SO$_4$), filtered and concentrated in vacuo to give the crude product (2.54 g) which was reacted in the next step without purification. LC purity=68%.

The benzaldehyde used as starting material was prepared as follows;

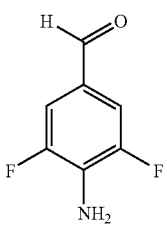

To a stirred solution of 4-amino-3,5-difluorobenzonitrile (2.0 g, 12.98 mmol) in toluene (16 ml) was added dropwise DIBAL (1.5M in toluene) at 0° C. The reaction mixture was warmed to RT and stirring continued for 2 h. The reaction was quenched by dropwise addition to 10% aq citric acid (10 ml). EtOAc (50 ml) and saturated aq potassium sodium tartrate (Rochelle's salt) (30 ml) were added and the mixture was vigorously stirred for 20 min. The organic layer was isolated and washed with water (10 ml), dried ($Na_2SO_4$), filtered and concentrated to dryness to give a pale yellow solid (1.9 g, 93%). LCMS purity 92%, m/z 158 $[M+H]^+$.

The following compounds were prepared in a similar manner:

Intermediate 1E Cyclopentyl(S)-2-[(4-Amino-3,5-difluorobenzyl)-tert-butoxy carbonylamino]-3-phenylpropionate

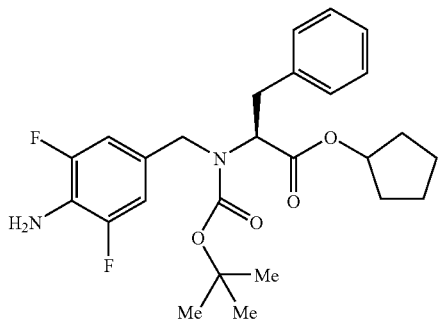

LCMS purity 86%, m/z 475 $[M+H]^+$.

Intermediate 1F Cyclopentyl(S)-2-[(4-Amino-3,5-difluorobenzyl)-tert-butoxy carbonylamino]-phenylacetate

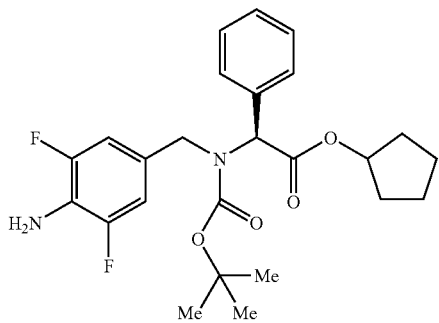

LCMS purity 86%, m/z 461 $[M+H]^+$.

Intermediate 2A Cyclopentyl(S)-[tert-Butoxycarbonyl-(4-{[3-(4-fluoro phenyl)-3-oxopropionimidoyl]aminobenzyl)aminophenylacetate

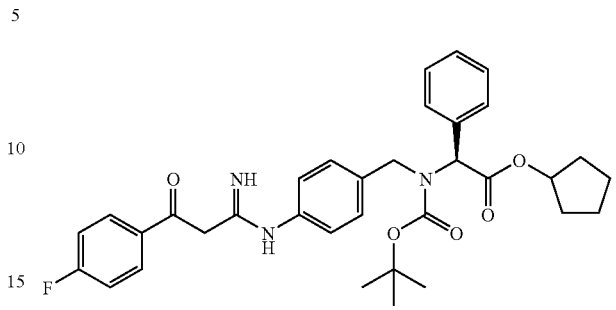

A mixture of 3-(4-fluorophenyl)-3-oxothiopropionimidic acid 4-chlorophenyl ester [WO 03/076405] (300 mg, 0.874 mmol), Intermediate 1C (0.41 g, 0.961 mmol) and glacial acetic acid (3 ml) was stirred at 80° C. for 2 h. Reaction mixture was evaporated to dryness under reduced pressure to give a thick residue which was triturated with ether (3 ml). The resultant solid was collected by suction filtration. The product was neutralised by partitioning between EtOAc (20 ml) and sat aq $NaHCO_3$ (10 ml). The organic layer was dried ($Na_2SO_4$), filtered and concentrated in vacuo. Yield=305 mg (59%). LCMS purity=75%, m/z 588 $[M+H]^+$. The product was used in the next step without further purification.

The following starting materials were prepared in an analogous manner:

Intermediate 2B Cyclopentyl(S)-2-[tert-Butoxycarbonyl-(4-{[3-(4-fluoro phenyl)-3-oxopropionimidoyl]amino}benzyl)amino]-3-phenylpropionate

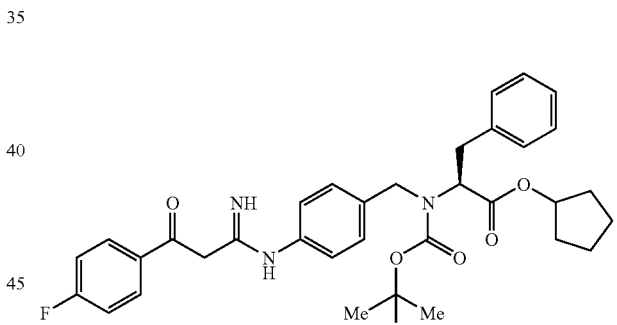

From Intermediate 1B, LCMS purity 76%, m/z 602 $[M+H]^+$.

Intermediate 2C Cyclopentyl(S)-2-[tert-Butoxycarbonyl-(4-{[3-(4-fluoro Phenyl)-3-oxopropionimidoyl]amino}benzyl)amino]-4-methylpentanoate

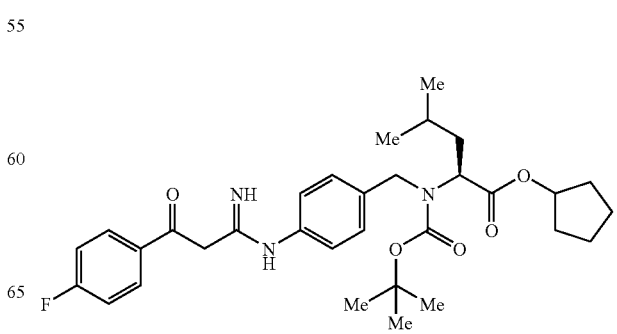

From Intermediate 1A, LCMS purity 55%, m/z 568 [M+H]+.

Intermediate 2D Cyclopentyl(S)-[tert-Butoxycarbonyl-(4-[3-(2,4-fluorophenyl)-3-oxopropionimidoyl]aminobenzyl)aminophenylacetate

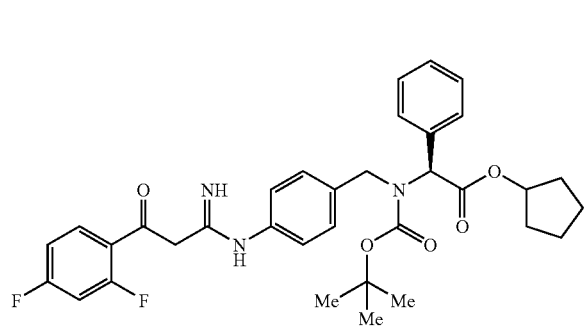

From Intermediate 1C, LCMS purity 76%, m/z 606 [M+H]+.

Intermediate 2E Cyclopentyl(S)-2-[tert-Butoxycarbonyl-(4-{[3-(2,4-difluoro phenyl)-3-oxopropionimidoyl]amino}benzyl)amino]-3-phenylpropionate

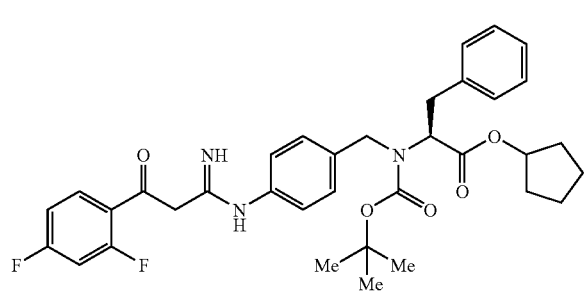

From Intermediate 1B, LCMS purity 78%, m/z 620 [M+H]+.

Intermediate 2F Cyclopentyl(S)-2-[tert-Butoxycarbonyl-(4-{[3-(2,4-difluoro phenyl)-3-oxopropionimidoyl]amino}benzyl)amino]-4-methylpentanoate

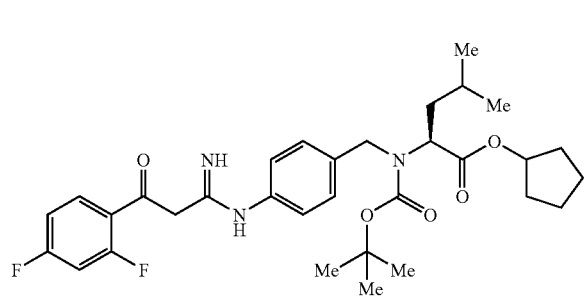

From Intermediate 1A, LCMS purity 76%, m/z 586 [M+H]+.

Intermediate 2G Cyclopentyl(S)-[tert-Butoxycarbonyl-(4-[3-(3-methyl-4-fluorophenyl)-3-oxopropionimidoyl]aminobenzyl)aminophenylacetate

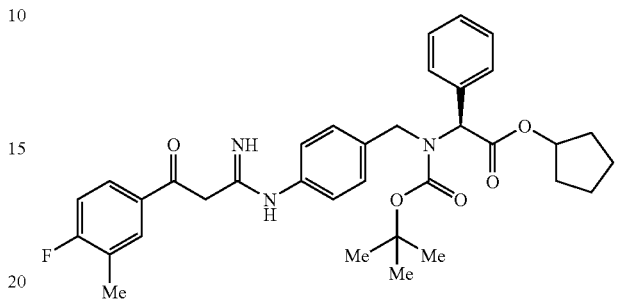

From Intermediate 1C, LCMS purity 77%, m/z 602 [M+H]+.

Intermediate 2H Cyclopentyl(S)-2-[tert-Butoxycarbonyl-(4-{[3-(3-methyl-4-fluorophenyl)-3-oxopropionimidoyl]amino}benzyl)amino]-3-phenyl propionate

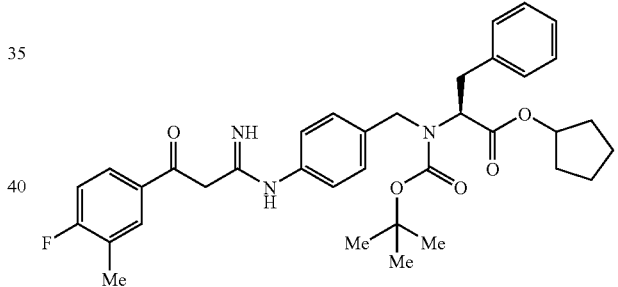

From Intermediate 1B, LCMS purity 77%, m/z 616 [M+H]+.

Intermediate 2I Cyclopentyl(S)-2-[tert-Butoxycarbonyl-(4-{[3-(3-methyl-4-fluorophenyl)-3-oxopropionimidoyl]amino}benzyl)amino]-4-methyl pentanoate

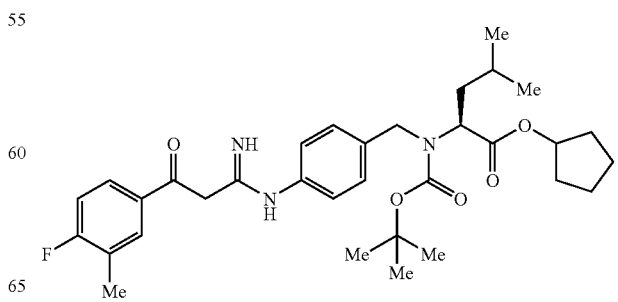

From Intermediate 1A, LCMS purity 77%, m/z 582 [M+H]⁺.

Intermediate 2J Cyclopentyl(S)-[tert-Butoxycarbonyl-(3,5-difluoro-4-{[3-(4-fluorophenyl)-3-oxo-propionimidoyl]amino}benzyl)amino]phenylacetate

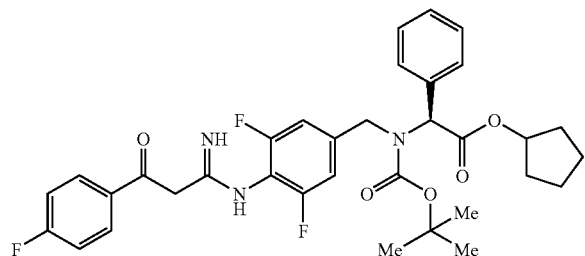

From Intermediate 1F, LCMS purity %, m/z 624[M+H]⁺.

Intermediate 2K Cyclopentyl(S)-2-[tert-Butoxycarbonyl-(3,5-difluoro-4-{[3-(4-fluoro-phenyl)-3-oxo-propionimidoyl]amino}benzyl)amino]-4-methyl pentanoate

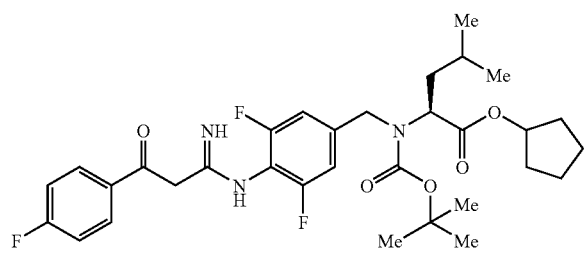

From Intermediate 1D, LCMS purity %, m/z 604 [M+H]⁺.

Intermediate 2L Cyclopentyl(S)-2-[tert-Butoxycarbonyl-(3,5-difluoro-4-{[3-(4-fluoro-phenyl)-3-oxo-propionimidoyl]amino}benzyl)-amino]-3-phenyl propionate

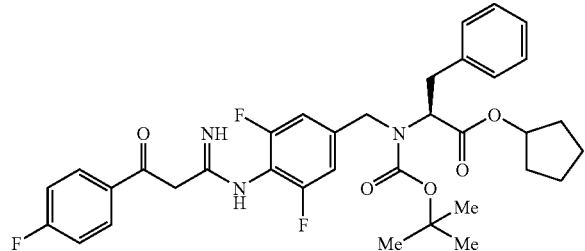

From Intermediate 1E, LCMS purity 100%, m/z 638 [M+H]⁺.

Intermediate 2M Cyclopentyl(S)-2-[tert-Butoxycarbonyl-(3,5-difluoro-4-{[3-(2,4-difluorophenyl)-3-oxopropionimidoyl]amino}benzyl)amino]-4-methyl-pentanoate

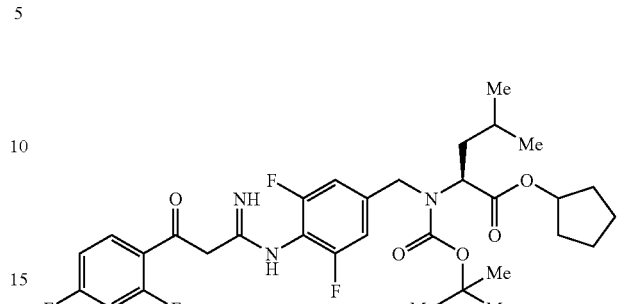

From Intermediate 1D, LCMS purity 86%, m/z 622 [M+H]⁺.

Intermediate 3A Cyclopentyl(S)-({4-[6-Amino-5-(4-fluorobenzoyl)-2-oxo-2H-pyridinyl-1-yl]benzyl}-tert-butoxycarbonylamino)phenylacetate

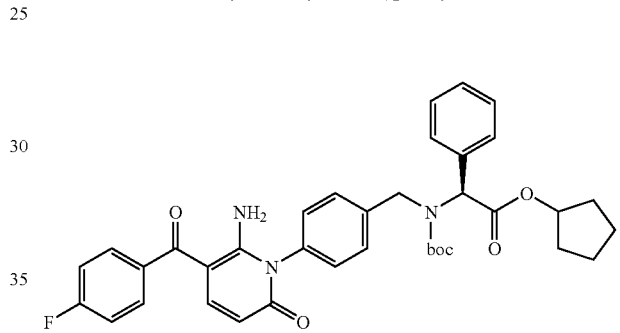

To a solution of Intermediate 2A (305 mg, 0.52 mmol) in MeOH (5 ml) was added methyl propiolate (70 µl, 0.78 mmol). The mixture was heated at 80° C. for 3 h. The reaction mixture was concentrated in vacuo and the residue was purified by column chromatography (30% EtOAc/heptane). Yield=200 mg (60%). LCMS purity 80%, m/z 640 [M+H]⁺.

The following compounds were produced in a similar fashion:

Intermediate 3B Cyclopentyl(S)-({4-[6-Amino-5-(2,4-difluorobenzoyl)-2-oxo-2H-pyridinyl-1-yl]benzyl}-tert-butoxycarbonylamino)phenylacetate

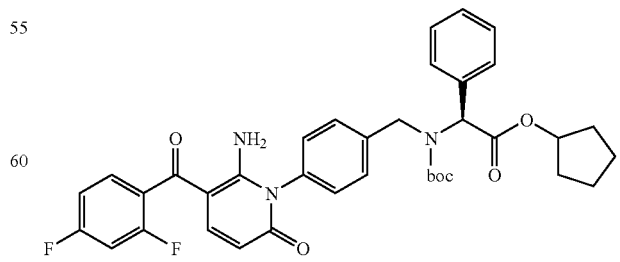

From Intermediate 2D, LCMS purity 71%, m/z 658 [M+H]⁺.

Intermediate 3C Cyclopentyl(S)-({4-[6-Amino-5-(3-methyl-4-fluorobenzoyl)-2-oxo-2H-pyridinyl-1-yl]benzyl}-tert-butoxycarbonylamino)phenylacetate

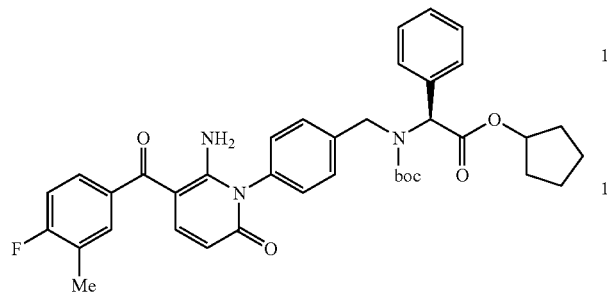

From Intermediate 2G, LCMS purity 73%, m/z 654 [M+H]⁺.

Intermediate 3D Cyclopentyl(S)-2-({4-[6-Amino-5-(4-fluorobenzoyl)-2-oxo-2H-pyridin-1-yl]benzyl}-tert-butoxycarbonylamino)-3-phenylpropionate

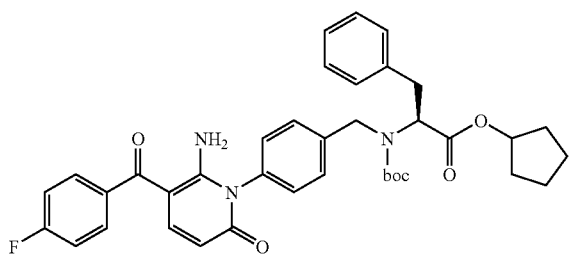

From Intermediate 2B, LCMS purity 64%, m/z 654 [M+H]⁺.

Intermediate 3E Cyclopentyl(S)-2-({4-[6-Amino-5-(2,4-difluorobenzoyl)-2-oxo-2H-pyridin-1-yl]-benzyl}-tert-butoxycarbonylamino)-3-phenylpropionate

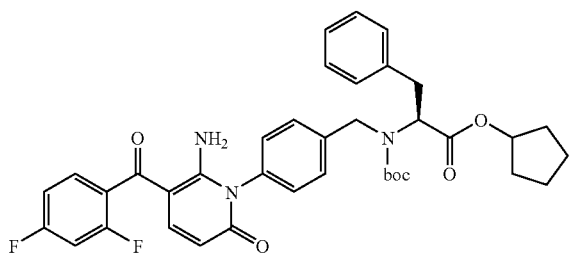

From Intermediate 2E, LCMS purity 59%, m/z 672 [M+H]⁺.

Intermediate 3F Cyclopentyl(S)-2-({4-[6-Amino-5-(3-methyl-4-fluorobenzoyl)-2-oxo-2H-pyridin-1-yl]-benzyl}-tert-butoxycarbonylamino)-3-phenyl propionate

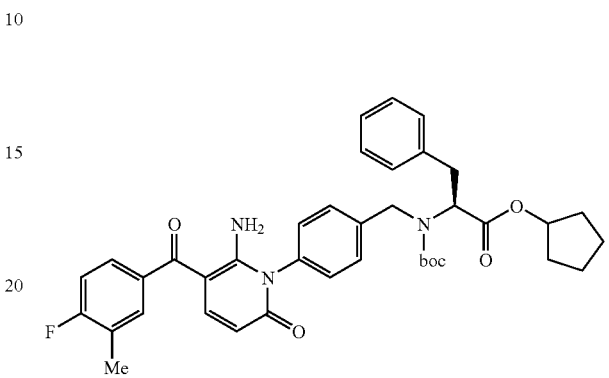

From Intermediate 2H, LCMS purity 87%, m/z 668 [M+H]⁺.

Intermediate 3G Cyclopentyl(S)-2-({4-[6-Amino-5-(4-fluorobenzoyl)-2-oxo-2H-pyridin-1-yl]benzyl}-tert-butoxycarbonylamino)-4-methylpentanoate

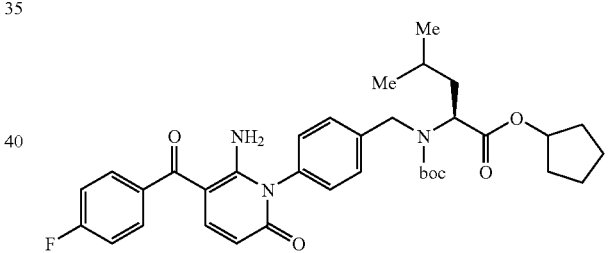

From Intermediate 2C, LCMS purity 82%, m/z 620 [M+H]⁺.

Intermediate 3I Cyclopentyl(S)-2-({4-[6-Amino-5-(2,4-difluorobenzoyl)-2-oxo-2H-pyridin-1-yl]benzyl}-tert-butoxycarbonylamino)-4-methylpentanoate

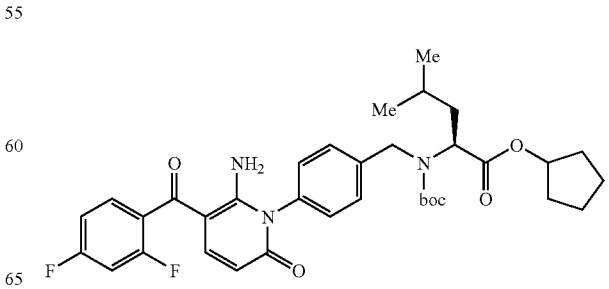

From Intermediate 2F, LCMS purity 84%, m/z 638 [M+H]⁺.

Intermediate 3J Cyclopentyl(S)-2-({4-[6-Amino-5-(3-methyl-4-fluorobenzoyl)-2-oxo-2H-pyridin-1-yl]benzyl}-tert-butoxycarbonylamino)-4-methylpentanoate

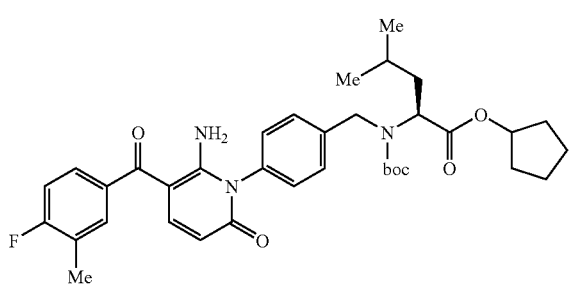

From Intermediate 2I, LCMS purity 90%, m/z 634 [M+H]⁺.

Intermediate 3K Cyclopentyl(S)-2-({4-[6-Amino-5-(4-fluorobenzoyl)-2-oxo-2H-pyridin-1-yl]-3,5-difluorobenzyl}-tert-butoxycarbonylamino)-3-phenyl propionate

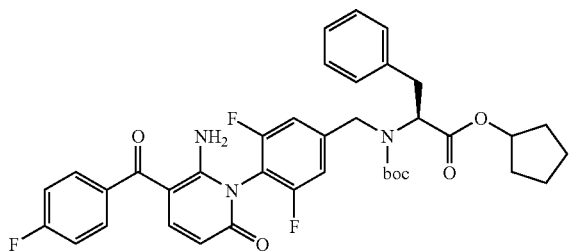

From Intermediate 2L, LCMS purity 92%, m/z 690 [M+H]⁺.

Intermediate 3L Cyclopentyl(S)-2-({4-[6-Amino-5-(2,4-difluorobenzoyl)-2-oxo-2H-pyridin-1-yl]-3,5-difluorobenzyl}-tert-butoxycarbonylamino)-4-methyl pentanoate

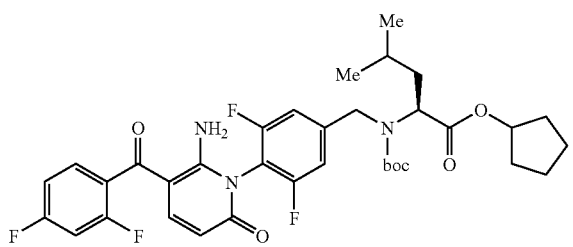

From Intermediate 2M, LCMS purity 92%, m/z 674 [M+H]⁺.

Intermediate 4A Methanesulfonic acid 3-{4-[6-amino-5-(4-fluoro-3-methyl-benzoyl)-2-oxo-2H-pyridin-1-yl]phenoxy}propyl ester

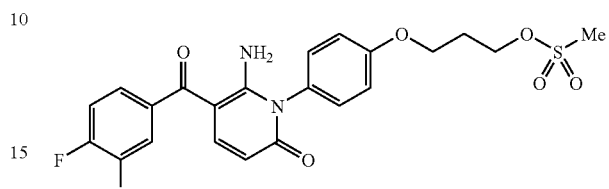

To a suspension of 6-Amino-5-(4-fluoro-3-methyl-benzoyl)-1-[4-(3-hydroxy-propoxy)-phenyl]-1H-pyridin-2-one (100 mg, 0.25 mmol) in anhydrous DCM (1 ml) at 0° C. was added methanesulfonyl chloride (21.5 µl, 0.28 mmol) followed by Et₃N (70 µl, 0.50 mmol). The reaction mixture was allowed to warm up to RT and stirred for 10-20 min to completion, monitored by TLC (5% MeOH/DCM). The reaction mixture was diluted with DCM (10 ml), washed with 10% citric acid (5 ml), followed by sat aq NaHCO₃ (5 ml) and water (5 ml). The DCM layer was dried (Na₂SO₄), filtered and concentrated in vacuo. Yield=105 mg (88%). LCMS purity=79% m/z=475 [M+H]⁺. This material was used in the next step without further purification.

The alcohol used as starting material was prepared as follows:

The 6-Amino-5-(4-fluoro-3-methyl-benzoyl)-1-[4-(3-hydroxy-propoxy)-phenyl]-1H-pyridin-2-one was prepared as shown below.

A mixture of 6-Amino-5-(4-fluoro-3-methyl-benzoyl)-1-[4-hydroxy-phenyl]-1H-pyridin-2-one [WO 03/076405] (0.80 g, 2.37 mmol), 3-bromo-1-propanol (0.23 ml, 2.60 mmol), K₂CO₃ (1.37 g, 9.46 mmol), NaI (0.73 g, 4.86 mmol) in acetone (20 ml) was heated at 70° C. for 18 h under N₂. The reaction mixture was concentrated under reduced pressure, suspended in water (20 ml) and the resulting solid was filtered and washed with ether (0.5 ml). Yield=0.8 g (85%). LCMS purity=96%, m/z 397 [M+H]⁺

The following methanesulphonate intermediates were prepared in a similar manner to Intermediate 4A using methods described in WO 03/076405 for the synthesis of the corresponding 4-hydroxyphenyl intermediates.

Intermediate 4B Methanesulfonic acid 3-{4-[6-amino-5-(4-fluorobenzoyl)-2-oxo-2H-pyridin-1-yl]phenoxy}propyl ester

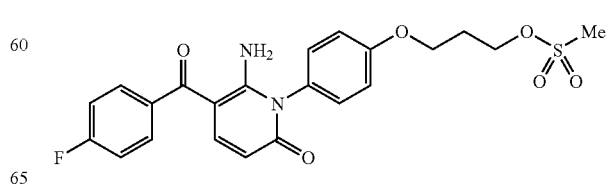

LCMS purity 66%, m/z 461 [M+H]⁺.

Intermediate 4C Methanesulfonic acid 3-{4-[6-amino-5-(2,4-difluorobenzoyl)-2-oxo-2H-pyridin-1-yl]phenoxy}propyl ester

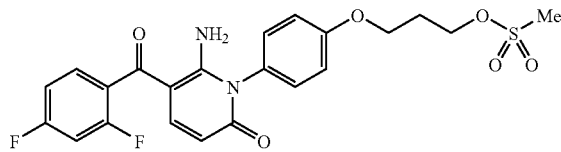

LCMS purity 88%, m/z 479 [M+H]+.

Intermediate 4D Methanesulfonic acid 3-{4-[6-amino-5-(4-fluoro-3-methyl-benzoyl)-2-oxo-2H-pyridin-1-yl]-3,5-difluorophenoxy}propyl ester

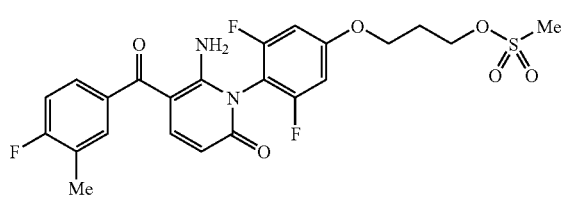

LCMS purity 51%, m/z 511 [M+H]+.

Intermediate 4E Methanesulfonic acid 3-{4-[6-amino-5-(4-fluorobenzoyl)-2-oxo-2H-pyridin-1-yl]-3,5-difluorophenoxy}-propyl ester

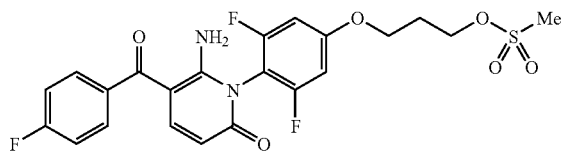

LCMS purity 72%, m/z 497 [M+H]+.

Intermediate 4F Methanesulfonic acid 3-{4-[6-amino-5-(2,4-difluorobenzoyl)-2-oxo-2H-pyridin-1-yl]-3,5-difluorophenoxy}propyl ester

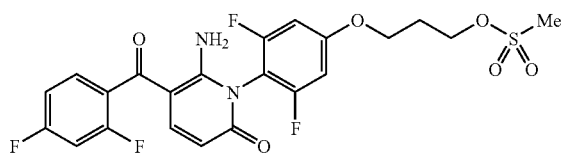

LCMS purity 81%, m/z 515 [M+H]+.

The following intermediates were prepared by direct alkylation of the 4-hydroxyphenyl intermediates (described within WO03/076405) with 1-bromo-5-chloropentane.

Intermediate 4G 6-Amino-1-{4-[(5-chloropentyl)oxy]-2,6-difluorophenyl}-5-(2,4-difluoro-benzoyl)pyridin-2(1H)-one

To a solution of 6-amino-5-(2,4-difluorobenzoyl)-1-(2,6-difluoro-4-hydroxyphenyl)-pyridin-2(1H)-one (300 mg, 0.79 mmol) in acetone (6 ml) under an atmosphere of nitrogen was added 1-bromo-5-chloropentane (0.115 ml, 0.87 mmol, 1.1 eq), sodium iodide (238 mg, 1.59 mmol, 2 eq) and potassium carbonate (438 mg, 3.17 mmol, 4 eq). The mixture was heated at 70° C. for 16 hours, before being allowed to cool to room temperature and partitioned between EtOAc (50 ml) and water (50 ml). The organic layer was dried over MgSO4, filtered and concentrated under reduced pressure. Purification by column chromatography (30% EtOAc in heptane) afforded a 3:2 mixture of the title compound and 6-amino-1-{4-[(5-iodopentyl)oxy]-2,6-difluorophenyl}-5-(2,4-difluorobenzoyl)pyridin-2(1H)-one (142 mg) which was used without further purification.

LC/MS: m/z 483, 575 [M+H]+.

Intermediate 4H 6-Amino-1-[4-[(5-chloropentyl)oxy]-2,6-difluorophenyl]-5-(4-fluoro-benzoyl)pyridin-2(1H)-one

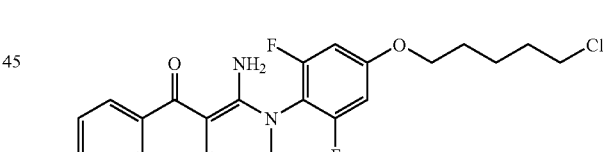

To a solution of 6-amino-5-(2,4-fluorobenzoyl)-1-(2,6-difluoro-4-hydroxyphenyl)-pyridin-2(1H)-one (200 mg, 0.56 mmol) in anhydrous DMF (6 ml) under an atmosphere of nitrogen was added 1-bromo-5-chloropentane (0.088 ml, 0.67 mmol, 1.2 eq) and potassium carbonate (115 mg, 0.83 mmol, 1.5 eq). The mixture was heated at 40° C. for 19 hours, before being allowed to cool to room temperature and diluted with EtOAc (20 ml). The solution was washed with water (3×20 ml) and brine (20 ml). The organic layer was dried over MgSO4, filtered and concentrated under reduced pressure. Purification by column chromatography (20-40% EtOAc in heptane) afforded the title compound as a yellow solid (104 mg) which was used without further purification.

LC/MS: m/z 465 [M+H]+. 1H NMR (300 MHz, CD3OD) δ: 7.60 (2H, m), 7.53 (1H, d, J=9.4 Hz), 7.33 (2H, m), 7.05 (2H, m), 5.72 (1H, d, J=9.8 Hz), 4.11 (2H, t, J=6.3 Hz), 3.68 (2H, t, J=6.5 Hz), 1.84-1.77 (4H, m), 1.56 (2H, m).

Intermediate 4J Methanesulfonic acid 2-{4-[6-amino-5-(4-fluoro-benzoyl)-2-oxo-2H-pyridin-1-yl]-phenyl}-ethyl ester

To a suspension of 6-Amino-5-(4-fluoro-3-methyl-benzoyl)-1-[4-(2-hydroxy-ethyl)-phenyl]-1H-pyridin-2-one (150 mg, 0.43 mmol) in anhydrous DCM (3 ml) at 0° C. was added methanesulfonyl chloride (34 µl, 0.47 mmol) followed by Et₃N (120 µl, 0.85 mmol). The reaction mixture was allowed to warm up to RT and stirred for 24 hours to completion. The reaction mixture was diluted with DCM (10 ml), washed with 10% citric acid (5 ml), followed by sat aq NaHCO₃ (5 ml) and water (5 ml). The DCM layer was dried (MgSO₄), filtered and concentrated in vacuo. Yield=183 mg (crude). LCMS purity=85% m/z=431 [M+H]⁺. This material was used in the next step without further purification. The alcohol used as starting material was prepared as follows:

Acetic acid 2-{4-[6-amino-5-(4-fluoro-benzoyl)-2-oxo-2H-pyridin-1-yl]-phenyl}-ethyl ester (300 mg) was dissolved in water (5 ml) and conc HCl (5 ml) and heated to 100° C. for 1 hour. The reaction was then cooled, diluted with 10 ml water and filtered. The resulting solid was then dried under reduced pressure to give 264 mg of product, m/z=353 [M+H]⁺.

The acetic acid 2-{4-[6-amino-5-(4-fluoro-benzoyl)-2-oxo-2H-pyridin-1-yl]-phenyl}-ethyl ester used as starting material was prepared as follows:

A solution of propionic acid (270 µl, 4.39 mmol) and CDI (712 mg, 4.34 mmol) in THF (13 ml) was warmed from 0° C. to RT and stirred for 1.5 hours. To this solution was added acetic acid 2-(4-{[3-(4-fluoro-phenyl)-3-oxo-propionimidoyl]-amino}-phenyl)-ethyl ester (1 g, 2.92 mmol) in THF (6 ml) and the reaction heated to 80° C. for a period of 2 hours maximum. After cooling and evaporation under reduced pressure, the crude residue was sonicated with methanol (7 ml) before filtration, washing with a minimum amount of methanol. An off-white solid was collected (350 mg crude).

The acetic acid 2-(4-{[3-(4-fluoro-phenyl)-3-oxo-propionimidoyl]-amino}-phenyl)-ethyl ester used as starting material was prepared as follows:

3-(4-Fluoro-phenyl)-3-oxo-thiopropionimidic acid 4-chloro-phenyl ester (1 g, 2.9 mmol) and 4-aminophenethyl alcohol (418 mg, 3.08 mmol) were dissolved in acetic acid (5 ml) and heated to 80° C. for a period of 24 hours. The reaction was cooled to RT and evaporated under reduced pressure. The crude residue was partitioned between DCM and Na₂CO₃. The DCM layer was further washed with brine and dried over MgSO₄ before evaporation under reduced pressure. The product was isolated (1 g crude) as a 3:1 mixture of the acetylated product: alcohol. This was taken through unpurified into the above cyclisation reaction. Product m/z=343 [M+H]⁺, alcohol m/z=301 [M+H]⁺.

Intermediate 5 6-Amino-1-[2,6-difluoro-4-(4-oxo-cyclohexyloxy)phenyl]-5-(4-fluorobenzoyl)-1H-pyridin-2-one

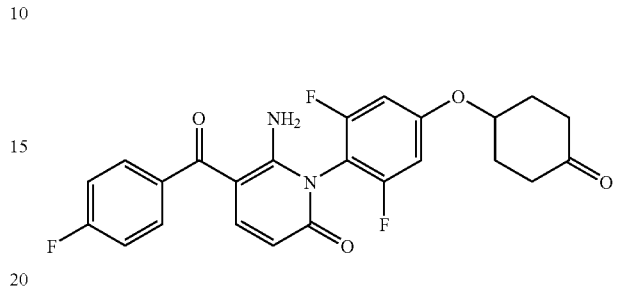

To a solution of 6-amino-1-[4-(1,4-dioxa-spiro[4.5]dec-8-yloxy)-2,6-difluoro-phenyl]-5-(4-fluorobenzoyl)-1H-pyridin-2-one (0.55 g, 1.10 mmol) in 1,4-dioxane (10 ml) was added 2M aq HCl (5 ml) at room temperature. Stirring was continued for 18 h. Upon completion of reaction the reaction mixture was diluted with water (10 ml) before evaporation of dioxane under reduced pressure. The residual aqueous solution was extracted with EtOAc (2×10 ml). The combined organic layers were dried (Na₂SO₄), filtered and concentrated to dryness under reduced pressure to give the desired ketone as a white solid (0.43 g, 86%). LCMS purity 98%, m/z 457 [M+H]⁺, ¹H NMR (400 MHz, CDCl₃), δ: 2.05-2.15 (2H, m), 2.25-2.45 (4H, m), 2.55-2.70 (2H, m), 4.65-4.75 (1H, m), 5.85 (1H, d), 6.70-6.75 (2H, m), 7.05-7.15 (2H, m), 7.50-7.65 (3H, m), The ketal used as starting material was prepared as follows:

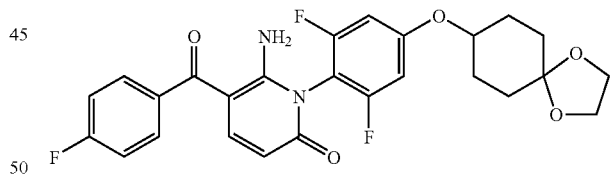

To a stirred solution of 1,4-dioxa-spiro[4.5]decan-8-ol (0.5 g, 1.45 mmol) in THF (1.5 ml) was added 6-Amino-1-(2,6-difluoro-4-hydroxyphenyl)-5-(4-fluoro-benzoyl)-1H-pyridin-2-one (prepared by methods described in WO 03/076405) (0.5 g, 1.39 mmol) and triphenylphosphine (0.38 g, 1.45 mmol) at RT. Diisopropyl azodicarboxylate (0.29 ml, 1.45 mmol) was added dropwise and stirring was continued for 18 h. The reaction mixture was evaporated to dryness and purified by column chromatography to afford the desired material as a white solid (0.55 g, 79%). LCMS purity 99%, m/z 501 [M+H]⁺, ¹H NMR (400 MHz, CDCl₃), δ: 1.55-1.65 (2H, m), 1.75-2.00 (6H, m), 3.85-3.90 (4H, m,), 4.35-4.40 (1H, m), 5.85 (1H, d), 6.10-6.20 (2H, m), 7.05-7.15 (2H, m), 7.45-7.60 (3H, m).

Intermediate 6 6-Amino-5-(4-fluorobenzoyl)-1-(4-oxo-cyclohexyl)-1H-pyridin-2-one

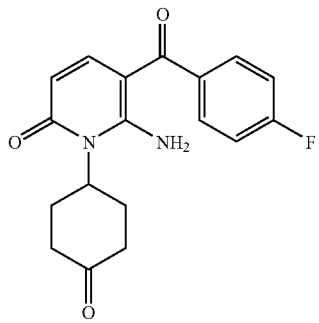

2M HCl (14 ml) was added to a yellow solution of 6-Amino-1-(1,4-dioxa-spiro[4.5]dec-8-yl)-5-(4-fluorobenzoyl)-1H-pyridin-2-one (664 mg, 1.78 mmol) in 1,4-dioxane (60 ml) at RT. The resultant yellow solution was stirred at RT for 24 h and then diluted with H$_2$O (30 ml) and concentrated in vacuo to remove the 1,4-dioxane giving a yellow crystalline solid. The solid was isolated by filtration, washed with H$_2$O and air dried giving a yellow crystalline solid. Yield=479 mg, 82%. LCMS purity 92%, m/z 329 [M+H]$^+$, $^1$H NMR (400 MHz, CDCl$_3$), δ: 1.90-2.30 (8H, m), 5.35 (1H, m), 5.65 (1H, d), 7.05-7.15 (2H, m), 7.30 (1H, d), 7.35-7.45 (2H, m), 11.45 (1H, s).

The pyridone acetal used as starting material in the above procedure was prepared as follows

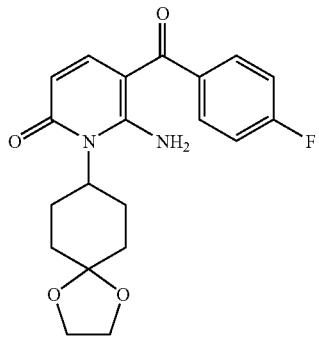

Triethylamine was added (0.74 ml, 5.31 mmol) to a solution of 1-(1,4-Dioxa-spiro[4.5]dec-8-yl)-6-ethanesulfinyl-5-(4-fluorobenzoyl)-1H-pyridin-2-one (1.046 g, 2.42 mmol) in 0.5M NH$_3$ in 1,4-dioxane (30 ml) at RT under N$_2$. The resultant yellow solution was stirred at RT overnight and then concentrated in vacuo giving a yellow solid, which was triturated with TBME, isolated by filtration and washed with TBME giving a pale yellow solid. Yield=802 mg, 89%. LCMS purity 100%, m/z 373 [M+H]$^+$, $^1$H NMR (400 MHz, CDCl$_3$), δ: 1.90-2.00 (6H, m), 2.60 (2H, m), 4.15 (4H, m), 5.90 (1H, d), 7.25 (2H, m), 7.55 (1H, d), 7.65 (2H, m).

The sulphoxide used in the above procedure was prepared as follows

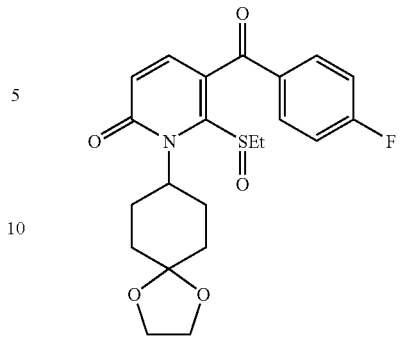

m-Chloroperbenzoic acid (583 mg, 2.60 mmol) was added in one portion to a yellow solution of 1-(1,4-Dioxaspiro[4.5]dec-8-yl)-6-ethylsulfanyl-5-(4-fluorobenzoyl)-1H-pyridin-2-one (986 mg, 2.36 mmol) in CH$_2$Cl$_2$ (30 ml) at RT under N$_2$. The resultant yellow solution was stirred at RT overnight and then diluted with CH$_2$Cl$_2$ (25 ml) and washed with sat. Na$_2$SO$_3$ (2×30 ml), sat. NaHCO$_3$ (2×30 ml), H$_2$O (30 ml), dried (Na$_2$SO$_4$), filtered and concentrated in vacuo giving a light yellow oil. Yield=1.046 g, 102%. LCMS purity 96%, m/z 434 [M+H]$^+$.

The sulphide used in the procedure above was prepared as follows

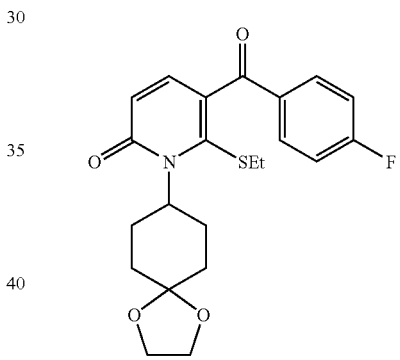

1-Chloro-N,N$^2$-trimethylpropenylamine (2.03 ml, 15.34 mmol) was added to a colourless solution of propionic acid (0.94 ml, 15.34 mmol) in anhydrous THF (50 ml) at 0° C. under N$_2$. The resultant colourless solution was stirred at 0° C. for 2 h after which time a yellow solution of the N-(1,4-Dioxa-spiro[4.5]dec-8-yl)-3-(4-fluorophenyl)-3-oxo-thiopropionimidic acid (4.667 g, 12.79 mmol) in anhydrous THF (50 ml) was added over 5 min at 0° C. The resultant yellow solution was then allowed to warm to RT and stirred for 24 h. The reaction mixture was concentrated in vacuo giving a dark brown oil, which was diluted with EtOAc (20 ml) and allowed to stand at RT overnight giving a crystalline solid which was isolated by filtration and washed with heptane and TBME. Yield=216 mg. The filtrate was concentrated in vacuo giving a brown solid which was dissolved in CH$_2$Cl$_2$ (100 ml) and washed with sat. Na$_2$CO$_3$ (3×100 ml), H$_2$O (2×100 ml), dried (Na$_2$SO$_4$), filtered and concentrated in vacuo giving a brown oil. Purification by flash column chromatography (silica, 100% CH$_2$Cl$_2$ to 30% EtOAc/CH$_2$Cl$_2$) gave the cyclised product after trituration with TBME. Yield=770 mg. Overall yield=986 mg, 19%. LCMS purity 100%, m/z 418 [M+H]$^+$.

The thiopropionimidic acid used in the above procedure was prepared as follows:

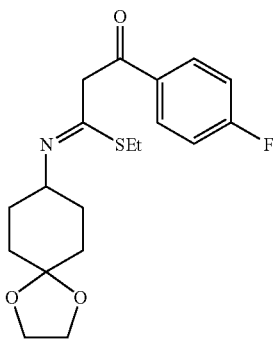

K$_2$CO$_3$ (16.1 g, 117 mmol) was added to a solution of N-(1,4-Dioxaspiro[4.5]dec-8-yl)-3-(4-fluorophenyl)-3-oxo-thiopropionamide (18.8 g, 55.7 mmol) in acetone (200 ml) at RT/N$_2$ followed by the ethyl iodide (6.68 ml, 83.6 mmol). The reaction mixture was stirred at RT/N$_2$ for 2 h and then concentrated in vacuo giving a brown paste which was taken up in EtOAc (300 ml) and washed with H$_2$O (250 ml). The organic phase was separated and the aqueous phase was extracted with EtOAc (2×150 ml). The combined organic phases were dried (Na$_2$SO$_4$), filtered and concentrated in vacuo a brown oil. Purification by flash column chromatography (silica, 15% EtOAc/Heptane) gave a yellow oil. Yield=9.94 g, 49%. LCMS purity 94%, m/z 366 [M+H]$^+$.

The thiopropionamide used in the above process was prepared as follows:

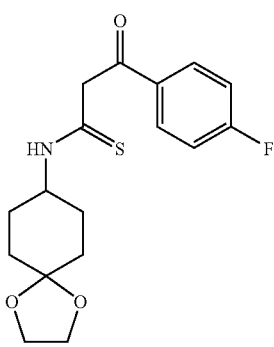

A solution of 4-fluoroacetophenone (6.76 ml, 55.7 mmol) in THF (50 ml) was added slowly over 5 min to a stirred suspension of KO$^t$Bu (6.56 g, 58.5 mmol) in THF (40 ml) at 0° C. A solution of 8-isothiocyanato-1,4-dioxaspiro[4.5]decane (11.1 g, 55.7 mmol) in THF (30 ml) was added at 0° C. over 5 min and the resulting mixture was stirred at 0° C. for 90 min. The reaction mixture was evaporated to dryness giving a dark brown solid which was used crude in the next stage. Yield=18.8 g, 100%. LCMS purity 55%, m/z 338 [M+H]$^+$.

The isothiocyanate used in the above procedure was prepared as follows

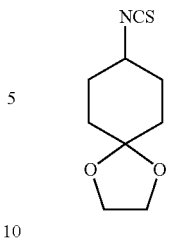

Calcium carbonate (13.75 g, 137.4 mmol) was added to a solution of 1,4-dioxaspiro[4.5]dec-8-ylamine (13.5 g, 85.9 mmol) in CH$_2$Cl$_2$ (675 ml) and H$_2$O (330 ml) with vigorous stirring at RT. The thiophosgene (8.5 ml, 111.6 mmol) was added dropwise over 5 min and upon complete addition the reaction mixture was stirred at RT for 2 h. The reaction mixture was diluted with H$_2$O (600 ml) and extracted into CH$_2$Cl$_2$ (300 ml). The organic phase was dried (Na$_2$SO$_4$), filtered and concentrated in vacuo giving the product. Yield=8.5 g, 50%. LCMS purity 47%, m/z 200 [M+H]$^+$.

The cyclohexylamine used in the above process was prepared as follows:

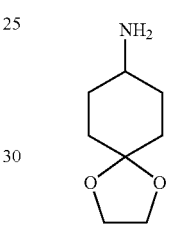

10% Pd(OH)$_2$/C (1 g) was added to a fine suspension of N,N-dibenzyl-N-1,4-dioxaspiro[4.5]dec-8-ylamine (21.13 g, 62.7 mmol) in EtOH (400 ml) at RT. The resultant mixture was evacuated and purged three times with H$_2$ and then held under an atmosphere of H$_2$ (balloon) overnight. The reaction mixture was evacuated and purged three times with N$_2$ and then the catalyst was removed by filtration. The filtrate was concentrated in vacuo giving the amine as a colourless oil. Yield=14.34 g, 99%. LC-MS (ELS detection) purity 100%, m/z 158 [M+H]$^+$.

The dibenzylamine used in the above process was prepared as follows:

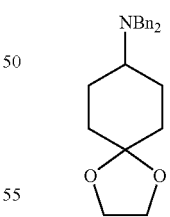

Dibenzylamine (27.8 ml, 145 mmol) was added to a solution of 1,4-dioxaspiro[4.5]decan-8-one (21.5 g, 138 mmol) in DCE (350 ml) at RT under N$_2$ and stirred for 1 h. Sodium triacetoxyborohydride (46.7 g, 220 mmol) was added portion wise over 10 min and upon complete addition the reaction was stirred at RT/N$_2$ overnight. Saturated NaHCO$_3$ (300 ml) was added followed by DCM (300 ml) and the reaction mixture was stirred for 30 min. The organic phase was separated and washed with NaHCO$_3$ (300 ml), brine (300 ml), dried (Na$_2$SO$_4$), filtered and concentrated in vacuo giving an oil which upon trituration with heptane gave a white solid which was isolated by filtration. Yield=30.95 g, 67%. LCMS purity 100%, m/z 338 [M+H]+.

Intermediate 7 Cyclopentyl(S)-2-(tert-Butoxycarbonyl-{3,5-difluoro-4-[3-(4-fluoro-benzoyl)-6-oxo-1,6-dihydropyridin-2-ylamino]benzyl}amino)-3-phenyl propionate

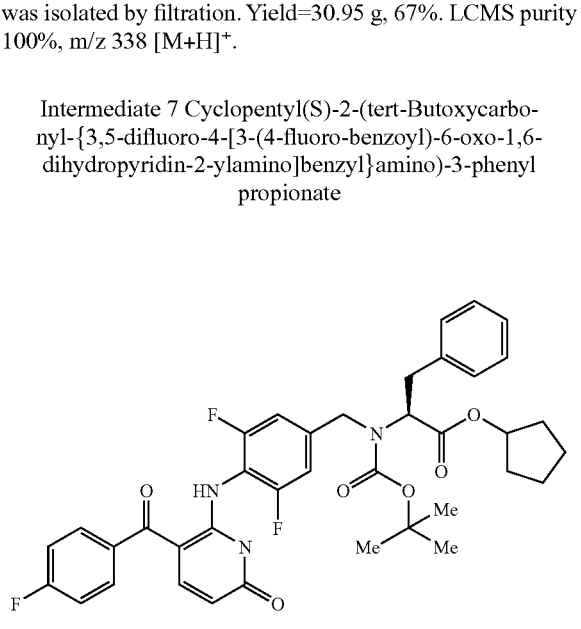

The pyridone was formed as a side product of the procedure described for the synthesis of Intermediate 3K. LCMS purity 80%, m/z 690 [M+H]+.

Preparation of Aminoacid Esters
(Intermediates 8 to 16)

Route I. Used for the Preparation of Intermediates 8, 9, 13, 14 and 15

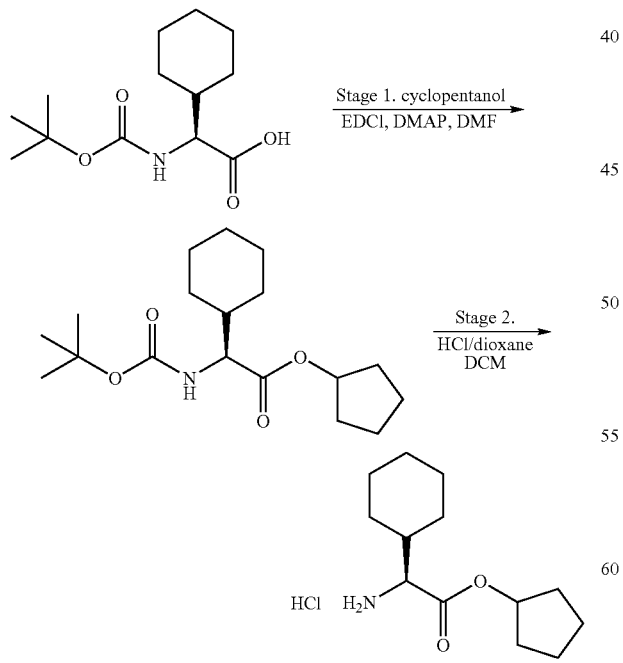

Route II. Used for the Preparation of Intermediate 10, 11, 12 and 16

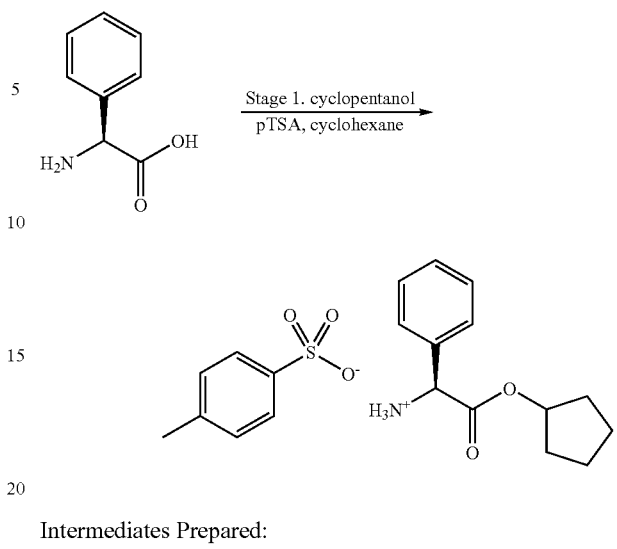

Intermediates Prepared:

FIG. 1

Intermediate 8

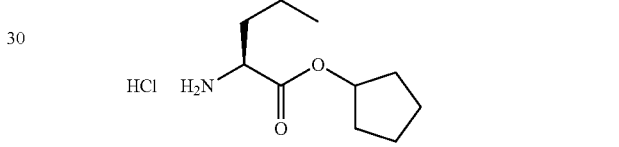

Intermediate 9

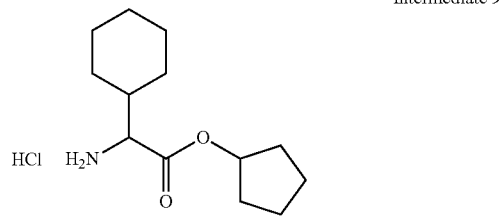

Intermediate 10

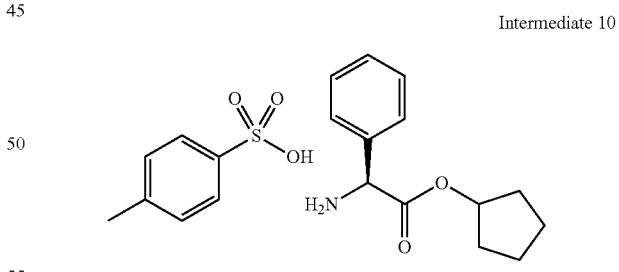

Intermediate 11

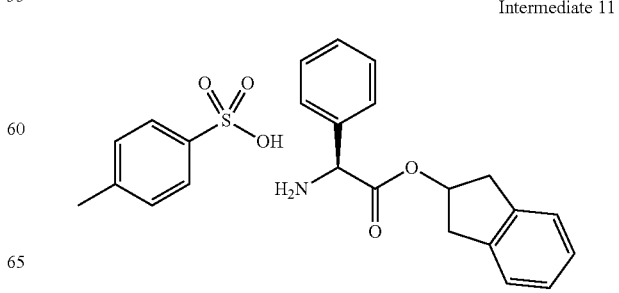

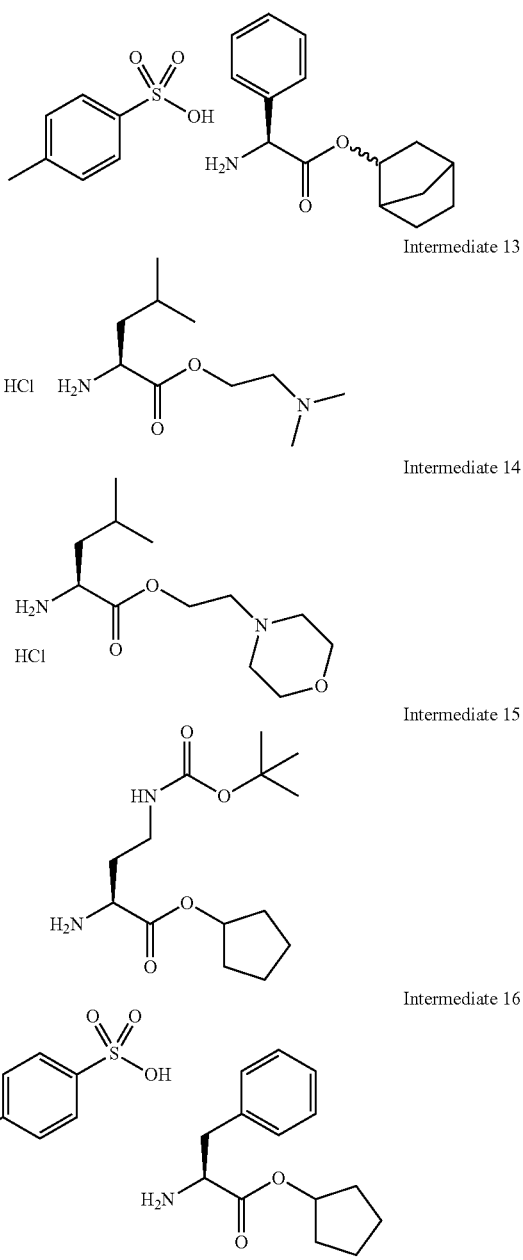

Intermediate 12

Intermediate 13

Intermediate 14

Intermediate 15

Intermediate 16

Synthesis of Compounds Outlined in FIG. 1
Route I (Exemplified for Intermediate 9)

Stage 1—Ester Formation

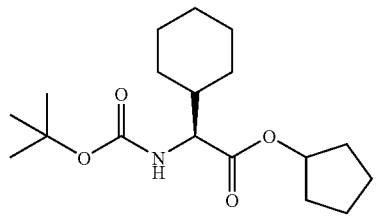

To a solution of (S)-2-tert-butoxycarbonylamino-3-cyclohexyl-propionic acid (5 g, 19.4 mmol) in DMF (50 ml) at 0° C. was added cyclopentanol (8.8 ml, 97.15 mmol), EDCI (4.09 g, 21.37 mmol) and finally DMAP (237 mg, 1.94 mmol). The reaction mixture was warmed to RT and stirred for 18 h. The DMF was removed in vacuo to give a clear oil. This was separated between water and EtOAc. The organic phase was dried (MgSO$_4$) and concentrated in vacuo. The crude extract was purified by column chromatography (25% EtOAC in heptane) to yield the desired product as a clear oil (14.87 g, 55%). $^1$H NMR (300 MHz, d$_6$-DMSO) δ; 7.09 (1H, d), 5.08 (1H, t), 3.76 (1H, t), 1.50-1.85 (10H, br m), 1.39 (9H, s), 1.00-1.25 (9H, br m).

Stage 2—Boc Deprotection to Yield
Cyclopentyl(2S)-amino(cyclohexyl)acetate
hydrochloride (Intermediate 9)

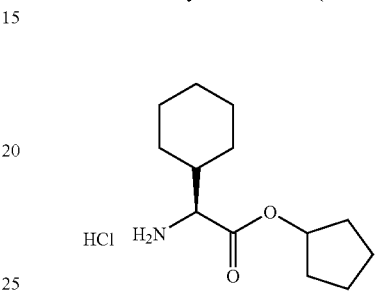

Stage 1 product (14.87 g, 45.69 mmol) was dissolved in DCM (100 ml) and treated with 4M HCl/dioxane (22.8 ml, 91.38 mmol) and the reaction mixture was stirred at RT for 24 h. The crude mixture was concentrated under reduced pressure to give an orange oil. This was triturated with Et$_2$O to give a white precipitate. This was further washed with Et$_2$O to give the desired product as a white powder (7.78 g, 65%). $^1$H NMR (300 MHz, d$_6$-DMSO) δ; 8.45 (3H, br s), 5.22 (1H, t), 3.28 (1H, d), 1.95-1.50 (10H, br m), 1.30-0.90 (9H, br m).
Route II (Exemplified for Intermediate 10)

Stage 1—Ester Formation to Yield (1S)-2-(cyclopentyloxy)-2-oxo-1-phenylethanaminium 4-methylbenzenesulfonate (Intermediate 10)

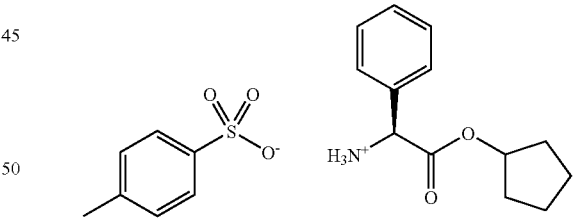

To a slurry of (S)-phenylglycine (5 g, 33.1 mmol) in cyclohexane (150 ml) was added cyclopentanol (29.84 ml, 331 mmol) and p-toluene sulfonic acid (6.92 g, 36.4 mmol). The reaction was fitted with a Dean-Stark receiver and heated to 135° C. for complete dissolution. After 12 h, the reaction was cooled to RT leading to the precipitation of a white solid. The solid was filtered and washed with EtOAc before drying under reduced pressure to give the required product as a white powder (11.01 g, 85%). $^1$H NMR (300 MHz, d$_6$-DMSO) δ; 8.82 (2H, br s), 8.73 (1H, br s), 7.47 (7H, m), 7.11 (2H, d), 5.25 (1H, br s), 5.18 (1H, m), 2.29 (3H, s), 1.87-1.36 (8H, m).

Intermediates 11 and 12 were prepared using 2-indanol and α-norborneol respectively, instead of cyclopentanol (via Route II). In a similar manner, intermediates 13 and 14 were prepared using dimethylaminoethanol and 4-(2-hydroxyethyl)-morpholine respectively (via Route I). Intermediate 15 was prepared via route I using commercially available Z-Dab (Boc)-OH(N-α-Z—N-γ-Boc-L-2,4-diaminobutyric acid).

The corresponding (R)-amino acid esters of the above intermediates can be prepared in a similar manner to shown above, starting from the relevant commercially available (R)-amino acids. In addition, the corresponding Leucine and Phenylglycine tert-butyl esters are commercially available and are used directly where appropriate.

EXAMPLES

Example 1

Cyclopentyl(S)-{4-[6-Amino-5-(4-fluorobenzoyl)-2-oxo-2H-pyridin-1-yl]benzylamino}phenylacetate

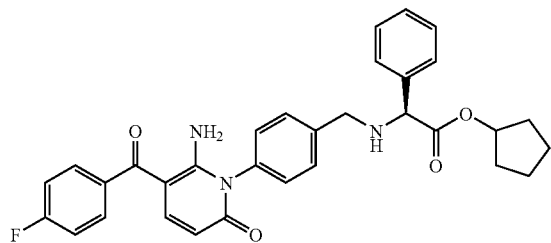

A mixture of Intermediate 3A (80 mg, 0.125 mmol) in 20% TFA/DCM solution (5 ml) was allowed to stir at RT for 1 h. The reaction mixture was evaporated to dryness and purified by preparative HPLC to give the desired product, yield=33 mg (40%), LCMS purity=100% m/z 540 [M+H]$^+$, $^1$H NMR (400 MHz, DMSO), δ: 1.21-1.82 (8H, m), 4.01-4.14 (2H, m), 5.11-5.21 (2H, m), 5.64 (1H, d), 7.21-7.54 (13H, m), 7.62 (1H, d), 10.16 (2H, br s).

The following examples were prepared in a similar manner to Example 1.

Example 2

Cyclopentyl(S)-2-{4-[6-Amino-5-(4-fluorobenzoyl)-2-oxo-2H-pyridin-1-yl]benzylamino}-3-phenylpropionate

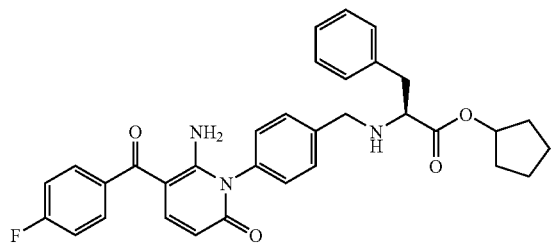

From the Intermediate 3D. LCMS purity 100%, m/z 554 [M+H]$^+$, $^1$H NMR (400 MHz, DMSO), δ: 1.22-1.83 (8H, m), 3.10 (1H, m), 4.45 (3H, m), 5.19 (1H, m), 5.85 (1H, d), 7.35-7.74 (14H, m), 7.82 (1H, br s), 9.96 (1H, br s).

Example 3

Cyclopentyl(S)-2-{4-[6-Amino-5-(4-fluorobenzoyl)-2-oxo-2H-pyridin-1-yl]benzylamino}-4-methylpentanoate

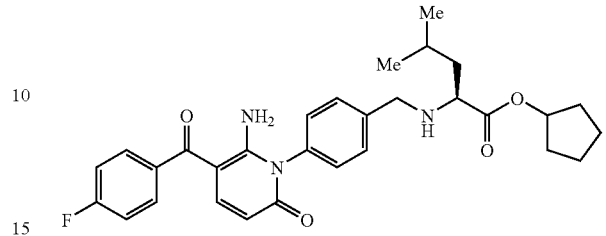

From Intermediate 3G. LCMS purity 100%, m/z 520 [M+H]$^+$, $^1$H NMR (400 MHz, DMSO), δ: 1.10 (6H, m), 1.70-2.11 (11H, m), 4.14-4.53 (3H, m), 5.42 (1H, m, CH), 5.90 (1H, d), 7.49-7.91 (9H, m), 9.83 (2H, br s).

Example 4

Cyclopentyl(S)-{4-[6-Amino-5-(3-methyl-4-fluorobenzoyl)-2-oxo-2H-pyridin-1-yl]benzylamino}phenylacetate

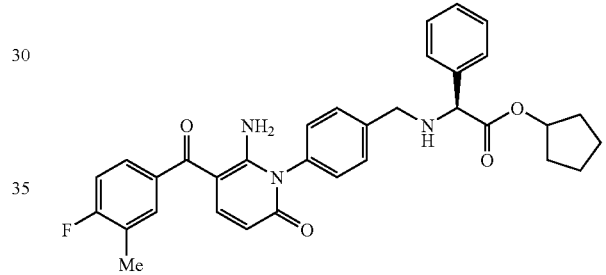

From Intermediate 3C, LCMS purity 97%, m/z 554 [M+H]$^+$, $^1$H NMR (400 MHz, CD$_3$OD), δ: 1.30-1.81 (8H, m), 2.25 (3H, s), 3.72 (2H, s), 4.34 (1H, s), 5.08 (1H, m), 5.70 (1H, d), 7.03-7.38 (10H, m), 7.46-7.61 (3H, m).

Example 5

Cyclopentyl(S)-2-{4-[6-Amino-5-(3-methyl-4-fluorobenzoyl)-2-oxo-2H-pyridin-1-yl]benzylamino}-3-phenylpropionate

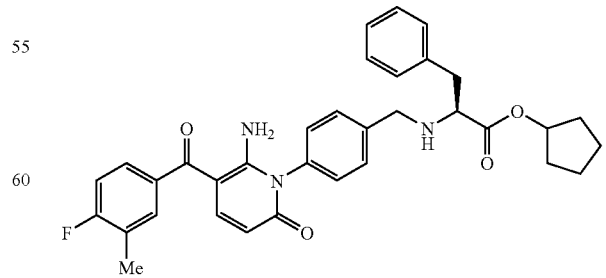

From Intermediate 3F. LCMS purity 100%, m/z 568 [M+H]$^+$, $^1$H NMR (400 MHz, DMSO), δ: 1.09-1.77 (8H, m), 2.30 (3H, s), 2.95 (1H, m), 3.14 (2H, s), 4.19-4.42 (3H, m), 5.02 (1H, m), 5.69 (1H, d), 7.19-7.51 (11H, m), 7.68 (2H, m), 9.79 (2H, br s).

Example 6

Cyclopentyl(S)-2-{4-[6-Amino-5-(3-Methyl-4-fluorobenzoyl)-2-oxo-2H-pyridin-1-yl]benzylamino}-4-methylpentanoate

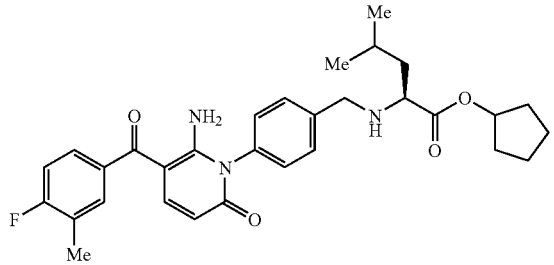

From Intermediate 3J. LCMS purity 100%, m/z 534 [M+H]+, 1H NMR (400 MHz, DMSO), δ: 0.71 (6H, m), 1.32-1.70 (11H, m), 2.09 (3H, s), 3.72-4.14 (3H, m), 5.03 (1H, m), 5.50 (1H, d), 7.00-7.29 (6H, m), 7.46 (2H, m), 9.40 (2H, br s).

Example 7

Cyclopentyl(S)-{4-[6-Amino-5-(2,4-difluorobenzoyl)-2-oxo-2H-pyridin-1-yl]benzylamino}phenylacetate

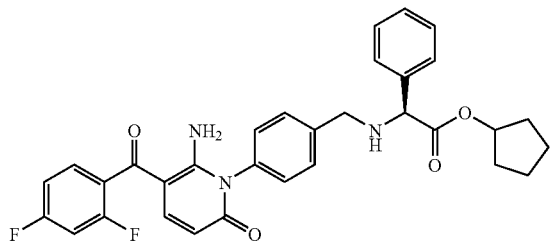

From Intermediate 3B. LCMS purity 100%, m/z 558 [M+H]+, 1H NMR (400 MHz, DMSO), δ: 1.33-1.89 (8H, m), 3.71 (2H, m), 4.28 (1H, s), 5.04 (1H, m), 5.61 (1H, d), 6.91 (1H, br s), 7.18-7.60 (13H, m), 10.05 (1H, br s).

Example 8

Cyclopentyl(S)-2-{4-[6-Amino-5-(2,4-difluorobenzoyl)-2-oxo-2H-pyridin-1-yl]benzylamino}-3-phenylpropionate

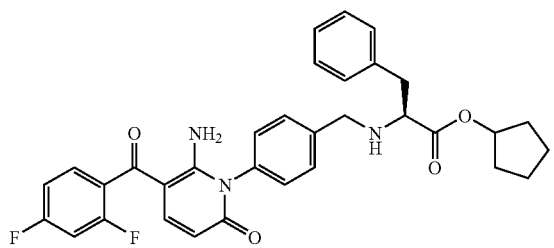

From Intermediate 3E. LCMS purity 100%, m/z 572 [M+H]+, 1H NMR (400 MHz, DMSO), δ: 1.08-1.76 (8H, m), 2.95 (1H, t), 4.11-4.40 (3H, m), 4.98 (1H, m), 5.68 (1H, d), 6.89 (1H, br s), 7.13-7.50 (12H, m), 7.65 (1H, m), 9.64-10.12 (2H, br s).

Example 9

Cyclopentyl(S)-2-{4-[6-Amino-5-(2,4-difluorobenzoyl)-2-oxo-2H-pyridin-1-yl]benzylamino}-4-methylpentanoate

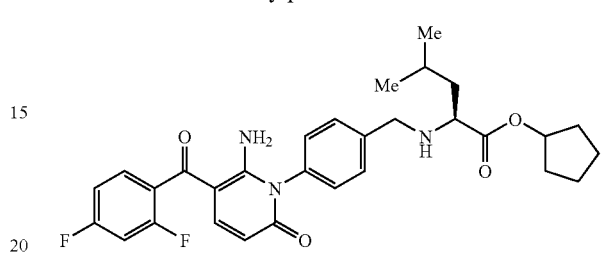

From Intermediate 3I. LCMS purity 100%, m/z 538 [M+H]+, 1H NMR (400 MHz, DMSO), δ: 0.79 (6H, m), 1.39-1.78 (11H, m), 3.84-4.22 (3H, m), 5.10 (1H, m), 5.59 (1H, d), 6.79 (1H, br s), 7.03-7.18 (2H, m), 7.21-7.42 (4H, m), 7.56 (2H, m), 9.54 (1H, br s), 9.92 (1H, br s).

Example 10

Cyclopentyl(S)-2-{4-[6-Amino-5-(2,4-fluorobenzoyl)-2-oxo-2H-pyridin-1-yl]-3,5-difluorobenzylamino}-3-phenylpropionate

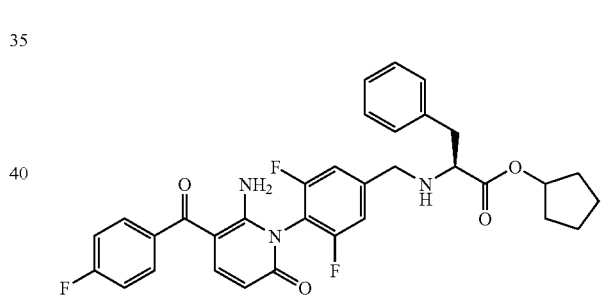

From Intermediate 3K. LCMS purity 94%, m/z 591 [M+H]+, 1H NMR (400 MHz, d6-DMSO), δ: 1.20-1.90 (10H, m), 3.10 (1H, m), 3.50-3.60 (2H, m), 4.40-4.50 (4H, m), 5.20 (1H, m), 5.90 (1H, d), 7.35-7.50 (7H, m), 7.65-7.70 (5H, m), 9.50 (1H, br)

Example 11

Cyclopentyl(S)-2-{4-[6-Amino-5-(4-fluorobenzoyl)-2-oxo-2H-pyridin-1-yl]-3,5-difluorobenzylamino}-4-methylpentanoate

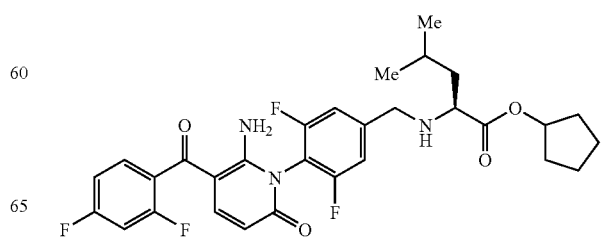

From Intermediate 3L. LCMS purity 96%, m/z 574 [M+H]+, 1H NMR (400 MHz, CD3OD), δ: 0.95-1.15 (6H, m), 1.65-2.05 (11H, m), 4.15-4.25 (1H, m), 4.35-4.45 (2H, m), 5.35-5.45 (1H, m), 5.85 (1H, d), 7.10-7.20 (2H, m), 7.45-7.55 (4H, m).

Example 12

Cyclopentyl(S)-2-(3-{4-[6-Amino-5-(3-methyl-4-fluoro benzoyl)-2-oxo-2H-pyridin-1-yl]phenoxy}propylamino)-3-phenyl propionate

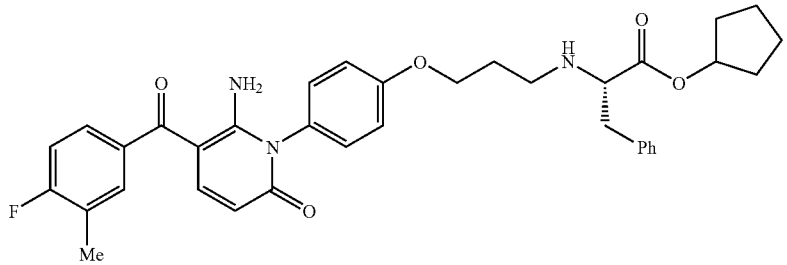

To a mixture of L-phenylalanine cyclopentyl ester tosylate salt (Intermediate 16) (218 mg, 0.54 mmol), K2CO3 (192 mg, 1.39 mmol), NaI (108 mg, 0.72 mmol) was added a solution of mesylate Intermediate 4A (170 mg, 0.35 mmol) in THF (2 ml). The reaction mixture was diluted with DMF (2 ml) and heated at 70° C. for 18 h with stirring. The reaction mixture was cooled to RT, THF was removed by concentration under reduced pressure. The residue was diluted with EtOAc (20 ml) and washed with water (10 ml), dried (Na2SO4), filtered and evaporated to dryness. Purification by preparative HPLC afforded the desired product, yield=57 mg, 15%. LCMS purity 97%, m/z 612 [M+H]+, 1H NMR (400 MHz, CD3OD), δ: 1.30-2.00 (8H, m), 2.30 (2H, m), 3.10 (1H, m), 3.40 (1H, m), 4.25 (2H, m), 4.40 (1H, m), 5.20 (1H, m), 5.85 (1H, d), 6.90 (2H, m), 7.10 (2H, d), 7.20-7.45 (7H, m), 7.65 (2H, m), 7.75 (1H, m).

The following compounds were prepared in a similar manner

Example 13

Cyclopentyl(S)-(3-{4-[6-Amino-5-(4-fluorobenzoyl)-2-oxo-2H-pyridin-1-yl]-3,5-difluorophenoxy}propylamino)phenylacetate

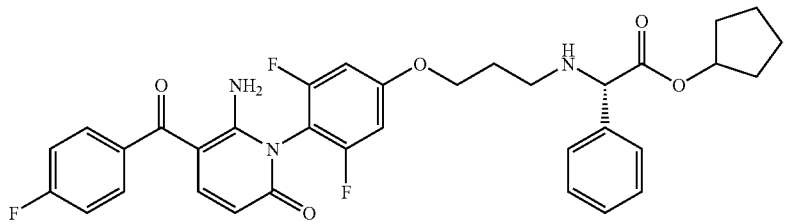

From Intermediate 4E and L-phenylglycine cyclopentyl ester tosylate salt (Intermediate 10), LCMS purity 96%, m/z 620 [M+H]+, 1H NMR (400 MHz, CD3OD), d: 1.40-1.65 (5H, m), 1.80 (2H, m), 1.95 (1H, m), 2.30 (2H, m), 3.15 (1H, m), 3.30 (1H, m), 4.25 (2H, m), 5.25 (1H, s), 5.40 (1H, m), 5.90 (1H, d), 6.90 (2H, d), 7.30 (2H, t), 7.55-7.60 (5H, m), 7.65 (2H, m) 7.75 (1H, d).

Example 14

Cyclopentyl(S)-(3-{4-[6-Amino-5-(4-fluorobenzoyl)-2-oxo-2H-pyridin-1-yl]-3,5-difluorophenoxy}propylamino)phenylacetate

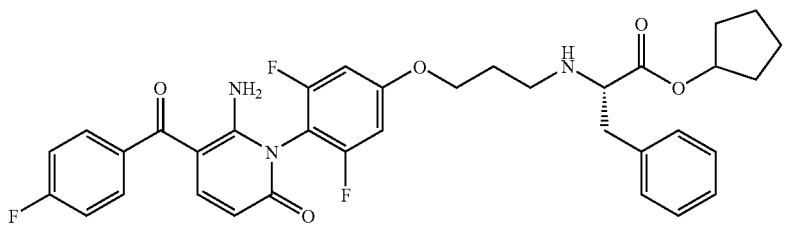

From Intermediate 4E and L-phenylalanine cyclopentyl ester tosylate salt (Intermediate 16), LCMS purity 97%, m/z 634 [M+H]$^+$, $^1$H NMR (400 MHz, CD$_3$OD), δ: 1.30-2.00 (8H, m), 2.30 (2H, m), 3.10 (1H, m), 3.40 (1H, m), 4.25 (2H, m), 4.40 (1H, m), 5.20 (1H, m), 5.85 (1H, d), 6.90 (2H, m), 7.10 (2H, d), 7.20-7.45 (7H, m), 7.65 (2H, m), 7.75 (1H, m).

Example 15

Cyclopentyl(S)-2-(3-{4-[6-Amino-5-(4-fluorobenzoyl)-2-oxo-2H-pyridin-1-yl]-3,5-difluorophenoxyphenoxy}propylamino)-4-methyl pentanoate

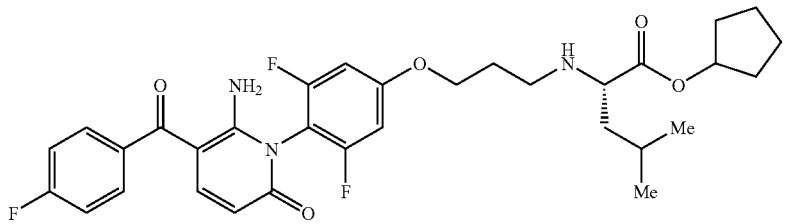

From Intermediate 4E and L-leucine cyclopentyl ester (Intermediate 8), LCMS purity 96%, m/z 600 [M+H]$^+$, $^1$H NMR (400 MHz, CD$_3$OD), δ: 1.10 (6H, m), 1.70-2.0 (12H, m), 2.30 (2H, m), 4.10 (1H, m), 4.25 (2H, m), 4.40 (1H, m), 5.40 (1H, m), 5.85 (1H, d), 6.90 (2H, m). 7.10 (2H, d), 7.60 (2H, m), 7.65 (2H, m), 7.75 (1H, m).

From Intermediate 4E and L-leucine ethyl ester LCMS purity 98%, m/z 560 [M+H]$^+$, $^1$H NMR (400 MHz, CD$_3$OD), δ: 1.10-1.20 (6H, m), 1.45-1.55 (3H, t), 1.65-1.85 (2H, m), 1.90-2.00 (1H, m), 2.15-2.30 (2H, m), 2.85-3.05 (2H, m), 3.55 (1H, m), 4.35-4.50 (4H, m), 6.00 (1H, d), 7.10 (1H, d), 7.45-7.55 (1H, m), 7.80-7.85 (1H, m), 7.95 (1H, d).

Example 16

Ethyl N-(3-{4-[6-amino-5-(4-fluorobenzoyl)-2-oxopyridin-1(2H)-yl]-3,5-difluorophenoxy}propyl)-L-leucinate

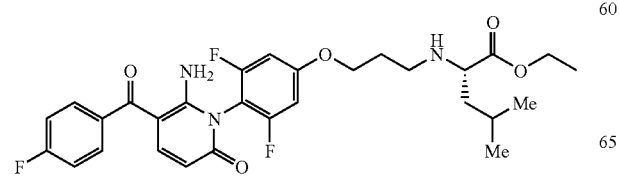

Example 17

Cyclopentyl(S)-(3-{4-[6-Amino-5-(4-fluoro-3-methylbenzoyl)-2-oxo-2H-pyridin-1-yl]-3,5-difluorophenoxy}propylamino) phenylacetate

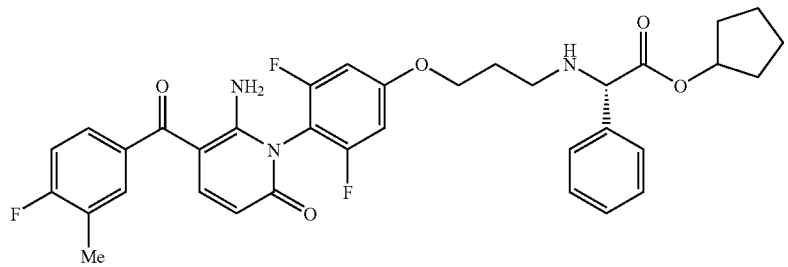

From Intermediate 4D and L-phenylglycine cyclopentyl ester tosylate salt (Intermediate 10), LCMS purity 100%, m/z 634 [M+H]$^+$, $^1$H NMR (400 MHz, d$_6$-DMSO), δ: 1.20-1.80 (8H, m), 2.0 (2H, m), 2.20 (3H, m), 2.80-3.00 (2H, m), 4.10 (2H, m), 5.10 (1H, m), 5.30 (1H, s), 5.60 (1H, d), 6.95 (1H, d), 7.20 (1H, m), 7.30 (1H, m), 7.40-7.50 (8H, m), 9.65 (1H, m).

From Intermediate 4D and L-leucine cyclopentyl ester (Intermediate 8), LCMS purity 100%, m/z 614 [M+H]$^+$, $^1$H NMR (400 MHz, d$_6$-DMSO), δ: 0.90 (6H, m), 1.60-1.70 (10H, m), 1.90 (2H, m), 2.15 (2H, m), 2.30 (3H, s), 3.00-3.20 (2H, m), 4.10 (1H, s), 4.20 (2H, m), 5.25 (1H, m), 5.70 (1H, d), 7.05 (1H, d), 7.25 (1H, m), 7.40 (1H, m), 7.50 (1H, m), 7.60 (1H, d).

Example 18

Cyclopentyl(S)-2-(3-{4-[6-Amino-5-(4-fluoro-3-methylbenzoyl)-2-oxo-2H-pyridin-1-yl]-3,5-difluorophenoxy}propylamino)-3-phenylpropionate

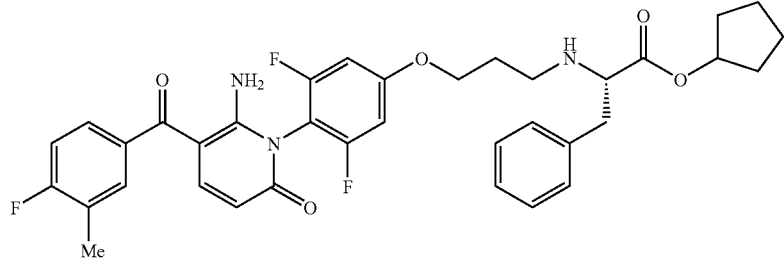

From Intermediate 4D and L-phenylalanine cyclopentyl ester tosylate salt (Intermediate 16), LCMS purity 97%, m/z 648 [M+H]$^+$, $^1$H NMR (400 MHz, CD$_3$OD), δ: 1.20-1.90 (9H, m), 2.25 (2H, m), 2.35 (3H, s), 3.15 (1H, m), 3.45 (1H, m), 4.25 (2H, m), 4.40 (1H, d), 5.20 (2H, m), 5.82 (1H, d), 6.95 (2H, m), 7.20 (1H, m), 7.30-7.50 (7H, m), 7.75 (1H, d).

Example 19

Cyclopentyl(S)-2-(3-{4-[6-Amino-5-(4-fluoro-3-methylbenzoyl)-2-oxo-2H-pyridin-1-yl]-3,5-difluorophenoxy}propylamino)-4-methylpentanoate

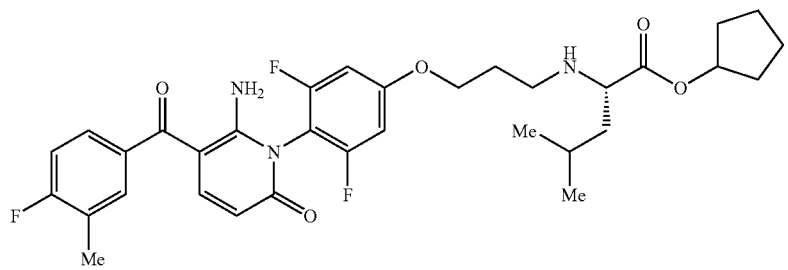

Example 20

Cyclopentyl(S)-(3-{4-[6-Amino-5-(2,4-difluoro benzoyl)-2-oxo-2H-pyridin-1-yl]-3,5-difluorophenoxy}propylamino)phenyl acetate

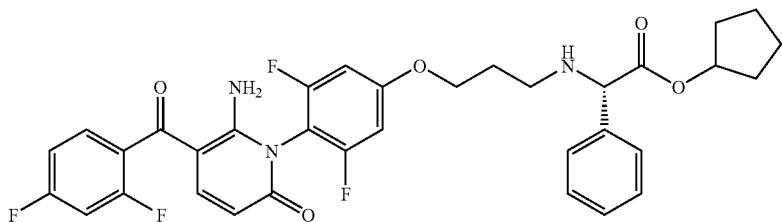

From Intermediate 4F and L-phenylglycine cyclopentyl ester tosylate salt (Intermediate 10), LCMS purity 91%, m/z 638 [M+H]$^+$, $^1$H NMR (400 MHz, d$_6$-DMSO), δ: 1.50-2.10 (8H, m), 2.30 (2H, m), 3.10-3.25 (2H, m), 4.33 (2H, m), 5.40 (1H, m), 5.56 (1H, m), 5.90 (1H, d), 7.20 (1H, d) 7.40-7.75 (9H, m), 9.85 (2H, m).

Example 21

Cyclopentyl(S)-2-(3-{4-[6-Amino-5-(2,4-difluorobenzoyl)-2-oxo-2H-pyridin-1-yl]-3,5-difluorophenoxy}-propylamino)-3-phenyl propionate

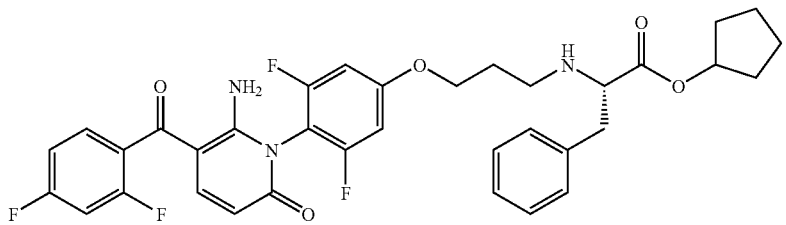

From Intermediate 4F and L-phenylalanine cyclopentyl ester tosylate salt (Intermediate 16). LCMS purity 100%, m/z 652 [M+H]$^+$, $^1$H NMR (400 MHz, d$_6$-DMSO), δ: 1.10-1.80 (9H, m), 2.15 (2H, m), 2.95-3.20 (2H, m), 4.20 (2H, m), 4.40 (1H, m), 5.10 (1H, m), 5.75 (1H, d), 7.06 (2H, d), 7.25-7.58 (9H, m), 9.34 (2H, m).

Example 22

Cyclopentyl(S)-2-(3-{4-[6-Amino-5-(2,4-difluoro benzoyl)-2-oxo-2H-pyridin-1-yl]-3,5-difluorophenoxy}propylamino)-4-methyl pentanoate

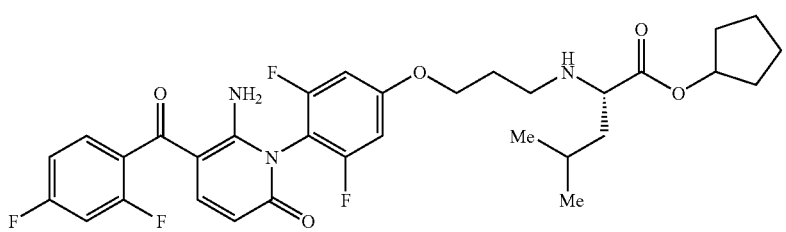

From Intermediate 4F and L-leucine cyclopentyl ester (Intermediate 8), LCMS purity 87%, m/z 618 [M+H]$^+$, $^1$H NMR (400 MHz, d$_6$-DMSO), δ: 1.0 (6H, m), 1.75 (9H, m), 1.95 (2H, m), 2.20 (2H, m), 3.10-3.30 (2H, m), 4.16 (1H, m), 4.26 (2H, m), 5.33 (1H, m), 5.80 (1H, d), 7.15 (2H, d), 7.40-7.65 (4H, m), 9.13-9.25 (2H, m).

Example 23

Cyclopentyl(S)-(3-{4-[6-Amino-5-(4-fluorobenzoyl)-2-oxo-2H-pyridin-1-yl]-phenoxy}propylamino)phenylacetate

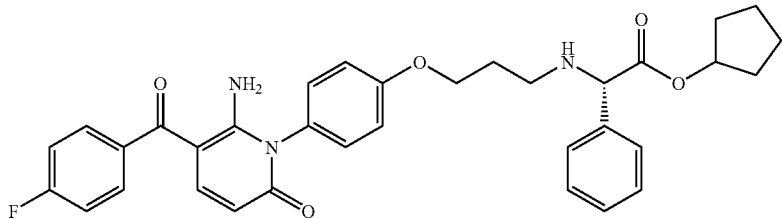

From Intermediate 4B and L-phenylglycine cyclopentyl ester tosylate salt (Intermediate 10), LCMS purity 95%, m/z 584 [M+H]+, 1H NMR (400 MHz, CD3OD), δ: 1.25-1.55 (5H, m), 1.60-1.85 (3H, m), 2.15 (2H, m), 3.00 (1H, m), 3.15 (1H, m), 4.05 (2H, m), 5.10 (1H, s), 5.25 (1H, m), 5.70 (1H, d), 7.00 (2H, m), 7.15 (4H, m), 7.40-7.50 (7H, m), 7.55 (1H, d).

Example 24

Cyclopentyl(S)-2-(3-{4-[6-Amino-5-(4-fluorobenzoyl)-2-oxo-2H-pyridin-1-yl]phenoxy}propylamino)-3-phenylpropionate

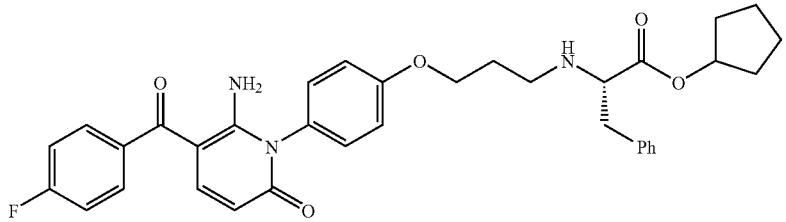

From Intermediate 4B and L-phenylalanine cyclopentyl ester (Intermediate 16), LCMS purity 93%, m/z 598 [M+H]+, 1H NMR (400 MHz, CD3OD), δ: 1.50-2.10 (8H, m), 2.50 (2H, m), 3.35-3.40 (1H, m), 3.55-3.70 (2H, m), 4.40-4.50 (2H, m), 4.60 (1H, m), 5.40-5.45 (1H, m), 6.05-6.10 (1H, d), 7.40-7.65 (11H, m), 7.85 (2H, m). 7.90 (1H, m).

Example 25

Cyclopentyl(S)-2-(3-{4-[6-Amino-5-(4-fluorobenzoyl)-2-oxo-2H-pyridin-1-yl]phenoxy}propylamino)-4-methylpentanoate

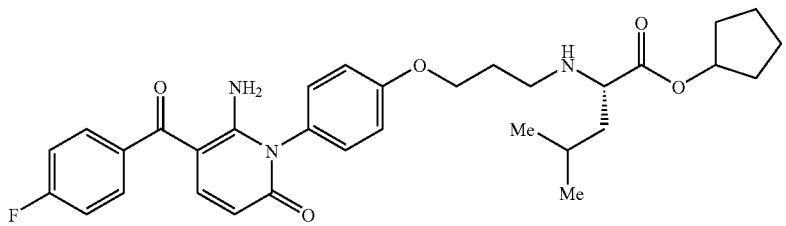

From Intermediate 4B and L-leucine cyclopentyl ester (Intermediate 8), LCMS purity 97%, m/z 564 [M+H]+, 1H NMR (400 MHz, d6-DMSO), δ: 0.90 (6H, m), 1.60-1.75 (10H, m), 1.90 (2H, m), 2.15 (2H, m), 3.10-3.30 (2H, m), 4.10 (1H, m), 4.15 (2H, m), 5.30 (1H, m), 5.70 (1H, d). 7.15 (2H, d), 7.30 (2H, d), 7.35 (2H, t), 7.50 (1H, d), 7.55 (1H, m) 9.05-30 (2H, m).

Example 26

Cyclopentyl(S)-(3-{4-[6-Amino-5-(4-fluoro-3-methylbenzoyl)-2-oxo-2H-pyridin-1-yl-phenoxy}propylamino)phenylacetate

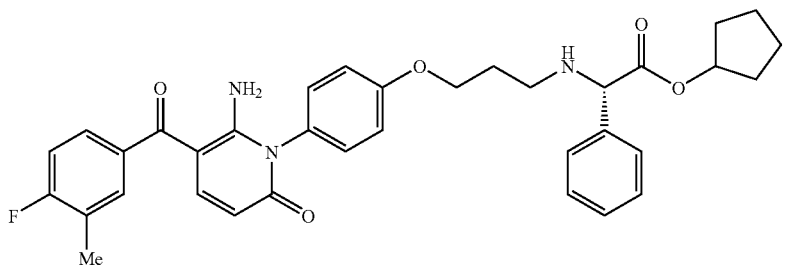

From Intermediate 4A and L-phenylglycine cyclopentyl ester tosylate salt (Intermediate 10), LCMS purity 95%, m/z 598 [M+H]$^+$, $^1$H NMR (400 MHz, d$_6$-DMSO), δ: 1.30 2.20 (10H, m), 2.30 (3H, m), 2.90-3.10 (2H, m), 4.15 (2H, m), 5.20 (1H, m), 5.30 (1H, m), 5.70 (1H, d), 7.10 (2H, d), 7.25-7.40 (5H, m), 7.40-7.50 (3H, m), 7.55 (5H, m), 9.70 (2H, m).

From Intermediate 4C and L-phenylglycine cyclopentyl ester tosylate salt (Intermediate 16), LCMS purity 99%, m/z 602 [M+H]$^+$, $^1$H NMR (400 MHz, d$_6$-DMSO), δ: 1.35-2.15 (10H, m), 2.90-3.10 (2H, m), 4.10 (2H, m), 5.25 (1H, m), 5.40 (1H, m), 5.70 (1H, d), 7.10 (2H, d), 7.25-7.30 (4H, m), 7.40-7.50 (2H, m), 7.55 (5H, m), 9.70 (2H, m).

Example 27

Cyclopentyl(S)-2-(3-{4-[6-Amino-5-(4-fluoro-3-methyl benzoyl)-2-oxo-2H-pyridin-1-yl]phenoxy}propylamino)-4-methylpentanoate

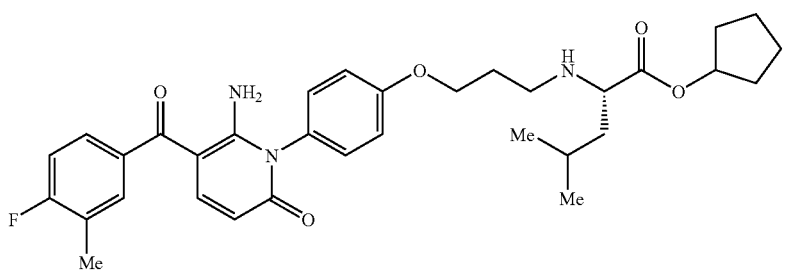

From Intermediate 4A and L-leucine cyclopentyl ester (Intermediate 8), LCMS purity 89%, m/z 578 [M+H]$^+$, $^1$H NMR (400 MHz, d$_6$-DMSO), δ: 0.95 (6H, m), 1.55-2.25 (12H, m), 2.30 (3H, m), 2.75-3.30 (2H, m), 4.15 (3H, m), 5.25 (1H, m), 5.70 (1H, d). 7.15 (2H, d), 7.30-7.40 (4H, m), 7.40-7.50 (2H, m).

Example 28

Cyclopentyl(S)-(3-{4-[6-Amino-5-(2,4-difluoro benzoyl)-2-oxo-2H-pyridin-1-yl]1-phenoxy}propylamino)phenyl acetate

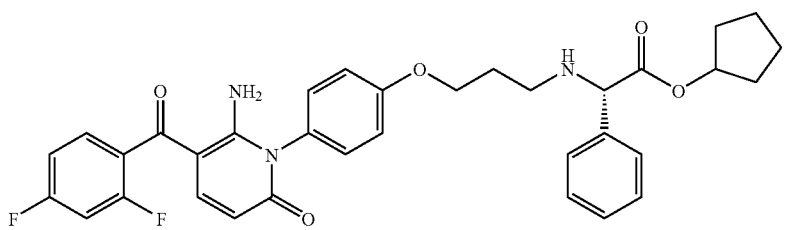

Example 29

Cyclopentyl(S)-2-(3-{4-[6-Amino-5-(2,4-difluoro benzoyl)-2-oxo-2H-pyridin-1-yl] phenoxy}propylamino)-3-phenyl propionate

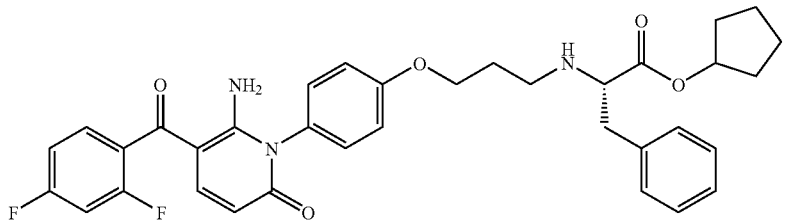

From Intermediate 4C and L-phenylalanine cyclopentyl ester tosylate salt (Intermediate 16), LCMS purity 99%, m/z 616 [M+H]$^+$, $^1$H NMR (400 MHz, d$_6$-DMSO), δ: 1.10-1.80 (8H, m), 2.20 (2H, m), 2.95 (1H, m), 3.10-3.30 (2H, m), 3.40 (2H, m), 4.20 (2H, m), 4.40 (1H, m), 5.05 (1H, m), 5.70 (1H, d), 7.15 (2H, d), 7.20-7.55 (11H, m), 9.70 (2H, m).

Example 30

Cyclopentyl(S)-2-(3-{4-[6-Amino-5-(2,4-difluoro benzoyl)-2-oxo-2H-pyridin-1-yl] phenoxy}propylamino)-4-methyl pentanoate

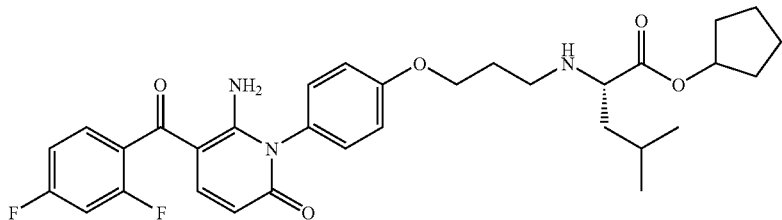

From Intermediate 4C and L-leucine cyclopentyl ester (Intermediate 8), LCMS purity 99%, m/z 582 [M+H]$^+$, $^1$H NMR (400 MHz, d$_6$-DMSO), δ: 0.95 (6H, m), 1.65-2.15 (13H, m), 3.10-3.20 (2H, m), 4.15 (3H, m), 5.30 (1H, m), 5.70 (1H, d), 7.15 (2H, d), 7.25-7.55 (6H, m), 9.24 (2H, m)

Example 31

Cyclopentyl(S)-2-(4-{4-[6-Amino-5-(4-fluorobenzoyl)-2-oxo-2H-pyridin-1-yl]-3,5-difluorophenoxy}cyclohexylamino)-4-methylpentanoate trifluoroacetate A suspension of Intermediate 5 (120 mg, 0.263 mmol) and L-Phenylalanine cyclopentyl ester tosylate salt (Intermediate 16) (98 mg, 0.263 mmol) in MeOH (1.2 ml) was allowed to stir at RT for 1 h before addition of NaCNBH$_3$ (66 mg, 1.05 mmol). Stirring was continued at RT for 18 h. Upon completion of reaction the reaction mixture was concentrated to dryness and partitioned between EtOAc (10 ml) and water (10 ml). The organic layer was dried (Na$_2$SO$_4$), filtered and concentrated to dryness under reduced pressure and was purified by preparative HPLC. This gave the desired product as a TFA salt. Yield=37 mg (18%).

LCMS purity 97%, m/z 674 [M+H]$^+$, $^1$H NMR (400 MHz, CD$_3$OD), δ: 1.10-2.20 (16H, m), 2.35-2.45 (1H, m), 2.70-3.00 (2H, m), 3.50-3.55 (1H, m), 4.25-4.35 (1H, m), 4.95-5.05 (1H, m), 5.70 (1H, d), 6.75 (2H, dd), 7.05-7.25 (7H, m), 7.45-7.55 (2H, m), 7.65 (1H, d)

The following examples were prepared in a similar manner:

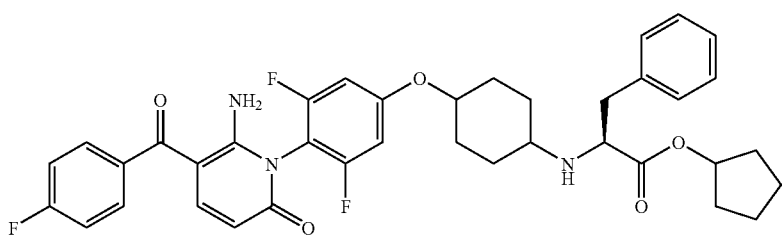

Example 32

Cyclopentyl(2S)-[(4-{4-[6-amino-5-(4-fluorobenzoyl)-2-oxopyridin-1(2H)-yl]-3,5-difluorophenoxy}cyclohexyl)amino](phenyl)acetate

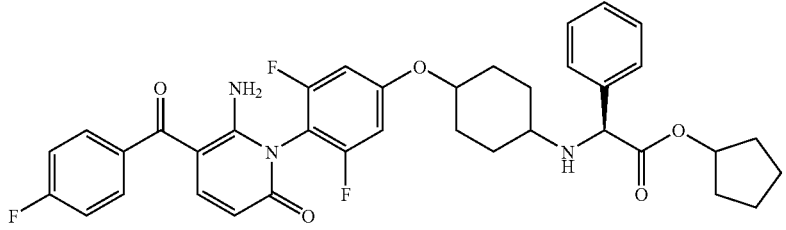

From Intermediate 5 (120 mg, 0.263 mmol) and L-phenylglycine cyclopentyl ester (Intermediate 10). LCMS purity 97%, m/z 660 [M+H]$^+$, $^1$H NMR (400 MHz, CD$_3$OD), δ: 1.30-1.80 (14H, m), 1.90-2.05 (2H, m), 2.35-2.50 (1H, m), 4.35-4.45 (1H, m), 4.50-4.60 (1H, m), 5.05-5.10 (1H, m), 5.70 (1H, d), 6.75-6.85 (2H, m), 7.10-7.15 (2H, m), 7.20-7.35 (5H, m), 7.45-7.55 (2H, m), 7.55-7.60 (1H, m).

Example 33

Cyclopentyl(S)-2-(4-{4-[6-Amino-5-(4-fluorobenzoyl)-2-oxo-2H-pyridin-1-yl]-3,5-difluorophenoxy}cyclohexylamino)-4-methylpentanoate

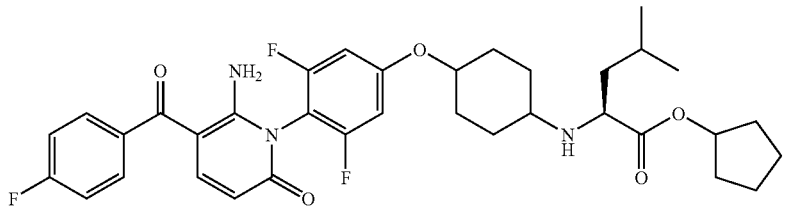

From Intermediate 5 (120 mg, 0.263 mmol) and L-Leucine cyclopentyl ester (Intermediate 8). LCMS purity 100%, m/z 640 [M+H]$^+$, $^1$H NMR (400 MHz, CD$_3$OD), δ: 0.95-1.05 (6H, m), 1.50-2.00 (16H, m), 2.10-2.35 (3H, m), 3.15-3.20 (1H, m), 4.00-4.15 (1H, m), 4.40 and 4.75 (0.5H each, m), 5.25-5.35 (1H, m), 5.75 (1H, d), 6.85-6.95 (2H, m), 7.15-7.25 (2H, m), 7.55-7.65 (2H, m), 7.65-7.70 (1H, m).

Examples 34 and 35

Cyclopentyl(S)-2-{4-[6-Amino-5-(4-fluorobenzoyl)-2-oxo-2H-pyridin-1-yl]cyclohexyl amino}-3-phenylpropionate

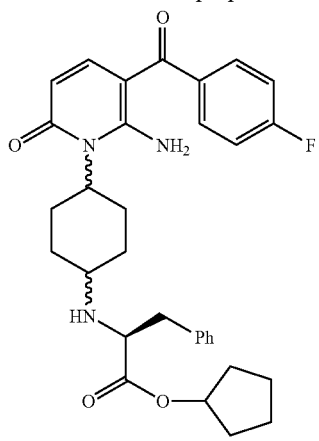

Intermediate 6 (50 mg, 0.15 mmol) was added to a colourless solution of L-phenylalanine cyclopentyl ester (89 mg, 0.38 mmol) in MeOH (10 ml) at RT/N$_2$ and stirred at RT for 1 h. AcOH glacial was added dropwise to adjust the pH to 6 followed by the NaCNBH$_3$ (38 mg, 0.61 mmol). The resultant colourless solution was stirred at RT overnight and then carefully quenched with sat. NaHCO$_3$ (20 ml) and extracted into CH$_2$Cl$_2$ (3×15 ml). The combined organic phases were washed with 2M HCl (2×20 ml), brine (20 ml), dried (Na$_2$SO$_4$), filtered and concentrated in vacuo giving a cream coloured solid. Purification by flash column chromatography (silica, gradient elution 40-100% EtOAc/heptane) gave the desired material, separable as two isomers, isomer 1 (Example 34) as a white solid (Yield=39 mg, 47%) LCMS purity 100%, m/z 546 [M+H]$^+$, $^1$H NMR (400 MHz, CD$_3$OD), δ: 1.40-2.05 (16H, m), 2.85-3.10 (3H, m), 3.60-3.70 (1H, m), 4.55-4.65 (1H, m), 5.10-5.20 (1H, m), 5.70 (1H, d), 7.15-7.40 (7H, m), 7.45-7.50 (1H, m), 7.50-7.60 (2H, m) and isomer 2 (Example 35) LCMS purity 97%, m/z 546 [M+H]$^+$, $^1$H NMR (400 MHz, CD$_3$OD), δ: 1.25-1.85 (12H, m), 1.95-2.20 (2H, m), 2.45-2.95 (4H, m), 3.00-3.10 (1H, m), 3.65-3.75 (1H, m), 4.55-4.65 (1H, m), 5.05-5.15 (1H, m), 5.65 (1H, d), 7.20-7.35 (7H, m), 7.40-7.50 (1H, m), 7.50-7.60 (2H, m) as a colourless film (Yield=15 mg, 18%).

Example 36 tert-Butyl(S)-(3-{4-[6-Amino-5-(2,4-difluoro benzoyl)-2-oxo-2H-pyridin-1-yl]-3,5-difluorophenoxy}propylamino)phenyl acetate

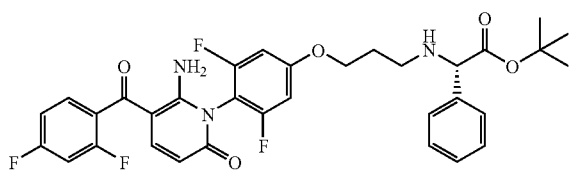

From Intermediate 4F and L-phenylglycine tert-butyl ester, LCMS purity 93%, m/z 626 [M+H]$^+$, $^1$H NMR (400 MHz, CD$_3$OD), δ: 1.30 (9H, s), 2.15 (2H, m), 3.00-3.15 (2H, m), 4.06 (2H, m), 5.02 (1H, s), 5.70 (1H, d), 6.75 (2H, d), 7.02 (2H, m), 7.30-7.50 (7H, m).

Example 37 tert-Butyl(S)-2-(3-{4-[6-Amino-5-(2,4-difluorobenzoyl)-2-oxo-2H-pyridin-1-yl]-3,5-difluorophenoxy}-propylamino)-3-phenyl propionate

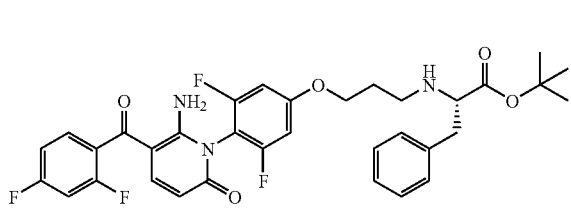

From Intermediate 4F and L-phenylalanine tert-butyl ester. LCMS purity 97%, m/z 640 [M+H]$^+$, $^1$H NMR (400 MHz, CD$_3$OD), δ: 1.25 (9H, s), 2.16 (2H, m), 3.00 (1H, dd), 3.15-3.25 (2H, m), 3.35 (1H, dd), 4.10 (2H, m), 4.20 (1H, m), 5.71 (1H, d), 6.79 (2H, d), 7.02 (2H, t), 7.20-7.30 (5H, m), 2H (2H, m).

Example 38 tert-Butyl(S)-2-(3-{4-[6-Amino-5-(2,4-difluoro benzoyl)-2-oxo-2H-pyridin-1-yl]-3,5-difluorophenoxy}propylamino)-4-methyl pentanoate

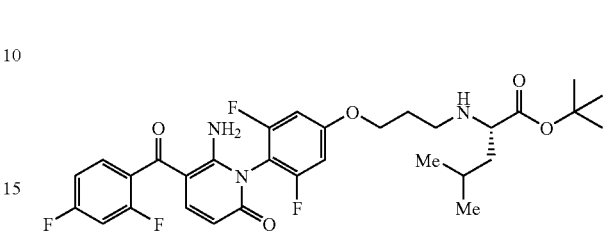

From Intermediate 4F and L-leucine tert-butyl ester, LCMS purity 97%, m/z 606 [M+H]$^+$, $^1$H NMR (400 MHz, CD$_3$OD), δ: 0.95 (6H, m), 1.41 (9H, s), 1.61 (1H, m), 1.75 (2H, m), 2.15 (2H, m), 3.22-3.25 (2H, m), 3.88 (1H, m), 4.13 (2H, m), 4.20 (1H, m), 5.40 (1H, s), 5.75 (1H, d), 6.85 (2H, d), 7.00 (2H, t), 7.40 (2H, m).

Example 39 tert-Butyl(S)-2-(3-{4-[6-Amino-5-(2,4-difluoro benzoyl)-2-oxo-2H-pyridin-1-yl] phenoxy}propylamino)-4-methyl pentanoate

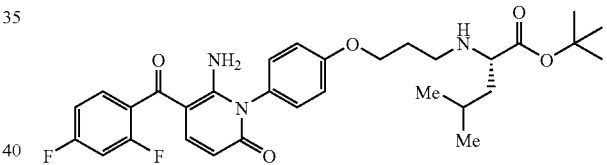

From Intermediate 4C and L-leucine tert-butyl ester, LCMS purity 91%, m/z 570 [M+H]$^+$, $^1$H NMR (400 MHz, CD$_3$OD), δ: 0.95 (6H, m), 1.45 (9H, s), 1.65 (1H, m), 2.15 (2H, m), 3.15-3.30 (2H, m), 3.85 (1H, m), 4.15 (2H, m), 5.75 (1H, d), 7.00-7.20 (6H, m), 7.35 (2H, m).

Example 40

2,3-Dihydro-1H-inden-2-yl (2S)-[(3-{4-[6-amino-5-(2,4-difluorobenzoyl)-2-oxopyridin-1(2H)-yl]-3,5-difluorophenoxy}propyl)amino](phenyl)acetate

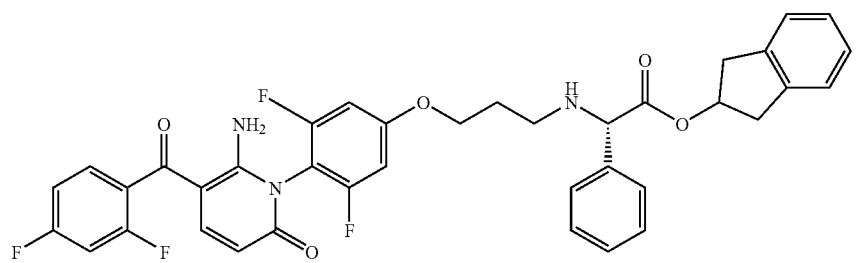

From Intermediate 4F and L-phenylglycine indanyl ester (Intermediate 11), LCMS purity 96%, m/z 686 [M+H]+, $^1$H NMR (300 MHz, CD$_3$OD), δ: 7.55-7.47 (2H, m), 7.46-7.31 (5H, m), 7.22-7.10 (6H, m), 6.85 (2H, d, J=9.6 Hz), 5.82 (1H, d, J=9.6 Hz), 5.57-5.51 (1H, m), 4.37 (1H, s), 4.13 (1H, t, J=6.0 Hz), 3.32-3.21 (2H, m), 3.05-2.98 (1H, m), 2.80-2.63 (3H, m), 2.05-1.97 (2H, m).

Example 41

2,3-dihydro-1H-inden-2-yl (2R)-[(3-{4-[6-amino-5-(2,4-difluorobenzoyl)-2-oxopyridin-1(2H)-yl]-3,5-difluorophenoxy}propyl)amino](phenyl)acetate

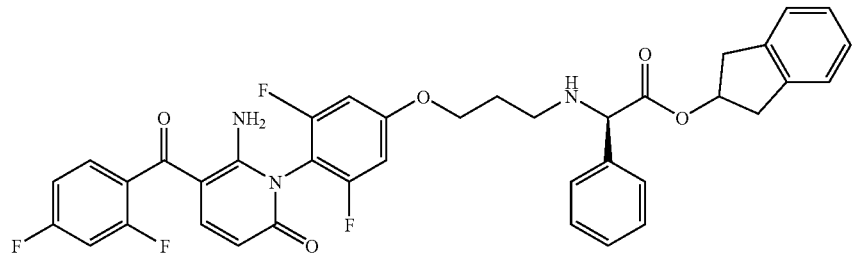

From Intermediate 4F and D-phenylglycine indanyl ester, LCMS purity 94%, m/z 686 [M+H]+, $^1$H NMR (300 MHz, CD$_3$OD), δ: 7.56-7.47 (2H, m), 7.38-7.31 (5H, m), 7.28-7.14 (6H, m), 6.85 (2H, d, J=9.6 Hz), 5.82 (1H, d, J=9.6 Hz), 5.57-5.52 (1H, m), 4.37 (1H, s), 4.13 (1H, t, J=6.0 Hz), 3.31-3.21 (2H, m), 3.09-2.99 (1H, m), 2.78-2.64 (3H, m), 2.06-1.99 (2H, m).

Example 42

Cyclopentyl (2R)-[(3-{4-[6-amino-5-(2,4-difluorobenzoyl)-2-oxopyridin-1 (2H)-yl]-3,5-difluorophenoxy}propyl)amino](phenyl)acetate

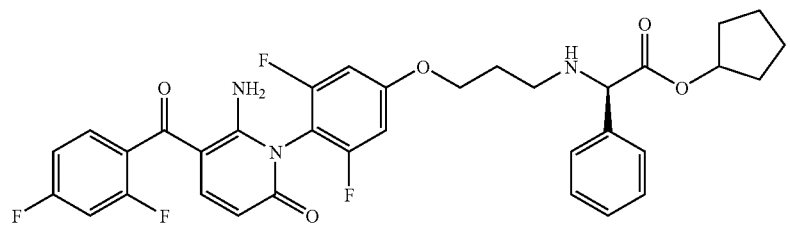

From Intermediate 4F and D-phenylglycine cyclopentyl ester, LCMS purity 95%, m/z 638 [M+H]+.

Example 43

Bicyclo[2.2.1]hept-2-yl(2S)-[(3-{4-[6-amino-5-(2,4-difluorobenzoyl)-2-oxopyridin-1(2H)-yl]-3,5-difluorophenoxy}propyl)amino](phenyl)acetate

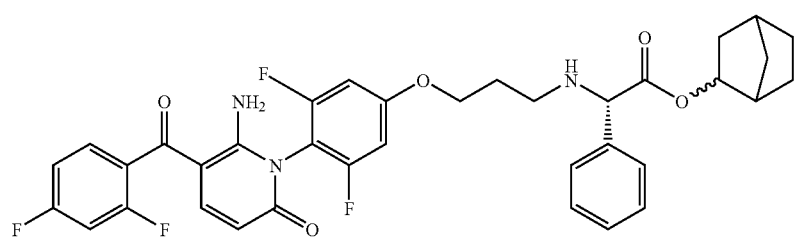

From Intermediate 4F and L-phenylglycine norbornyl ester (Intermediate 12), LCMS purity 97%, m/z 664 [M+H]⁺, ¹H NMR (300 MHz, CD₃OD), δ: 7.50-7.21 (7H, m), 7.02 (2H, t, J=8.6 Hz), 6.75 (2H, d, J=9.6 Hz), 5.70 (1H, d, J=9.6 Hz), 4.50 (1H, d, J=6.6 Hz), 4.32-4.26 (1H, m), 4.05 (2H, t, J=5.9 Hz), 2.71-2.56 (2H, m), 2.24-1.90 (4H, m), 1.64-1.06 (8H, m).

Example 44

Bicyclo[2.2.1]hept-2-yl (2R)-[(3-{4-[6-amino-5-(2,4-difluorobenzoyl)-2-oxopyridin-1(2H)-yl]-3,5-difluorophenoxy}propyl)amino](phenyl)acetate

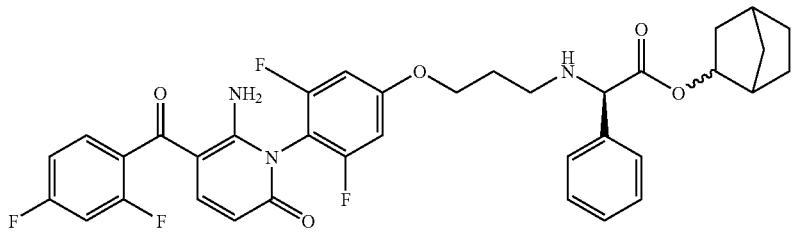

From Intermediate 4F and D-phenylglycine norbornyl ester, LCMS purity 98%, m/z 664 [M+H]⁺, ¹H NMR (300 MHz, CD₃OD), d: 7.42-7.17 (7H, m), 7.00 (2H, t, J=8.6 Hz), 6.74 (2H, d, J=9.1 Hz), 5.69 (1H, d, J=9.8 Hz), 4.49 (1H, d, J=6.8 Hz), 4.32-4.26 (1H, m), 4.03 (2H, t, J=6.0 Hz), 2.70-2.52 (2H, m), 2.18-1.86 (4H, m), 1.63-0.92 (8H, m).

Example 45 tert-Butyl(S)-(3-{4-[6-Amino-5-(4-difluoro benzoyl)-2-oxo-2H-pyridin-1-yl]-3,5-difluorophenoxy}propylamino)phenyl acetate

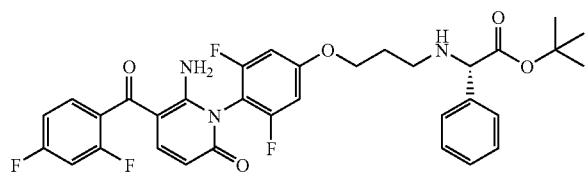

From Intermediate 4E and L-phenylglycine tert-butyl ester, LCMS purity 100%, m/z 608 [M+H]⁺, ¹H NMR (300 MHz, CD₃OD), δ: 7.55-7.47 (3H, m), 7.30-7.21 (6H, m), 7.09 (1H, t, J=8.7 Hz), 6.61 (2H, d, J=9.3 Hz), 5.81 (1H, d, J=9.6 Hz), 4.18 (1H, s), 4.03 (2H, t, J=6.0 Hz), 2.75-2.69 (1H, m), 2.65-2.58 (1H, m), 1.96-1.88 (1H, m), 1.96-1.88 (2H, m), 1.32 (9H, s)

Example 46

2-(Dimethylamino)ethyl N-(3-{4-[6-amino-5-(2,4-difluorobenzoyl)-2-oxopyridin-1(2H)-yl]-3,5-difluorophenoxy}propyl)-L-leucinate

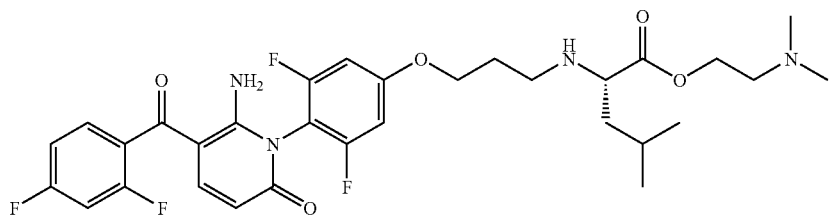

From Intermediate 4F and Intermediate 13, LCMS purity 90%, m/z 621 [M+H]⁺, ¹H NMR (300 MHz, DMSO), δ: 10.18 (1H, br s), 9.50 (1H, br s), 7.57 (1H, q, J=7.8 Hz), 7.39 (2H, m), 7.37-7.15 (3H, m), 7.04 (2H, m), 5.73 (1H, d, J=9.6 Hz), 4.59-4.46 (2H, m), 4.21 (2H, t, J=9.0 Hz), 4.11 (1H, m), 3.14 (2H, m), 2.86 (6H, s), 2.14 (2H, m), 1.74 (2H, m), 0.92 (8H, m).

Example 47

2-Morpholin-4-ylethyl N-(3-{4-[6-amino-5-(2,4-difluorobenzoyl)-2-oxopyridin-1(2H)-yl]-3,5-difluorophenoxy}propyl)-L-leucinate

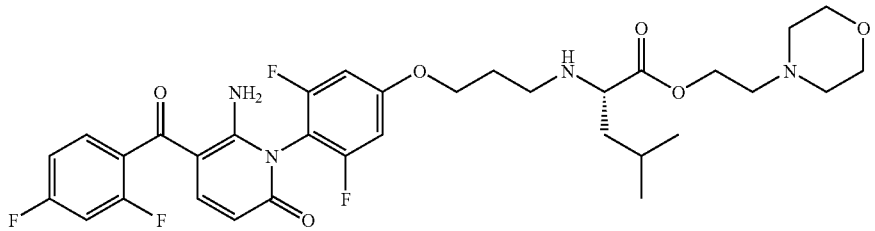

From Intermediate 4F and Intermediate 14, LCMS purity 90%, m/z 621 [M+H]$^+$, $^1$H NMR (300 MHz, DMSO), δ: 7.57 (1H, q, J=7.5 Hz), 7.40 (2H, m), 7.26-7.17 (3H, m), 7.06 (2H, d, J=10.8 Hz), 5.74 (1H, d, J=9.9 Hz), 4.53 (2H, m), 4.21 (4H, m), 3.80 (4H, m), 3.37 (2H, m), 3.17 (4H, m), 2.15 (2H, m), 1.75 (3H, m), 0.94 (6H, br s).

Example 48

Cyclopentyl(2S)-[(3-{4-[6-amino-5-(2,4-difluorobenzoyl)-2-oxopyridin-1(2H)-yl]-3,5-difluorophenoxy}propyl)amino](cyclohexyl)acetate

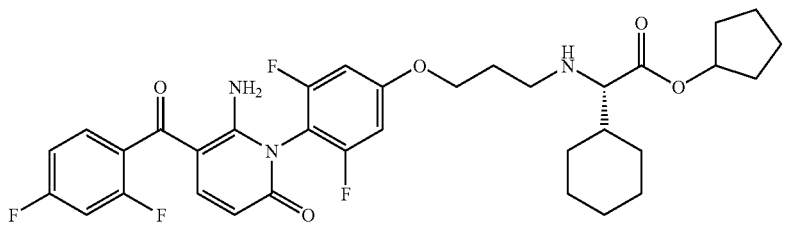

From Intermediate 4F and L-cyclohexylglycine cyclopentyl ester (Intermediate 9), LCMS purity 95%, m/z 664 [M+H]$^+$, $^1$H NMR (300 MHz, DMSO), δ: 9.15 (1H, br s), 8.95 (1H, br s), 7.62-7.52 (1H, m), 7.46-7.31 (2H, m), 7.27-7.20 (1H, m), 7.05 (2H, d, J=10.2 Hz), 5.74 (1H, d, J=9.6 Hz), 5.30-5.25 (1H, m), 4.20 (2H, t, J=5.7 Hz), 4.10-3.95 (1H, m), 3.25-2.95 (2H, m), 2.20-2.07 (2H, m), 2.00-1.50 (15H, m), 1.30-1.00 (4H, m), 0.95-0.75 (1H, m)

From Intermediate 4F and L-cyclohexylglycine tert-butyl ester, LCMS purity 95%, m/z 632 [M+H]$^+$, $^1$H NMR (300 MHz, DMSO), δ: 9.10 (1H, br s), 8.85 (1H, brs), 7.62-7.52 (1H, m), 7.45-7.31 (2H, m), 7.28-7.20 (1H, m), 7.06 (2H, d, J=10.2 Hz), 5.74 (1H, d, J=9.6 Hz), 4.20 (2H, t, J=5.9 Hz), 3.95-3.85 (1H, m), 3.25-2.95 (2H, m), 2.20-2.07 (2H, m), 2.00-1.60 (6H, m), 1.51 (9H, s), 1.35-1.07 (4H, m), 1.00-0.85 (1H, m).

Example 49 tert-Butyl (2S)-[(3-{4-[6-amino-5-(2,4-difluorobenzoyl)-2-oxopyridin-1(2H)-yl]-3,5-difluorophenoxy}propyl)amino](cyclohexyl)acetate

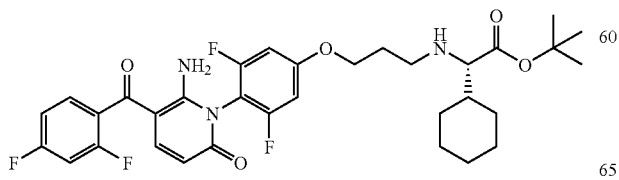

Example 50

Cyclopentyl N-(3-{4-[6-amino-5-(2,4-difluorobenzoyl)-2-oxopyridin-1(2H)-yl]-3,5-difluorophenoxy}propyl)-D-leucinate

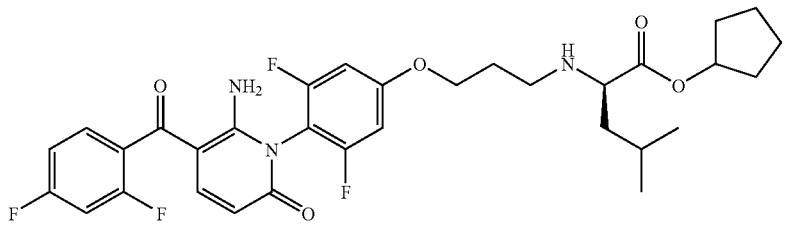

From Intermediate 4F and D-Leucine cyclopentyl ester, LCMS purity 95%, m/z 618 [M+H]$^+$, $^1$H NMR (300 MHz, DMSO), δ: 10.10 (1H, brs), 9.40-9.10 (2H, m), 8.15 (1H, br s), 7.62-7.52 (1H, m), 7.47-7.31 (2H, m), 7.28-7.12 (1H, m), 7.07 (2H, d, J=10.5 Hz), 5.73 (1H, d, J=9.6 Hz), 5.30-5.20 (1H, m), 4.25-4.00 (3H, m), 3.30-3.00 (2H, m), 2.20-2.00 (2H, m), 1.95-1.80 (2H, m), 1.75-1.55 (10H, m), 1.00-0.90 (6H, m).

Example 51 tert-Butyl N-(3-{4-[6-amino-5-(2,4-difluorobenzoyl)-2-oxopyridin-1(2H)-yl]-3,5-difluorophenoxy}propyl)-D-leucinate

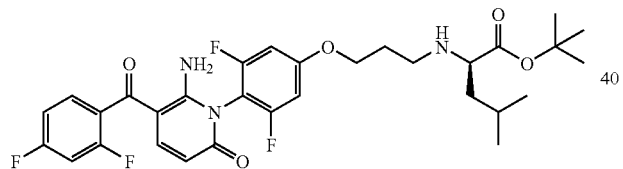

From Intermediate 4F and D-Leucine tert-butyl ester, LCMS purity 95%, m/z 606 [M+H]$^+$, $^1$H NMR (300 MHz, DMSO), δ: 9.30-9.00 (2H, m), 7.62-7.52 (1H, m), 7.47-7.32 (2H, m), 7.28-7.12 (1H, m), 7.06 (2H, d, J=10.2 Hz), 5.73 (1H, d, J=9.6 Hz), 4.20 (2H, t, J=5.7 Hz), 3.99 (1H, br s), 3.25-2.95 (2H, m), 2.20-2.05 (2H, m), 1.80-1.60 (3H, m), 1.49 (9H, s), 0.95 (6H, d, J=4.8 Hz).

Example 52

Cyclopentyl(2S)-4-amino-2-[(3-{4-[6-amino-5-(2,4-difluorobenzoyl)-2-oxopyridin-1(2H)-yl]-3,5-difluorophenoxy}propyl)amino]butanoate

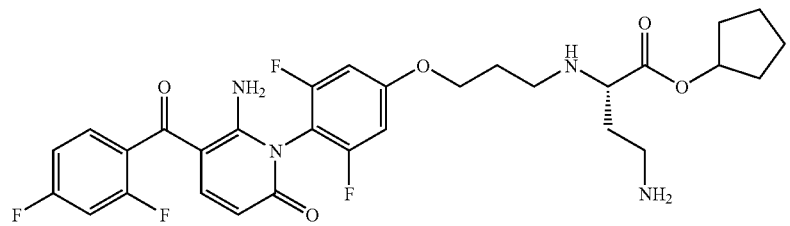

From Intermediate 4F and Intermediate 15, LCMS purity 90%, m/z 605 [M+H]$^+$, $^1$H NMR (300 MHz, CD$_3$OD), δ: 7.46-7.55 (2H, m), 7.12 (2H, t, J=8.7 Hz), 6.93 (2H, d, J=9.6 Hz), 5.81 (1H, d, J=9.6 Hz), 5.37-5.44 (1H, m), 4.20-4.31 (4H, m), 3.33-3.42 (1H, m), 2.25-2.49 (4H, m), 1.91-2.08 (2H, m), 1.65-1.89 (7H, m).

Example 53

Cyclopentyl N-(5-{4-[6-amino-5-(2,4-difluorobenzoyl)-2-oxopyridin-1(2H)-yl]-3,5-difluorophenoxy}pentyl)-L-leucinate

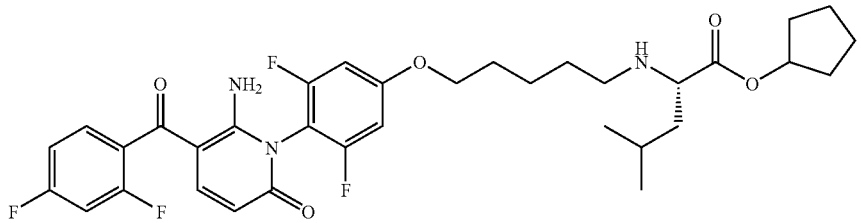

From Intermediate 4G. To a solution of 6-Amino-1-{4-[(5-chloropentyl)oxy]-2,6-difluorophenyl}-5-(2,4-difluorobenzoyl)pyridin-2(1H)-one (138 mg, 0.29 mmol) in anhydrous DMF (3 ml) under an atmosphere of nitrogen was added cyclopentyl L-leucinate (Intermediate 8) (284 mg, 1.43 mmol, 5 eq), sodium iodide (86 mg, 0.57 mmol, 2 eq) and N,N-diisopropylethylamine (0.052 ml, 0.29 mmol, 1 eq). The mixture was heated at 90° C. for 16 hours, before being allowed to cool to room temperature and diluted with EtOAc (25 ml). The solution was washed with water (2×25 ml) and brine (25 ml). The organic layer was dried over MgSO$_4$, filtered and concentrated under reduced pressure. Purification by column chromatography (3-4% MeOH in DCM) followed by preparative HPLC afforded the title compound as a cream coloured solid (96 mg, 52% yield).

LC/MS: m/z 646 [M+H]$^+$. $^1$H NMR (300 MHz, CD$_3$OD) δ: 7.56-7.47 (2H, m), 7.13 (2H, m), 6.88 (2H, m), 5.82 (1H, d, J=9.8 Hz), 5.23 (1H, t, J=4.1 Hz), 4.11 (2H, t, J=6.3 Hz), 3.28 (1H, m), 2.61-2.51 (2H, m), 1.95-1.41, (17H, br m), 0.98-0.93 (6H, m).

Example 54 tert-Butyl N-(5-{4-[6-amino-5-(2,4-difluorobenzoyl)-2-oxopyridin-1(2H)-yl]-3,5-difluorophenoxy}pentyl)-L-leucinate From Intermediate 4G. To a solution of 6-Amino-1-{4-[(5-chloropentyl)oxy]-2,6-difluorophenyl}-5-(2,4-difluorobenzoyl)pyridin-2(1H)-one (96 mg, 0.20 mmol) in anhydrous DMF (3 ml) under an atmosphere of nitrogen was added tert-butyl L-leucinate hydrochloride (198 mg, 0.99 mmol, 5 eq), sodium iodide (60 mg, 0.40 mmol, 2 eq) and N,N-diisopropylethylamine (0.072 ml, 0.40 mmol, 2 eq). The mixture was heated at 90° C. for 20 hours, before being allowed to cool to room temperature and diluted with EtOAc (20 ml). The solution was washed with water (2×20 ml) and brine (20 ml). The organic layer was dried over MgSO$_4$, filtered and concentrated under reduced pressure. Purification by column chromatography (1-3% MeOH in DCM) followed by preparative HPLC afforded the title compound as a white solid (23 mg, 18% yield).

LC/MS: m/z 634 [M+H]$^+$. $^1$H NMR (300 MHz, CD$_3$OD) δ: 7.56-7.47 (2H, m), 7.14 (2H, m), 6.89 (2H, m), 5.81 (1H, d, J=9.6 Hz), 4.11 (2H, t, J=6.2 Hz), 3.19 (1H, m), 2.60-2.53 (2H, m), 1.89-1.84 (2H, m), 1.72-1.41 (16H, m), 0.96 (6H, m).

Example 55

Cyclopentyl N-(5-{4-[6-amino-5-(4-fluorobenzoyl)-2-oxopyridin-1(2H)-yl]-3,5-difluorophenoxy}pentyl)-L-leucinate

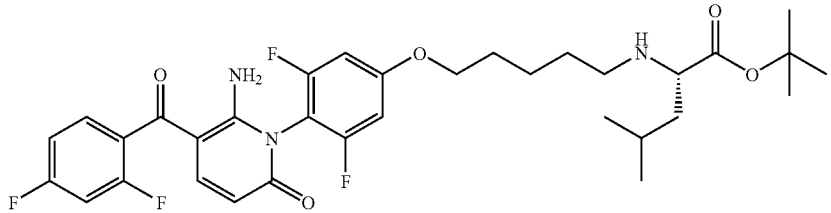

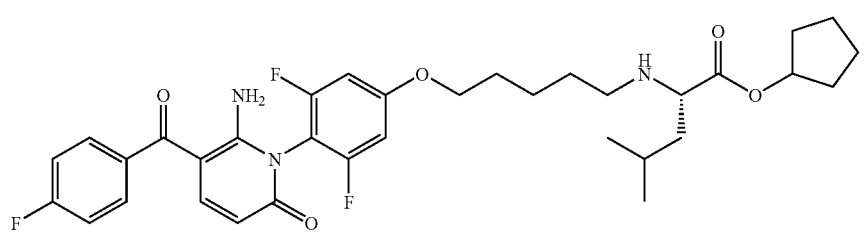

From Intermediate 4H. To a solution of 6-amino-1-{4-[(5-chloropentyl)oxy]-2,6-difluorophenyl}-5-(4-fluorobenzoyl)pyridin-2(1H)-one (99 mg, 0.21 mmol) in anhydrous DMF (3 ml) under an atmosphere of nitrogen was added cyclopentyl L-leucinate (Intermediate 8) (212 mg, 1.06 mmol, 5 eq), sodium iodide (64 mg, 0.43 mmol, 2 eq) and N,N-diisopropylethylamine (0.039 ml, 0.21 mmol, 1 eq). The mixture was heated at 90° C. for 20 hours, before being allowed to cool to room temperature and diluted with EtOAc (25 ml). The solution was washed with water (2×25 ml) and brine (25 ml). The organic layer was dried over MgSO$_4$, filtered and concentrated under reduced pressure. Purification by column chromatography (2% MeOH in DCM) followed by preparative HPLC afforded the title compound as a yellow solid (64 mg, 48% yield).

LC/MS: m/z 628 [M+H]$^+$. $^1$H NMR (300 MHz, CD$_3$OD) δ: 7.71 (1H, d, J=9.6 Hz), 7.62 (2H, m), 7.26 (2H, m), 6.89 (2H, m), 5.81 (1H, d, J=9.6 Hz), 5.23 (1H, t, J=5.3 Hz), 4.11 (2H, t, J=6.4 Hz), 3.28 (1H, m), 2.55 (2H, m), 1.91-1.48 (17H, m), 0.98-0.93 (6H, m).

Example 56

Cyclopentyl N-({4-[6-amino-5-(4-fluorobenzoyl)-2-oxopyridin-1(2H)-yl]phenoxy}acetyl)-L-leucinate

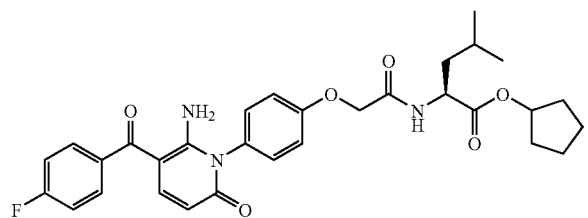

LC/MS: m/z 564 [M+H]$^+$. $^1$H NMR (300 MHz, DMSO-d$_6$) δ: 8.47 (1H, d, J=7.7 Hz), 7.56 (2H, m), 7.45 (1H, d, J=9.6 Hz), 7.38-7.24 (4H, m), 7.15 (2H, m), 5.69 (1H, d, J=9.8 Hz), 5.09 (1H, t, J=5.3 Hz), 4.63 (2H, m), 4.31 (1H, m), 1.84-1.79 (2H, m), 1.66-1.53 (9H, m), 0.92-0.86 (6H, m).

To a solution of 6-amino-5-(4-fluorobenzoyl)-1-(4-hydroxyphenyl)pyridin-2(1H)-one [WO 03/076405] (100 mg, 0.31 mmol) in anhydrous DMF (3 ml) under an atmosphere of nitrogen was added cyclopentyl N-(bromoacetyl)-L-leucinate (109 ml, 0.34 mmol, 1.1 eq) and potassium carbonate (51 mg, 0.37 mmol, 1.2 eq). The mixture was heated at 40 C for 16 hours, before being allowed to cool to room temperature and added to water (20 ml). The mixture was extracted with EtOAc (3×15 ml), and the combined extracts washed with water (2×40 ml) and brine (40 ml). The organic layer was dried over MgSO$_4$, filtered and concentrated under reduced pressure. Purification by column chromatography (2-3% MeOH in DCM) followed by trituration with minimal MeOH afforded the title compound as a white solid (91 mg, 52% yield).

The cyclopentyl N-(bromoacetyl)-L-leucinate was synthesised from cyclopentyl L-leucinate in one step, the details of which are outlined below.

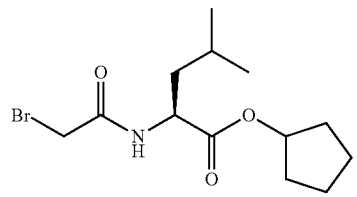

To a solution of cyclopentyl L-leucinate (Intermediate 8) (568 mg, 2.84 mmol) in DCM (6 ml) was added triethylamine (0.24 ml, 2.84 mmol, 1 eq) and bromoacetyl chloride (1.44 ml, 3.13 mmol, 1.1 eq) dropwise. The mixture was stirred at room temperature for 20 hours, diluted with DCM (50 ml) and washed with water (50 ml) and brine (50 ml). The organic layer was dried over MgSO$_4$, filtered and concentrated under reduced pressure to afford a crude mixture containing the title compound (902 mg) that was used without further purification. LC/MS: m/z 320/322 [M+H]$^+$.

Example 57

Cyclopentyl N-[2-(4-{6-amino-5-[(4-fluorophenyl)carbonyl]-2-oxopyridin-1(2H)-yl}phenyl)ethyl]-L-leucinate

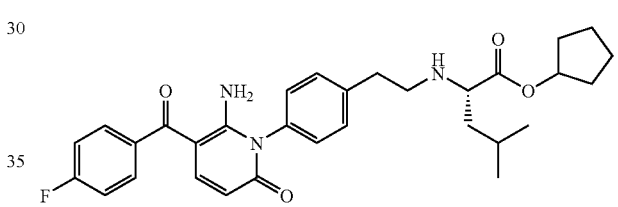

From Intermediate 4J and L-Leucine cyclopentyl ester (Intermediate 8). LC/MS: m/z 534 [M+H]$^+$. $^1$H NMR (300 MHz, DMSO-d$_6$) δ: 8.47 (1H, d, J=7.7 Hz), 7.56 (2H, m), 7.45 (1H, d, J=9.6 Hz), 7.38-7.24 (4H, m), 7.15 (2H, m), 5.69 (1H, d, J=9.8 Hz), 5.09 (1H, t, J=5.3 Hz), 4.63 (2H, m), 4.31 (1H, m), 1.84-1.79 (2H, m), 1.66-1.53 (9H, m), 0.92-0.86 (6H, m).

The following examples were synthesised in a similar manner:

Example 58 tert-Butyl N-[2-(4-{6-amino-5-[(4-fluorophenyl)carbonyl]-2-oxopyridin-1(2H)-yl}phenyl)ethyl]-L-leucinate

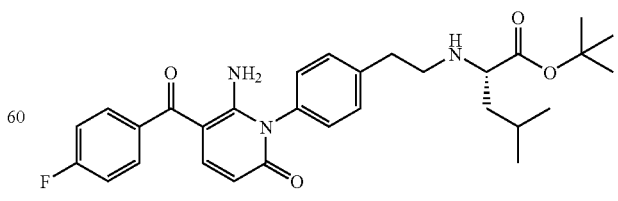

From Intermediate 4J and L-Leucine tbutyl ester. LC/MS: m/z 522 [M+H]$^+$. $^1$H NMR (300 MHz, DMSO-d$_6$) δ: 9.40-9.10 (2H, m), 7.59-7.44 (5H, m), 7.38-7.30 (4H, m), 5.71 (1H, d, J=9.6 Hz), 4.00 (1H, brs), 3.40-3.28 (1H, m), 3.25-3.15 (1H, m), 3.10-3.00 (2H, m), 1.80-1.70 (3H, m), 0.96 (6H, d, J=5.1 Hz).

Example 59

Cyclopentyl N-[2-(4-{6-amino-5-[(2,4-difluorophenyl)carbonyl]-2-oxopyridin-1(2H)-yl}phenyl)ethyl]-L-leucinate

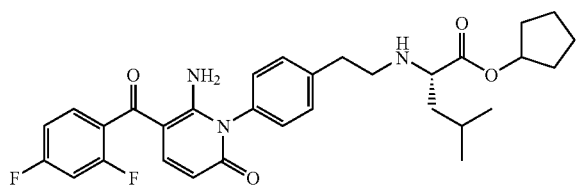

Example 59 was synthesised via a similar route to Example 57 using 3-(2,4-difluoro-phenyl)-3-oxo-thiopropionimidic acid 4-chloro-phenyl ester. LC/MS: m/z 552 [M+H]$^+$. $^1$H NMR (300 MHz, DMSO-d$_6$) δ: 10.07 (1H, br s), 9.35 (2H, br s), 7.55-6.95 (8H, m), 5.72 (1H, d, J=9.9 Hz), 5.27 (1H, t, J=5.7 Hz), 4.15-4.00 (1H, m), 3.41-3.15 (2H, m), 3.10-3.00 (2H, m), 1.96-1.80 (2H, m), 1.78-1.55 (9H, m), 0.95 (6H, d, J=5.1 Hz).

Example 60 tert-Butyl N-[2-(4-{6-amino-5-[(2,4-difluorophenyl)carbonyl]-2-oxopyridin-1(2H)-yl}phenyl)ethyl]-L-leucinate

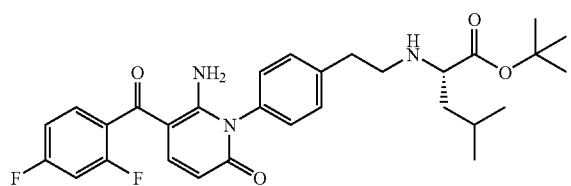

Example 60 was synthesised via a similar route to Example 57 using 3-(2,4-difluoro-phenyl)-3-oxo-thiopropionimidic acid 4-chloro-phenyl ester. LC/MS: m/z 540 [M+H]$^+$. $^1$H NMR (300 MHz, DMSO-d$_6$) δ: 10.07 (1H, br s), 9.30 (2H, br s), 7.55-6.94 (8H, m), 5.72 (1H, d, J=9.6 Hz), 4.05-3.93 (1H, m), 3.40-3.10 (2H, m), 3.08-3.00 (2H, m), 1.80-1.65 (3H, m), 1.50 (9H, s), 0.96 (6H, d, J=5.1 Hz).

Example 61

Cyclopentyl(2S)-{[2-(4-{6-amino-5-[(4-fluorophenyl)carbonyl]-2-oxopyridin-1(2H)-yl}phenyl)ethyl]amino}(phenyl)ethanoate

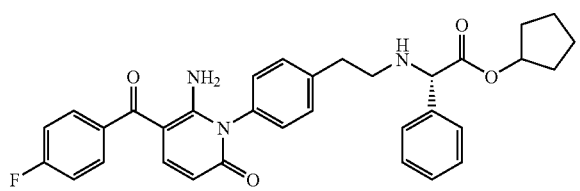

From Intermediate 4J and L-Phenylglycine cyclopentyl ester (Intermediate 10). LC/MS: m/z 554 [M+H]$^+$. $^1$H NMR (300 MHz, CDCl$_3$) δ: 10.35 (1H, br s), 7.60-7.13 (14H, m), 5.91 (1H, d, J=10.2 Hz), 5.22-5.14 (1H, m), 4.36 (1H, s), 3.00-2.85 (4H, m), 2.16 (1H, br s), 1.99-1.43 (8H, m).

Example 62 tert-Butyl (2S)-{[2-(4-{6-amino-5-[(4-fluorophenyl)carbonyl]-2-oxopyridin-1(2H)-yl}phenyl)ethyl]amino}(phenyl)ethanoate

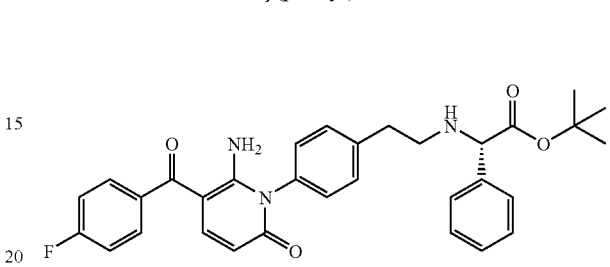

From Intermediate 4J and L-Phenylglycine tbutyl ester. LC/MS: m/z 542 [M+H]$^+$. $^1$H NMR (300 MHz, CDCl$_3$) δ: 10.30 (1H, br s), 7.51-7.45 (3H, m), 7.38 (2H, d, J=6.9 Hz), 7.27-7.04 (9H, m), 5.82 (1H, d, J=9.6 Hz), 4.20 (1H, s), 2.86-2.75 (4H, m), 2.04 (1H, br s), 1.31 (9H, s).

Example 63

Cyclopentyl N-[2-(4-{6-amino-5-[(4-methylphenyl)carbonyl]-2-oxopyridin-1(2H)-yl}phenyl)ethyl]-L-leucinate

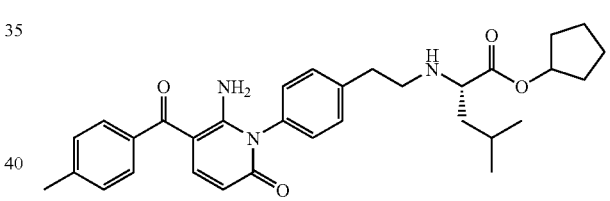

Example 63 was prepared by similar methodology to Example 59 using 3-(4-methyl-phenyl)-3-oxo-thiopropionimidic acid 4-chloro-phenyl ester, prepared by a similar method used for Intermediate 4J. LC/MS: m/z 530 [M+H]$^+$. $^1$H NMR (300 MHz, CDCl$_3$) δ: 7.65 (1H, d, J=9.9 Hz), 7.47 (4H, m), 7.26 (4H, m), 5.89 (1H, d, J=9.9 Hz), 5.20 (1H, m), 3.25 (1H, t, J=7.2 Hz), 2.87 (4H, m), 2.44 (3H, s), 1.99-1.53 (9H, m), 1.42 (2H, t, J=6.3 Hz), 0.91 (6H, m).

Example 64

Cyclopentyl N-[2-(4-{6-amino-5-[(4-methoxyphenyl)carbonyl]-2-oxopyridin-1(2H)-yl}phenyl)ethyl]-L-leucinate

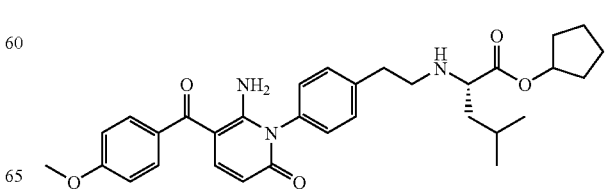

Example 64 was prepared by similar methodology to Example 59 using 3-(4-methoxy-phenyl)-3-oxo-thiopropionimidic acid 4-chloro-phenyl ester, prepared by a similar method used for Intermediate 4J. LC/MS: m/z 546 [M+H]$^+$. $^1$H NMR (300 MHz, CDCl$_3$) δ: 7.67 (1H, d, J=9.9 Hz), 7.55 (2H, d), 7.46 (2H, d), 7.24 (2H, d, J=8.4 Hz), 6.98 (2H, d, J=6.9 Hz), 5.90 (1H, d, J=9.6 Hz), 5.18 (1H, m), 3.88 (3H, s), 3.24 (1H, t, J=7.2 Hz), 2.87 (4H, m), 1.97-1.53 (9H, m), 1.43 (2H, t), 0.90 (6H, m).

Example 65

Cyclopentyl N-[2-(4-{6-amino-5-[(4-chlorophenyl)carbonyl]-2-oxopyridin-1(2H)-yl}phenyl)ethyl]-L-leucinate

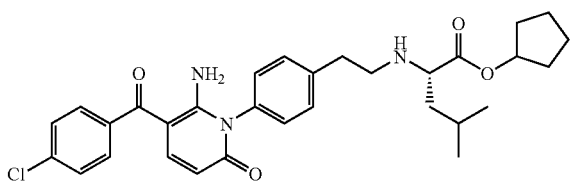

Example 65 was prepared by similar methodology to Example 59 using 3-(4-chloro-phenyl)-3-oxo-thiopropionimidic acid 4-chloro-phenyl ester, prepared by a similar method used for Intermediate 4J. LC/MS: m/z 551 [M+H]$^+$. $^1$H NMR (300 MHz, CDCl$_3$) δ: 7.40 (7H, m), 7.16 (2H, d, J=8.4 Hz), 5.82 (1H, d, J=9.9 Hz), 5.11 (1H, m), 3.17 (1H, t, J=7.5 Hz), 2.78 (4H, m), 1.92-1.43 (9H, m), 1.35 (2H, t), 0.82 (6H, dd).

Example 66

Cyclopentyl N-[3-(4-{6-amino-5-[(4-fluorophenyl)carbonyl]-2-oxopyridin-1(2H)-yl}-3-fluorophenoxy)propyl]-L-leucinate Example 66 was prepared by similar methodology to Example 25 using 6-Amino-5-(4-fluoro-3-methyl-benzoyl)-1-[2-fluoro-4-hydroxy-phenyl]-1H-pyridin-2-one [WO 03/076405]. LCMS purity 97%, m/z 582 [M+H]$^+$, $^1$H NMR (400 MHz, d$_6$-DMSO), δ: 7.57 (2H, m), 7.48 (1H, d, J=9.6 Hz), 7.34 (3H, m), 7.10 (1H, dd, J=11.9, 2.3 Hz), 7.00 (1H, dd, J=9.7, 2.3 Hz), 5.70 (1H, d, J=9.6 Hz), 5.12 (1H, m), 4.11 (2H, t, J=6.2 Hz), 3.14 (1H, m), 2.68 (1H, m), 1.98 (1H, m), 1.88-1.82 (4H, m), 1.67-1.57 (7H, m), 0.88 (6H, t, J=7.2 Hz).

Example 67

Cyclopentyl N-[3-(4-{6-amino-5-[(4-fluorophenyl)carbonyl]-2-oxopyridin-1(2H)-yl}phenyl)propyl]-L-leucinate

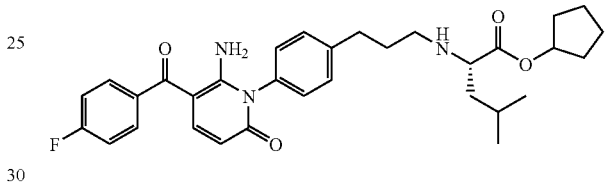

Example 61 was synthesised via a similar route to Example 57 using 3-(4-Amino-phenyl)-propan-1-ol. LC/MS: m/z 548 [M+H]$^+$. $^1$H NMR (300 MHz, DMSO-d$_6$) δ: 9.13 (2H, br s), 7.59-7.52 (2H, m), 7.50-7.42 (3H, m), 7.39-7.25 (4H, m), 5.70 (1H, d, J=9.6 Hz), 5.28-5.24 (1H, m), 4.04 (1H, br s), 3.35-2.85 (2H, m), 2.80-2.70 (2H, m), 2.10-1.80 (4H, m), 1.75-1.55 (10H, m), 0.93 (6H, d, J=3.4 Hz).

The 3-(4-Amino-phenyl)-propan-1-ol was synthesised in a one step process from 4-nitro cinnamyl alcohol as shown below:

To a solution of 4-nitro cinnamyl alcohol (2 g, 11.1 mmol) in methanol (30 ml) under a nitrogen atmosphere was added Raney Nickel (2 ml slurry in water). The reaction was then exposed to hydrogen gas and stirred under a hydrogen atmosphere for 12 hours for complete reaction. The reaction mixture was filtered through Celite, washing with methanol and ethyl acetate. The filtrate was then concentrated under reduced pressure before purification by column chromatography (8:2 EtOAc:Hexane) to give the required product (1.68 g, 95%) as a yellow solid.

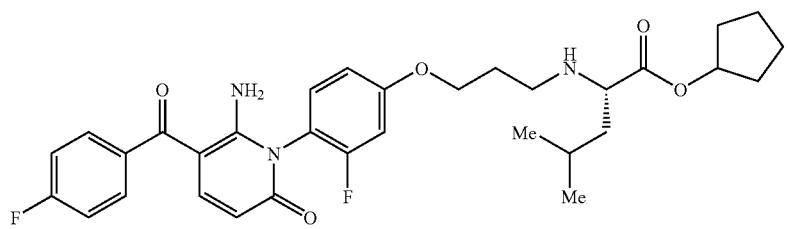

Example 68

Cyclopentyl N²-[3-(4-{6-amino-5-[(2,4-difluorophenyl)carbonyl]-2-oxopyridin-1(2H)-yl}-3,5-difluorophenoxy)propyl]-L-lysinate

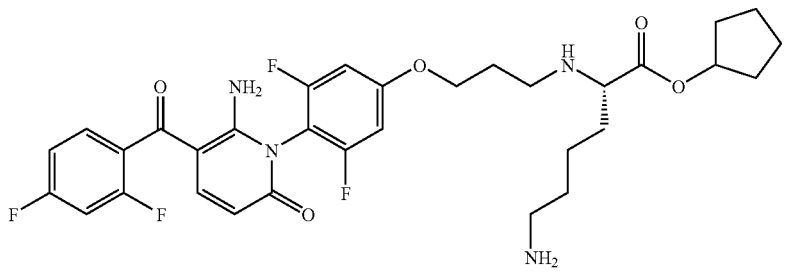

Example 68 was synthesised via a similar route to Example 52 using L-Lysine(Z)-cyclopentyl ester. LC/MS: m/z 633 [M+H]⁺. ¹H NMR (300 MHz, CD₃OD) δ: 7.45-7.54 (2H, m), 7.12 (2H, t, J=8.6 Hz), 6.93 (2H, d, J=9.8 Hz), 5.81 (1H, d, J=9.8 Hz), 5.33-5.40 (1H, m), 4.25 (2H, t, J=5.1 Hz), 4.10-4.16 (1H, m), 2.96 (2H, t), 2.27-2.35 (2H, m), 1.63-2.12 (16H, m).

Example 69 tert-Butyl N²-[3-(4-{6-amino-5-[(2,4-difluorophenyl)carbonyl]-2-oxopyridin-1(2H)-yl}-3,5-difluorophenoxy)propyl]-L-lysinate

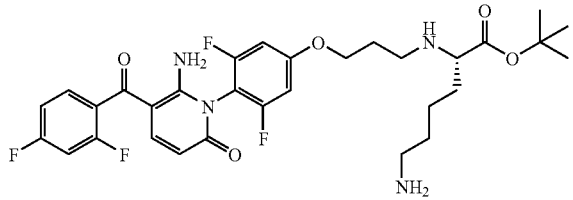

Example 69 was synthesised via a similar route to Example 52 using L-Lysine(Z)-t-butyl ester. LC/MS: m/z 621 [M+H]⁺. ¹H NMR (300 MHz, CD₃OD) δ: 7.48 (2H, dd, J=9.7, 2.7 Hz), 7.12 (2H, t, J=8.6 Hz), 6.88 (2H, d, J=9.2 Hz), 5.81 (1H, d, J=9.6 Hz), 4.18 (2H, t, J=6.2 Hz), 3.15 (H, t, J=6.6 Hz), 2.76-2.87 (3H, m), 2.68 (1H, dt, J=11.5, 6.9 Hz), 1.97-2.05 (4H, m), 1.64 (4H, dt, J=6.1 Hz), 1.01 (9H, s).

Example 70

Cyclopentyl N-[2-(3-{6-amino-5-[(4-fluorophenyl)carbonyl]-2-oxopyridin-1(2H)-yl}phenyl)ethyl]-L-leucinate

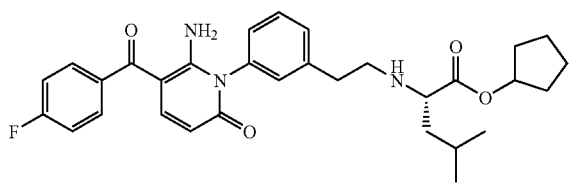

Example 70 was synthesised using similar methodology to Intermediate 4J (instead using 3-aminophenethyl alcohol) and L-Leucine cyclopentyl ester (Intermediate 8).
LC/MS: m/z 534 [M+H]⁺. ¹H NMR (300 MHz, DMSO-d₆) δ: 9.40-9.00 (2H, m), 7.65-7.44 (5H, m), 7.38-7.11 (4H, m), 5.72 (1H, d, J=9.9 Hz), 5.30-5.20 (1H, m), 4.10-4.00 (1H, m), 3.45-3.15 (2H, m), 3.10-3.00 (2H, m), 1.95-1.80 (2H, m), 1.75-1.55 (9H, m), 9.93 (6H, d, J=4.8 Hz).

Example 71

Cyclopentyl(S)-2-[3,5-Difluoro-4-[3-(4-fluorobenzoyl)-6-oxo-1,6-dihydro pyridin-2-ylamino]benzylamino]-3-phenylpropionate

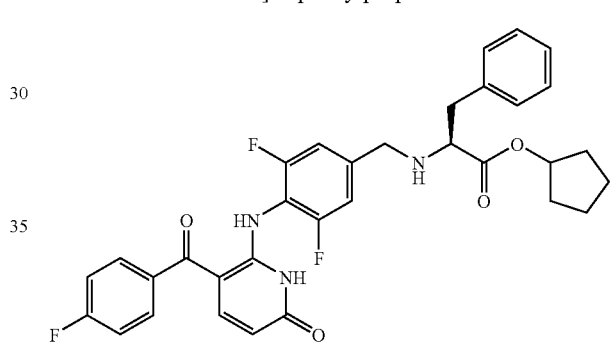

A solution of Intermediate 7 (20 mg) in 20% TFA/DCM (0.5 ml) was allowed to stand at RT for 1 h. Upon completion the reaction mixture was evaporated to dryness by blowing under a gentle flow of N₂. DCM (0.5 ml) was added and was blown under N₂. Drying under N₂ was continued overnight. Yield=20 mg, 98%.
LCMS purity 96%, m/z 590 [M+H]⁺, ¹H NMR (400 MHz, d₆-DMSO), δ: 0.75-1.33 (8H, m), 2.90 (1H, m), 3.50 (2H, m), 4.25 (3H, m), 4.93 (1H, m), 5.70, (1H, m), 5.98 (1H, m), 7.15-7.62 (11H, m), 9.7 (1H, br s), 10.42 (0.5H br s)

Example 72

(S)-{4-[6-Amino-5-(2,4-difluorobenzoyl)-2-oxo-2H-pyridin-1-yl]benzylamino}phenylacetic acid

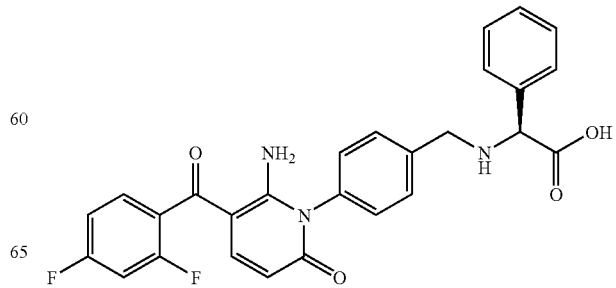

To a solution of Example 7 (100 mg, 0.179 mmol) in THF (1 ml) and MeOH (0.5 ml) was added 2M NaOH (aq, 1 ml). The mixture was allowed to stir at RT for 3 h, evaporated to near dryness, acidified using dropwise addition of 1M HCl and extracted with EtOAc (5 ml). EtOAc layer was concentrated in vacuo to give the crude acid. LCMS shows 80% product m/z=490 [M+H]$^+$ and 20% impurity m/z 470 [M+H]$^+$. Purification by preparative HPLC afforded the desired product. Yield=34 mg, 31%). LCMS purity 100%, m/z 490 [M+H]$^+$, $^1$H NMR (400 MHz, DMSO), δ: 3.64 (2H, m, CH$_2$), 4.06 (1H, s, CH), 5.50 (1H, d, Ar), 6.75 (1H, br s, NH), 6.96 (13H, m, Ar), 9.84 (1H, br s, NH).

The following compounds were prepared in a similar manner:

Example 73

(S)-2-{4-[6-Amino-5-(2,4-difluorobenzoyl)-2-oxo-2H-pyridin-1-yl]benzylamino}-3-phenylpropionic acid

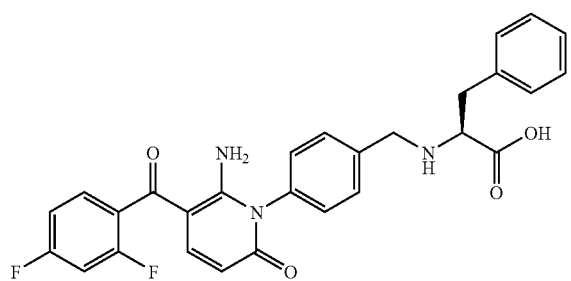

From Example 8. LCMS purity 99%, m/z 504 [M+H]$^+$, $^1$H NMR (400 MHz, DMSO), δ: 2.96-3.09 (3H, m), 3.81 (1H, d), 3.98 (1H, d), 5.76 (1H, d), 7.00 (1H, br s), 7.22-7.40 (9H, m), 7.41-7.61 (4H, m), 10.11 (1H, brs).

Example 74

(S)-2-{4-[6-Amino-5-(2,4-difluorobenzoyl)-2-oxo-2H-pyridin-1-yl]benzylamino}-4-methylpentanoic acid

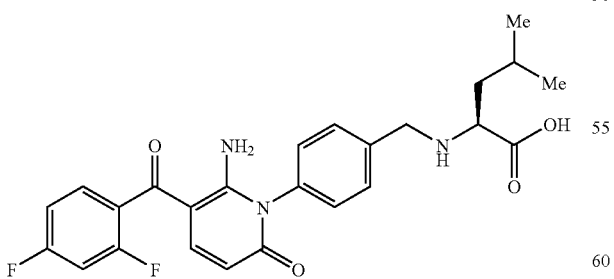

From Example 9. LCMS purity 91%, m/z 470 [M+H]$^+$, $^1$H NMR (400 MHz, DMSO), δ: 0.71 (6H, m), 1.40 (2H, m), 1.60 (1H, m), 3.44 (1H, m), 3.89 (2H, s), 5.49 (1H, d), 6.70 (1H, br s), 6.94-7.08 (2H, m), 7.14-7.33 (4H, m), 7.46 (2H, m), 9.86 (1H, br s).

Example 75

(S)-{4-[6-Amino-5-(4-fluorobenzoyl)-2-oxo-2H-pyridin-1-yl]benzylamino}phenylacetic acid

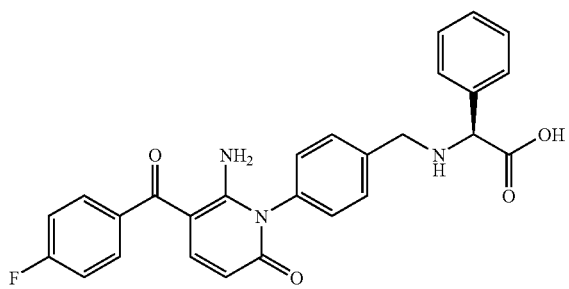

From Example 1. LCMS purity 100%, m/z 472 [M+H]$^+$, $^1$H NMR (400 MHz, DMSO), δ: 4.13 (1H, d), 4.22 (1H, d), 5.18 (1H, s), 5.73 (1H, d), 7.30-7.61 (13H, m), 7.73 (1H, d), 10.09 (2H, br s).

Example 76

(S)-{4-[6-Amino-5-(3-methyl-4-fluoro benzoyl)-2-oxo-2H-pyridin-1-yl]benzylamino}phenylacetic acid

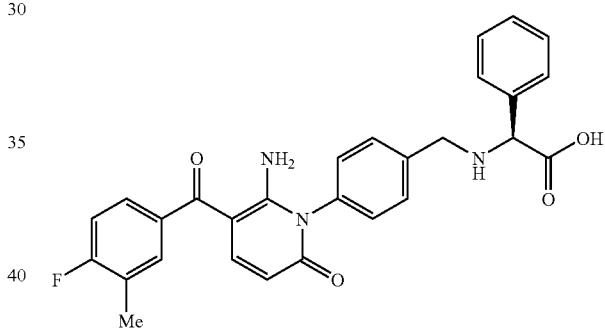

From Example 4. LCMS purity 86%, m/z 486 [M+H]$^+$, $^1$H NMR (400 MHz, DMSO), δ: 2.20 (3H, s), 3.98 (1H, d), 4.06 (1H, d), 5.07 (1H, s), 5.62 (1H, d), 7.12-7.50 (12H, m), 7.61 (1H, d), 9.90 (2H, br s).

Example 77

(S)-2-{4-[6-Amino-5-(2,4-difluorobenzoyl)-2-oxo-2H-pyridin-1-yl]benzylamino}-4-methylpentanoic acid

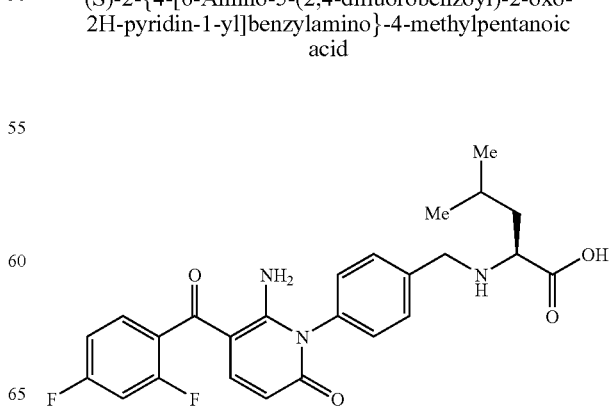

From Example 9. LCMS purity 91%, m/z 470 [M+H]+, 1H NMR (400 MHz, DMSO), δ: 0.71 (6H, m), 1.40 (2H, m), 1.60 (1H, m), 3.44 (1H, m), 3.89 (2H, s), 5.49 (1H, d), 6.70 (1H, br s), 6.94-7.08 (2H, m), 7.14-7.33 (4H, m), 7.46 (2H, m), 9.86 (1H, br s).

Example 78

(S)-2-{4-[6-Amino-5-(4-fluorobenzoyl)-2-oxo-2H-pyridin-1-yl]benzylamino}-3-phenylpropionic acid

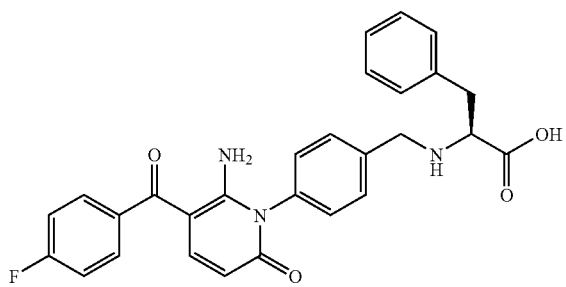

From Example 2. LCMS purity 100%, m/z 486 [M+H]+, 1H NMR (400 MHz, DMSO), δ: 3.00 (2H, m), 3.98 (3H, m), 5.65 (1H, d), 7.15-7.34 (11H, m), 7.40 (1H, d), 7.51 (2H, m).

Example 79

(S)-2-{4-[6-Amino-5-(4-fluorobenzoyl)-2-oxo-2H-pyridin-1-yl]benzylamino}-4-methylpentanoic acid

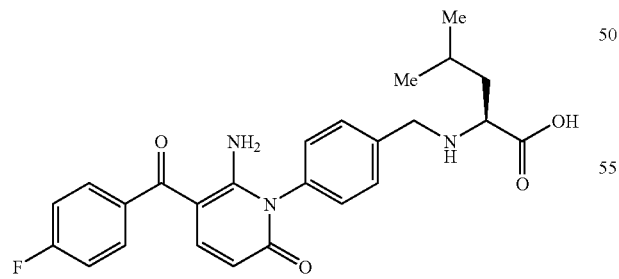

From Example 3. LCMS purity 100%, m/z 452 [M+H]+, 1H NMR (400 MHz, DMSO), δ: 0.81 (6H, m), 1.51 (2H, m), 1.72 (1H, m), 3.95 (2H, m), 5.61 (1H, d), 7.21-7.30 (4H, m), 7.39 (1H, d), 7.48 (2H, m), 7.52 (2H, m).

Example 80

(S)-2-{4-[6-Amino-5-(3-methyl-4-fluorobenzoyl)-2-oxo-2H-pyridin-1-yl]benzylamino}-3-phenylpropionic acid

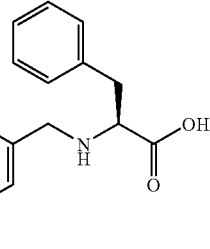

From Example 5. LCMS purity 100%, m/z 500 [M+H]+, 1H NMR (400 MHz, DMSO), δ: 2.33 (3H, s), 2.90-3.07 (3H, m), 3.76 (1H, d), 3.92 (1H, d), 5.72 (1H, d), 7.20-7.42 (9H, m), 7.49 (4H, m).

Example 81

(S)-2-{4-[6-Amino-5-(3-Methyl-4-fluorobenzoyl)-2-oxo-2H-pyridin-1-yl]benzylamino}-4-methylpentanoic acid

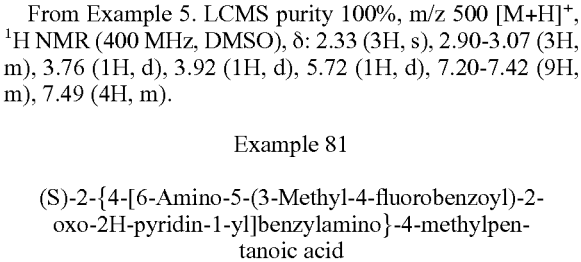

From Example 6. LCMS purity 98%, m/z 500 [M+H]+.

Example 82

Cyclopentyl(S)-2-(3-{4-[6-Amino-5-(4-fluorobenzoyl)-2-oxo-2H-pyridin-1-yl]phenoxy}propylamino)-3-phenylpropionic acid

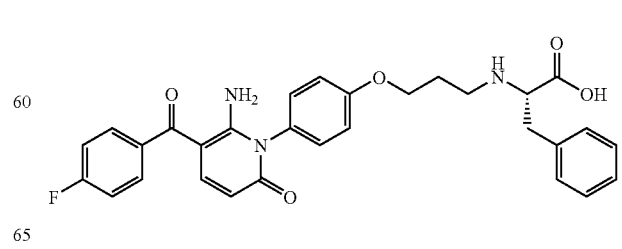

From Example 24. LCMS purity 93%, m/z 530 [M+H]+, 1H NMR (400 MHz, d6-DMSO), δ: 1.90 (2H, m), 2.80-2.90

(2H, m), 3.00 (2H, m), 3.40 (1H, m), 4.05 (2H, m), 5.70 (1H, d), 7.10 (1H, d), 7.20 (2H, d). 7.30 (5H, m), 7.35 (1H, d), 7.45 (1H, d), 7.60 (1H, d).

Example 83

(S)-2-(3-{4-[6-Amino-5-(3-methyl-4-fluoro benzoyl)-2-oxo-2H-pyridin-1-yl]phenoxy}propylamino)-3-phenyl propionic acid

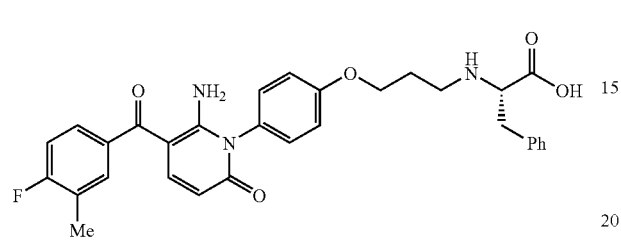

From Example 12. LCMS purity 96%, m/z 544 [M+H]$^+$, $^1$H NMR (400 MHz, d$_6$-DMSO), δ: 2.30 (2H, m), 2.40 (3H, s), 3.30 (1H, m), 4.30 (2H, m), 4.45 (1H, m), 5.85 (1H, d), 5.40 (1H, m), 5.85 (1H, d), 7.25 (2H, d), 7.40-7.55 (9H, m), 7.60-7.70 (2H, m).

Example 84

(S)-(3-{4-[6-Amino-5-(2,4-difluoro benzoyl)-2-oxo-2H-pyridin-1-yl]-phenoxy}propylamino)phenyl acetic acid

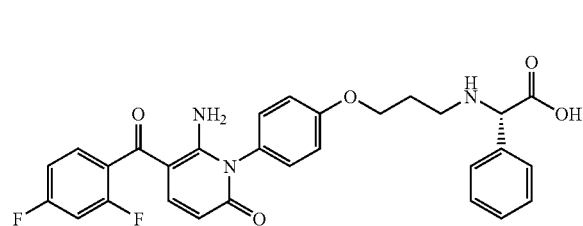

From Example 28. LCMS purity 82%, m/z 534 [M+H]$^+$, $^1$H NMR (400 MHz, CD$_3$OD), δ: 2.25 (2H, m), 3.10 (1H, m), 3.25 (1H, m), 4.20 (1H, m), 5.83 (1H, d), 7.15-7.60 (13H, d).

Example 85

(S)-2-(3-{4-[6-Amino-5-(4-fluorobenzoyl)-2-oxo-2H-pyridin-1-yl]phenoxy}propylamino)-4-methylpentanoic acid

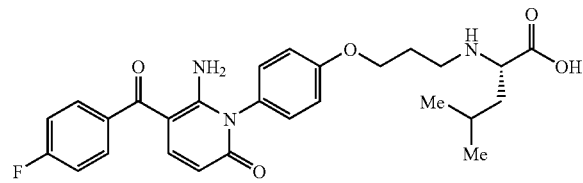

From Example 25. LCMS purity 100%, m/z 496 [M+H]$^+$, $^1$H NMR (400 MHz, d$_6$-DMSO), δ: 1.00 (6H, m), 1.75-1.90 (3H, m), 2.30 (2H, m), 3.10-3.30 (2H, m), 4.00 (1H, m), 4.25 (2H, m), 5.85 (1H, d), 5.40 (1H, m), 5.85 (1H, d), 7.20 (2H, d), 7.30 (2H, d), 7.40 (2H, t), 7.55 (1H, m), 7.65 (2H, m).

Example 86

(S)-2-(3-{4-[6-Amino-5-(2,4-difluoro benzoyl)-2-oxo-2H-pyridin-1-yl]phenoxy}propylamino)-3-phenyl propionic acid

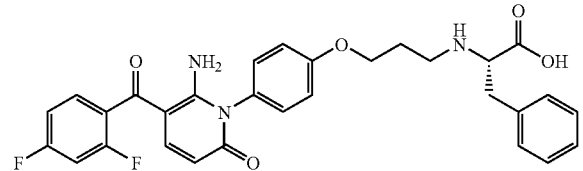

From Example 29. LCMS purity 100%, m/z 548 [M+H]$^+$, $^1$H NMR (400 MHz, d$_6$-DMSO), δ: 2.15 (2H, m), 3.15-3.30 (3H, m), 3.35 (1H, m), 4.10 (2H, m), 4.20 (1H, m), 5.65 (1H., d), 7.15 (2H, d), 7.20-7.35 (11H, m)

Example 87

(S)-(3-{4-[6-Amino-5-(4-fluoro-3-methylbenzoyl)-2-oxo-2H-pyridin-1-yl-phenoxy}propylamino)phenylacetic acid

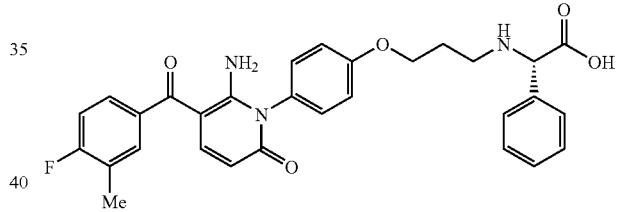

From Example 26. LCMS purity 95%, m/z 530 [M+H]$^+$, $^1$H NMR (400 MHz, d$_6$-DMSO), δ: 2.15 (3H, s) –2.35 (2H, m), 2.85 (2H, m), 3.05 (2H, m), 4.10 (2H, m), 5.25 (1H, m), 5.70 (1H, d), 4.25 (2H, m), 5.85 (1H, d), 5.40 (1H, m), 5.85 (1H, d), 7.10 (2H, d), 7.25 (2H, d), 7.3 (1H, d), 7.35 (1H, m), 7.40-7.55 (5H, m), 7.60 (2H, m).

Example 88

(S)-2-(3-{4-[6-Amino-5-(4-fluoro-3-methyl benzoyl)-2-oxo-2H-pyridin-1-yl]phenoxy}propylamino)-4-methylpentanoic acid

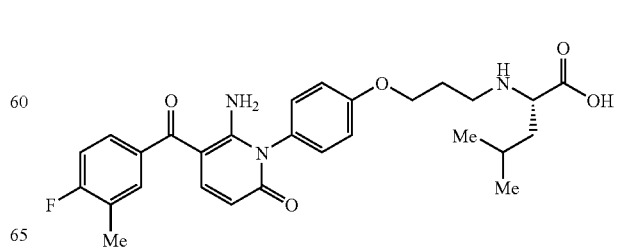

From Example 27. LCMS purity 94%, m/z 510 [M+H]$^+$, $^1$H NMR (400 MHz, d$_6$-DMSO), δ: 0.90 (6H, br s), 1.65-1.80 (3H, m), 2.1-2.30 (3H, s+2H, m), 3.0-3.20 (2H, m), 3.90 (1H, m), 4.15 (2H, m), 5.65 (1H, d), 7.15 (2H, d), 7.20-7.30 (3H, m), 7.30 (1H, m), 7.40 (1H, d), 7.45 (2H, s).

Example 89

S)-(3-{4-[6-Amino-5-(4-fluorobenzoyl)-2-oxo-2H-pyridin-1-yl]-3,5-difluorophenoxy}propylamino) phenylacetic acid

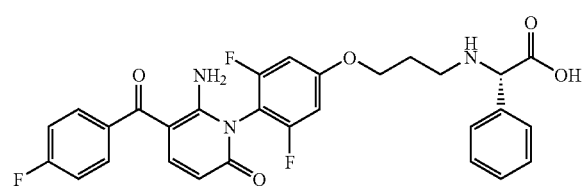

From Example 13. LCMS purity 91%, m/z 552 [M+H]$^+$, $^1$H NMR (400 MHz, d$_6$-DMSO), δ: 2.10-2.25 (2H, br m), 2.80 (1H, m), 3.00 (1H, m), 4.15 (2H, d), 5.20 (1H, s), 5.70 (1H, d), 5.65 (1H, d), 6.95 (2H, d), 7.30 (2H, t), 7.30 (1H, m), 7.40-7.60 (8H, m).

Example 90

(S)-(3-{4-[6-Amino-5-(4-fluorobenzoyl)-2-oxo-2H-pyridin-1-yl]-3,5-difluorophenoxy}propylamino) phenylacetic acid

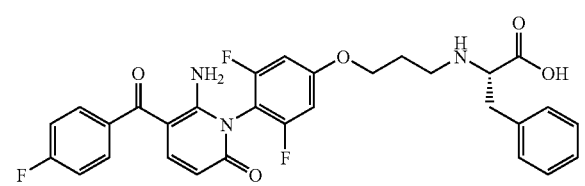

From Example 14. LCMS purity 98%, m/z 566 [M+H]$^+$, $^1$H NMR (400 MHz, d$_6$-DMSO), δ: 2.35 (2H, m), 3.1-3.3 (3H, m), 3.50 (1H, m), 4.25-4.40 (3H, m), 5.80 (1H, d), 5.70 (1H, d), 7.10 (2H, d), 7.30-7.45 (7H, m), 7.60-7.70 (3H, m).

Example 91

(S)-2-(3-{4-[6-Amino-5-(4-fluorobenzoyl)-2-oxo-2H-pyridin-1-yl]-3,5-difluorophenoxyphenoxy}propylamino)-4-methyl pentanoic acid

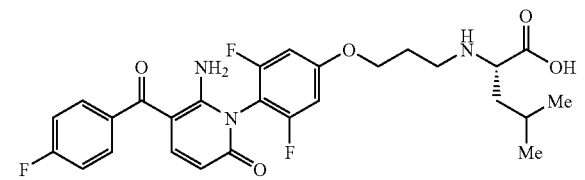

From Example 15. LCMS purity 92%, m/z 532 [M+H]$^+$, $^1$H NMR (400 MHz, d$_6$-DMSO), δ: 0.95 (6H, m), 1.8 (3H, m), 2.30 (2H, m), 3.10-3.25 (2H, m), 3.95 (1H, m), 4.25 (2H, m), 5.80 (1H, d), 7.10 (2H, m), 7.40 (2H, m), 7.60 (1H, m), 7.65 (2H, m).

Example 92

(S)-2-{4-[6-Amino-5-(2,4-fluorobenzoyl)-2-oxo-2H-pyridin-1-yl]-3,5-difluorobenzylamino}-3-phenyl-propionic acid

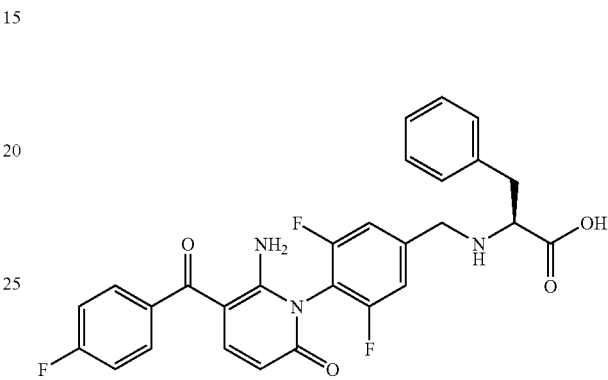

From Example 10. LCMS purity 95%, m/z 522 [M+H]$^+$, $^1$H NMR (400 MHz, CD$_3$OD), δ: 3.30 (2H, m), 4.15 (1H, m), 4.25 (2H, m), 5.75 (1H, d), 7.15-7.35 (9H, m), 5.20 (1H, m), 5.90 (1H, d), 7.35-7.50 (9H, m), 7.55 (2H, m), 7.65 (1H, d).

Example 93

(S)-2-(3-{4-[6-Amino-5-(4-fluoro-3-methylbenzoyl)-2-oxo-2H-pyridin-1-yl]-3,5-difluorophenoxy}propylamino)-3-phenylpropionic acid

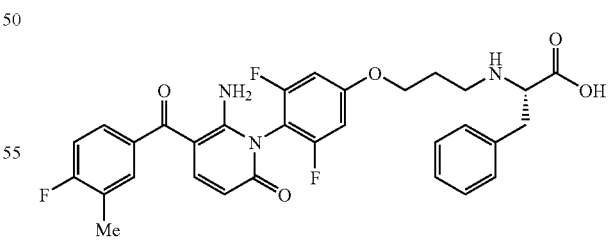

From Example 18. LCMS purity 92%, m/z 580 [M+H]$^+$, $^1$H NMR (400 MHz, d$_6$-DMSO), δ: 2.30 (2H, m), 2.40 (3H, s), 3.15-3.35 (4H, m), 3.50 (1H, m), 4.30 (2H, m), 4.35 (1H, m), 5.80 (1H, d), 7.10 (2H, m), 7.35-7.50 (7H, m), 7.55 (1H, m), 7.65 (1H, m).

Example 94

(S)-(3-{4-[6-Amino-5-(4-fluorobenzoyl)-2-oxo-2H-pyridin-1-yl]-Phenoxy}propylamino)phenylacetic acid

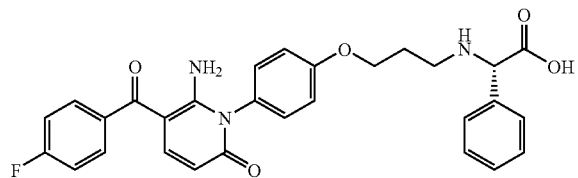

From Example 23. LCMS purity 87%, m/z 516 [M+H]+, $^1$H NMR (400 MHz, d$_6$-DMSO), δ: 2.25 (2H, m), 2.80 (1H, m), 3.10 (1H, m), 4.15 (2H, m), 5.30 (1H, s), 5.75 (2H, d), 7.15 (2H, d), 7.25 (2H, d), 7.40 (2H, t), 7.50-7.70 (7H, m).

Example 95

(S)-(3-{4-[6-Amino-5-(2,4-difluoro benzoyl)-2-oxo-2H-pyridin-1-yl]-3,5-difluorophenoxy}propylamino)phenyl acetic acid

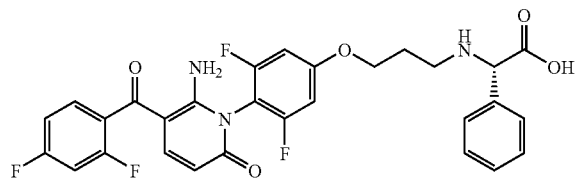

From Example 20. LCMS purity 84%, m/z 570 [M+H]+, $^1$H NMR (400 MHz, d$_6$-DMSO), δ: 2.30 (2H, m), 2.90 (1H, m), 3.15 (1H, m), 4.23 (2H, m), 5.32 (1H, s), 5.85 (1H, d), 7.10 (2H, d), 7.50 (3H, m), 7.60-7.65 (6H, m).

Example 96

(S)-2-(3-{4-[6-Amino-5-(2,4-difluoro benzoyl)-2-oxo-2H-pyridin-1-yl]phenoxy}propylamino)-4-methyl pentanoic acid

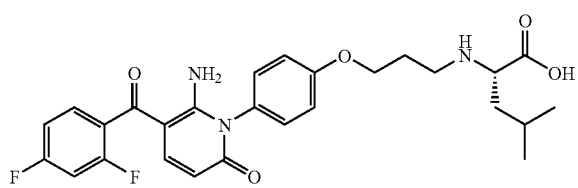

From Example 30. LCMS purity 93%, m/z 514 [M+H]+, $^1$H NMR (400 MHz, d$_6$-DMSO), δ: 0.95 (6H, m), 1.85 (3H, m), 2.30 (2H, m), 3.15-3.22 (2H, m), 3.99 (1H, m), 4.21 (2H, m), 5.77 (1H, d), 7.20 (2H, d), 7.30 (4H, m), 7.45 (1H, m), 7.55 (1H, m).

Example 97

(S)-2-(3-{4-[6-Amino-5-(2,4-difluoro benzoyl)-2-oxo-2H-pyridin-1-yl]-3,5-difluorophenoxy}propylamino)-4-methyl pentanoic acid

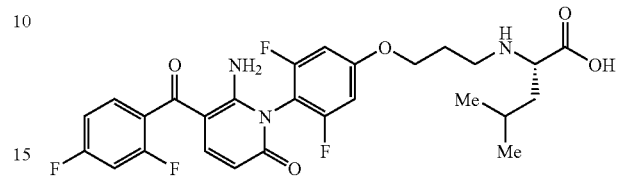

From Example 22. LCMS purity 88%, m/z 550 [M+H]+, $^1$H NMR (400 MHz, d$_6$-DMSO), δ: 0.80-0.95 (6H, m), 1.50-1.85 (3H, m), 1.95-2.10 (2H, m), 2.95-3.05 (2H, m), 3.75-3.85 (1H, m), 4.05-4.15 (2H, m), 5.65 (1H, d), 7.00 (1H, d), 7.10-7.20 (1H, m), 7.25-7.30 (1H, m), 7.30-7.40 (1H, m), 7.45-7.55 (1H, m), 7.80-8.25 (1H, br s), 9.90-10.20 (1H, br s).

Example 98

(S)-2-(3-{4-[6-Amino-5-(4-fluoro-3-methylbenzoyl)-2-oxo-2H-pyridin-1-yl]-3,5-difluorophenoxy}propylamino)-4-methylpentanoic acid

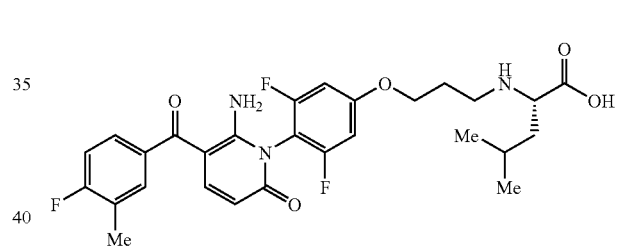

From Example 19. LCMS purity 93%, m/z 546 [M+H]+, $^1$H NMR (400 MHz, d$_6$-DMSO), δ: 0.95-1.05 (6H, m), 1.55-1.75 (2H, m), 1.80-1.90 (1H, m), 2.10-2.25 (2H, m), 2.35 (3H, s), 3.00-3.15 (2H, m), 3.70 (1H, m), 4.15-4.30 (2H, m), 5.80 (1H, d), 7.10 (1H, d), 7.25-7.35 (1H, m), 7.40-7.45 (1H, m), 7.50-7.55 (1H, m), 7.55-7.65 (1H, m), 8.90-10.70 (2H, br s).

Example 99

(S)-(3-{4-[6-Amino-5-(4-fluoro-3-methylbenzoyl)-2-oxo-2H-pyridin-1-yl]-3,5-difluorophenoxy}propylamino)phenylacetic acid

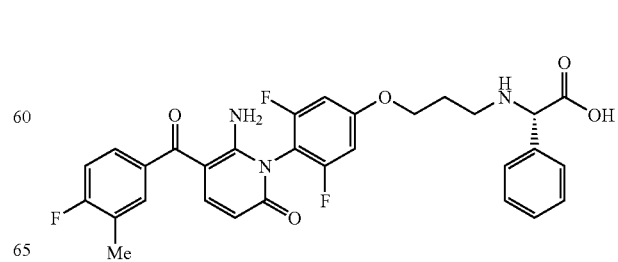

From Example 17. LCMS purity 100%, m/z 566 [M+H]$^+$, $^1$H NMR (400 MHz, d$_6$-DMSO), δ: 2.05-2.20 (2H, m), 2.30 (3H, s), 2.75-3.05 (2H, m), 4.05-4.20 (2H, m), 4.65-4.85 (1H, m), 5.70 (1H, d), 7.00 (1H, d), 7.25-7.35 (1H, m), 7.35-7.60 (8H, m).

Example 100

(S)-2-(3-{4-[6-Amino-5-(2,4-difluorobenzoyl)-2-oxo-2H-pyridin-1-yl]-3,5-difluorophenoxy}-propylamino)-3-phenyl propionic acid

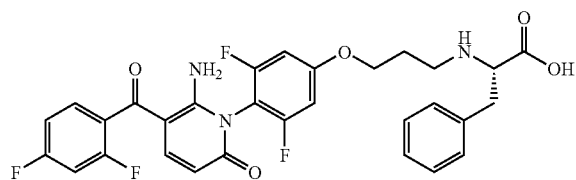

From Example 21. LCMS purity 100%, m/z 584 [M+H]$^+$, $^1$H NMR (400 MHz, DMSO), δ: 2.05-2.15 (2H, m), 3.00-3.10 (3H, m), 4.00-4.25 (4H, m), 5.75 (1H, d), 7.05 (1H, d), 7.25-7.50 (8H, m), 7.55-7.65 (1H, m).

Example 101

(S)-2-{4-[6-Amino-5-(4-fluorobenzoyl)-2-oxo-2H-pyridin-1-yl]-3,5-difluorobenzylamino}-4-methylpentanoic acid

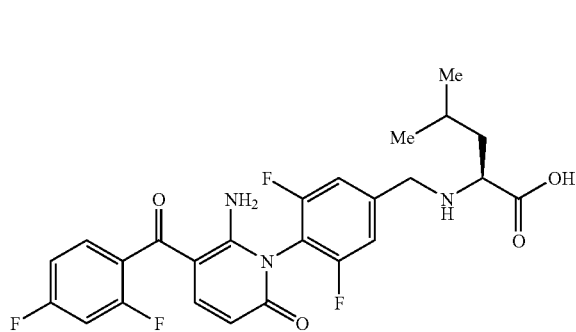

From Example 11. LCMS purity 92%, m/z 506 [M+H]$^+$, $^1$H NMR (400 MHz, MeOD), δ: 0.85-1.05 (6H, m), 1.65-1.85 (3H, m), 3.95-4.05 (1H, m), 4.25-4.35 (2H, m), 5.75 (1H, d), 6.90 (1H, d), 7.00-7.10 (2H, m), 7.35-7.45 (4H, m).

Example 102

(S)-2-(4-{4-[6-Amino-5-(4-fluorobenzoyl)-2-oxo-2H-pyridin-1-yl]-3,5-difluorophenoxy}cyclohexylamino)-4-methylpentanoic acid

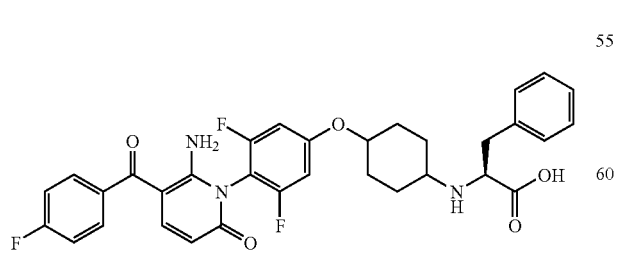

From Example 31. LCMS purity 91%, m/z 606 [M$^+$+H], $^1$H NMR (400 MHz, CD$_3$OD), δ: 1.55-2.55 (8H, m), 3.20-3.40 (2H, m), 4.25-4.35 (1H, m), 4.45-4.55 (1H, m), 4.85-4.95 (1H, m), 5.95 (1H, d), 6.95-7.10 (2H, m), 7.35-7.55 (6H, m), 7.70-7.80 (2H, m), 7.80-7.85 (1H, d).

Example 103

(2S)-[(4-{4-[6-amino-5-(4-fluorobenzoyl)-2-oxopyridin-1(2H)-yl]-3,5-difluorophenoxy}cyclohexyl)amino](phenyl)acetic acid

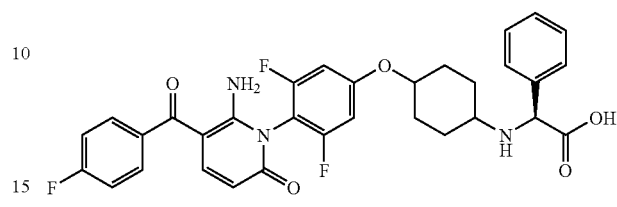

From Example 32. LCMS purity 89%, m/z 592 [M+H]$^+$, $^1$H NMR (400 MHz, CD$_3$OD), δ: 1.60-1.75 (2H, m), 1.80-1.95 (2H, m), 2.00-2.15 (2H, m), 2.15-2.30 (2H, m), 3.05-3.20 (1H, m), 4.65-4.75 (1H, m), 4.75-4.80 (1H, m), 5.80 (1H, d), 6.85-6.95 (2H, m), 7.20-7.30 (2H, m), 7.40-7.50 (3H, m), 7.55-7.65 (4H, m), 7.65-7.70 (1H, m).

Example 104

N-(4-{4-[6-amino-5-(4-fluorobenzoyl)-2-oxopyridin-1(2H)-yl]-3,5-difluorophenoxy}cyclohexyl)-L-leucine

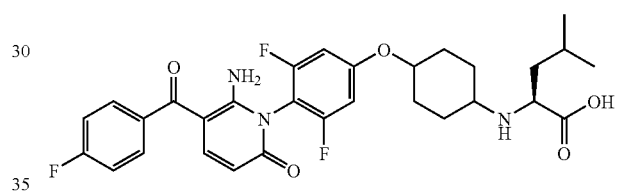

From Example 33. LCMS purity 93%, m/z 572 [M+H]$^+$, $^1$H NMR (400 MHz, CD$_3$OD), δ: 0.85-1.00 (6H, m), 1.45-2.00 (9H, m), 2.05-2.25 (3H, m), 3.05-3.15 (1H, m), 3.60-3.75 (1H, m), 4.30 and 4.65 (0.5H each, m), 5.70 (1H, d), 6.75-6.85 (2H, m), 7.10-7.15 (2H, m), 7.45-7.55 (2H, m), 7.55-7.65 (1H, m).

Example 105

(S)-2-{4-[6-Amino-5-(4-fluorobenzoyl)-2-oxo-2H-pyridin-1-yl]cyclohexyl amino}-3-phenylpropionic acid

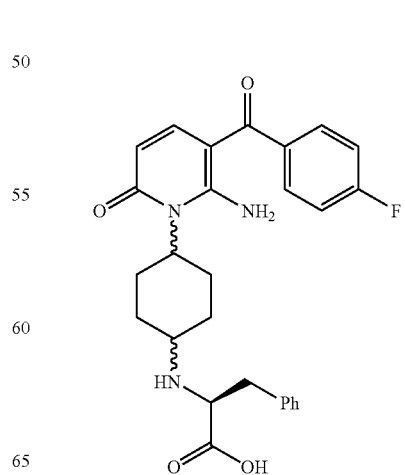

From Example 34. LCMS purity 98%, m/z 478 [M+H]$^+$, $^1$H NMR (400 MHz, CD$_3$OD), δ: 1.55-1.85 (4H, m), 1.95-2.20 (2H, m), 2.30-2.75 (2H, m), 3.15-3.20 (1H, m), 3.25-3.35 (2H, m), 4.05-4.15 (1H, m), 5.60 (1H, d), 7.05-7.15 (2H, m), 7.15-7.35 (5H, m), 7.35-7.45 (3H, m).

Example 106

(R)-(3-{4-[6-Amino-5-(2,4-difluoro benzoyl)-2-oxo-2H-pyridin-1-yl]-3,5-difluorophenoxy}propylamino) phenyl acetic acid

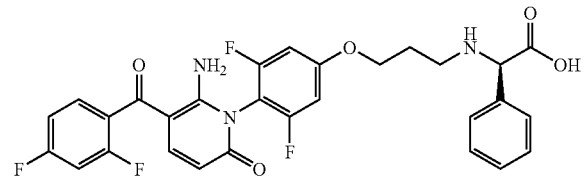

From Example 42. LCMS purity 88%, m/z 570 [M+H]$^+$, $^1$H NMR (400 MHz, DMSO), δ: 2.05-2.20 (2H, m), 2.75-2.95 (2H, m), 4.10-4.20 (2H, m), 4.30-4.50 (1H, m), 5.75 (1H, d), 7.00-7.10 (2H, m), 7.20-7.30 (1H, m), 7.35-7.50 (7H, m), 7.55-7.65 (1H, m).

Example 107

(2S)-[(3-{4-[6-amino-5-(2,4-difluorobenzoyl)-2-oxopyridin-1(2H)-yl]-3,5-difluorophenoxy}propyl) amino](cyclohexyl)acetic acid

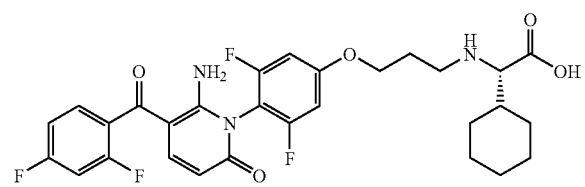

From Example 48, LCMS purity 95%, m/z 576 [M+H]$^+$, $^1$H NMR (300 MHz, DMSO), δ: 10.16 (1H, br s), 8.78 (1H, br s), 8.12 (1H, br s), 7.62-7.53 (1H, m), 7.47-7.32 (2H, m), 7.27-7.21 (1H, m), 7.07 (2H, d, J=10.2 Hz), 5.74 (1H, d, J=9.6 Hz), 4.19 (2H, t, J=5.7 Hz), 3.85-3.75 (1H, m), 3.15-3.00 (2H, m), 2.20-2.05 (2H, m), 1.95-1.60 (6H, m), 1.40-0.90 (5H, m).

Example 108

N-(3-{4-[6-amino-5-(2,4-difluorobenzoyl)-2-oxopyridin-1(2H)-yl]-3,5-difluorophenoxy}propyl)-D-leucine

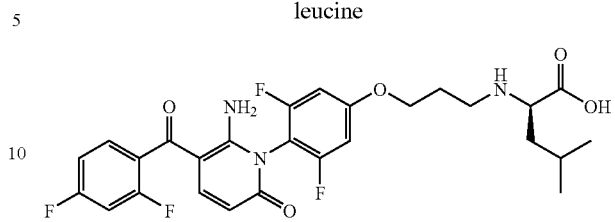

From Example 50. LCMS purity 90%, m/z 550 [M+H]$^+$, $^1$H NMR (300 MHz, DMSO), δ: 7.63-7.52 (1H, m), 7.46-7.32 (2H, m), 7.28-7.10 (1H, m), 7.06 (2H, d, J=10.2 Hz), 5.73 (1H, d, J=9.9 Hz), 4.25-4.15 (2H, m), 3.90-3.80 (1H, m), 3.20-3.00 (2H, m), 2.20-2.05 (2H, m), 1.80-1.55 (3H, m), 0.98-0.90 (6H, m).

Example 109

N-(5-{4-[6-amino-5-(4-fluorobenzoyl)-2-oxopyridin-1(2H)-yl]-3,5-difluorophenoxy}pentyl)-L-leucine

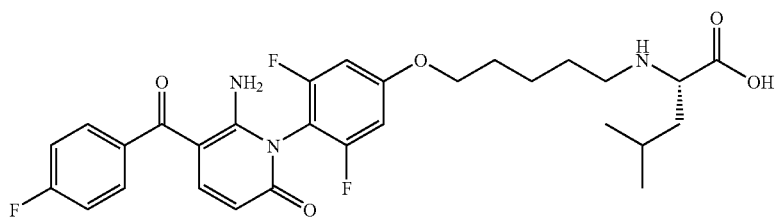

From Example 55. To a solution of cyclopentyl N-(5-{4-[6-amino-5-(4-fluorobenzoyl)-2-oxopyridin-1(2H)-yl]-3,5-difluorophenoxy}pentyl)-L-leucinate (33 mg, 0.05 mmol) in THF (1 ml) and water (1 ml) was added LiOH (25 mg, 1.05 mmol, 20 eq). The mixture was stirred at room temperature for 16 hours, before being heated at 80° C. for 10 hours. The mixture was concentrated under reduced pressure and water (5 ml) added. The pH was adjusted to 7 using 1M HCl and the aqueous layer extracted with 1-butanol (3×5 ml). The combined organic extracts were concentrated under reduced pressure. The solid residue was triturated with Et$_2$O, collected by filtration and purified by preparative HPLC to provide the title compound as a white solid as the mono-TFA salt (7 mg, 24% yield). LC/MS: m/z 560 [M+H]$^+$. $^1$H NMR (300 MHz, DMSO-d$_6$) δ: 7.62-7.51 (3H, m), 7.34 (2H, m), 7.05 (2H, m), 5.72 (1H, d, J=9.8 Hz), 4.09 (2H, t, J=5.7 Hz), 3.23 (1H, m), 2.80 (2H, m), 1.79-1.43 (9H, m), 0.89 (6H, t, J=6.7 Hz).

Example 110

N-({4-[6-Amino-5-(4-fluorobenzoyl)-2-oxopyridin-1(2H)-yl]phenoxy}-acetyl)-L-leucine

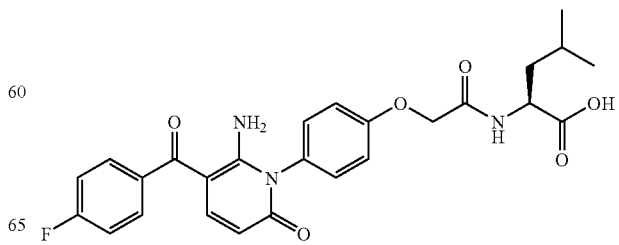

From Example 56. To a solution of cyclopentyl N-({4-[6-amino-5-(4-fluorobenzoyl)-2-oxopyridin-1(2H)-yl]phenoxy}acetyl)-L-leucinate (35 mg, 0.06 mmol) in THF (1 ml) and water (1 ml) was added LiOH (30 mg, 1.24 mmol, 20 eq). The mixture was stirred at room temperature for 16 hours, concentrated under reduced pressure and water (5 ml) added. The pH was adjusted to 7 using 1M HCl and the aqueous layer extracted with 1-butanol (3×5 ml). The combined organic extracts were concentrated under reduced pressure. The solid residue was triturated with Et$_2$O, filtered and dried under reduced pressure to provide the title compound as a cream solid (11 mg, 36% yield).

LC/MS: m/z 496 [M+H]$^+$. $^1$H NMR (300 MHz, DMSO-d$_6$) δ: 7.58-7.53 (3H, m), 7.43 (1H, d, J=9.6 Hz), 7.36-6.98 (6H, m), 5.68 (1H, d, J=9.6 Hz), 4.58 (2H, s), 3.90 (1H, m), 1.67-1.31 (3H, m), 0.86 (6H, m).

Example 111

N-[2-(4-{6-amino-5-[(4-fluorophenyl)carbonyl]-2-oxopyridin-1(2H)-yl}phenyl)ethyl]-L-leucine

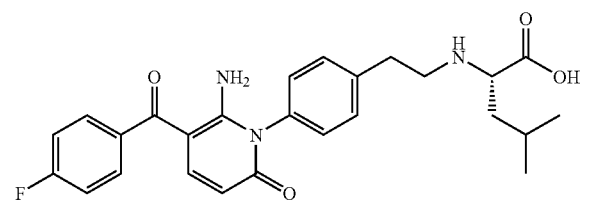

From Example 58. LC/MS: m/z 466 [M+H]$^+$. $^1$H NMR (300 MHz, DMSO-d$_6$) δ: 8.21 (1H, br s), 7.60-7.44 (4H, m), 7.39-7.30 (4H, m), 5.76-5.69 (1H, m), 4.00-3.85 (1H, m), 3.10-2.95 (2H, m), 1.85-1.60 (3H, m), 1.30-1.10 (2H, m), 0.95 (6H, d, J=6 Hz).

Example 112

N-[2-(4-{6-amino-5-[(4-methylphenyl)carbonyl]-2-oxopyridin-1(2H)-yl}phenyl)ethyl]-L-leucine

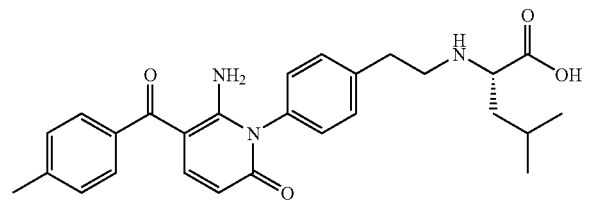

From Example 63. LC/MS: m/z 462 [M+H]$^+$. $^1$H NMR (300 MHz, CD$_3$OD) δ: 7.69 (1H, d, J=9.6 Hz), 7.53 (2H, d, J=7.2 Hz), 7.45 (2H, d, J=8.1 Hz), 7.34 (2H, d, J=7.8 Hz), 7.25 (2H, d, J=8.4 Hz), 5.80 (1H, d, J=9.6 Hz), 3.15 (1H, m), 3.02-2.75 (4H, m), 2.45 (3H, s), 1.73 (1H, m), 1.56-1.22 (2H, m), 0.96 (6H, dd).

Example 113

N-[2-(4-{6-amino-5-[(4-methoxyphenyl)carbonyl]-2-oxopyridin-1(2H)-yl}phenyl)ethyl]-L-leucine

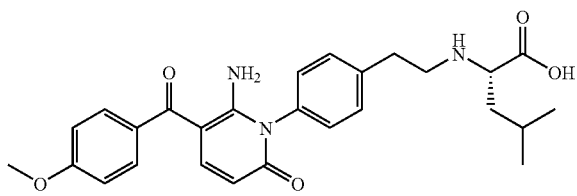

From Example 64. LC/MS: m/z 478 [M+H]$^+$. $^1$H NMR (300 MHz, DMSO-d$_6$) δ: 7.28 (2H, d, J=8.7 Hz), 7.15 (2H, d, J=8.1 Hz), 7.04 (1H, d, J=9.3 Hz), 6.89 (4H, m), 4.87 (1H, d, J=9.3 Hz), 3.78 (1H, m), 3.41 (3H, s), 2.75 (2H, m), 1.78 (1H, m), 1.24 (2H, m), 0.86 (6H, t).

Example 114

N-[2-(4-{6-amino-5-[(4-chlorophenyl)carbonyl]-2-oxopyridin-1(2H)-yl}phenyl)ethyl]-L-leucine

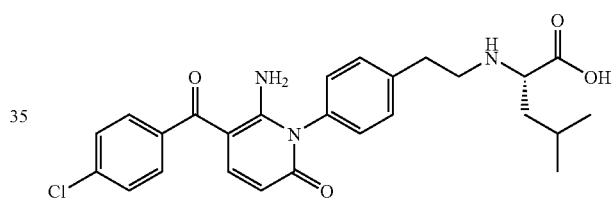

From Example 65. LC/MS: m/z 482 [M+H]$^+$. $^1$H NMR (300 MHz, CD$_3$OD) δ: 7.16 (1H, d), 7.52 (6H, m), 7.23 (2H, d), 6.82 (1H, d), 3.15 (1H, t), 1.74 (1H, m), 1.44 (2H, m), 0.93 (6H, dd).

Example 115

(2S)-4-amino-2-[(3-{4-[6-amino-5-(2,4-difluorobenzoyl)-2-oxopyridin-1(2H)-yl]-3,5-difluorophenoxy}propyl)amino]butanoate

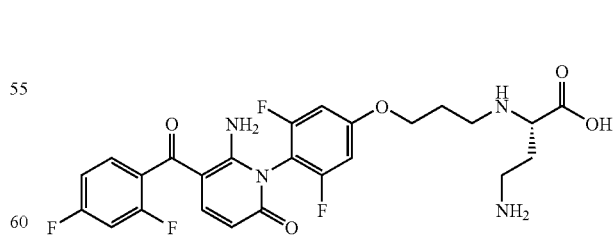

From Example 52. LC/MS: m/z 537 [M+H]$^+$. $^1$H NMR (300 MHz, DMSO-d$_6$) δ: 7.52-7.75 (2H, m), 7.30-7.48 (2H, m), 7.20-7.29 (1H, m), 7.09 (2H, d, J=9.7 Hz), 4.23 (1H, t, J=6.1 Hz), 4.07-4.17 (2H, m), 2.14-2.32 (2H, m), 1.22-1.41 (6H, m), 0.88 (4H, t, J=7.3 Hz)

Example 116

N-(5-{4-[6-amino-5-(2,4-difluorobenzoyl)-2-oxopyridin-1(2H)-yl]-3,5-difluorophenoxy}pentyl)-L-leucine

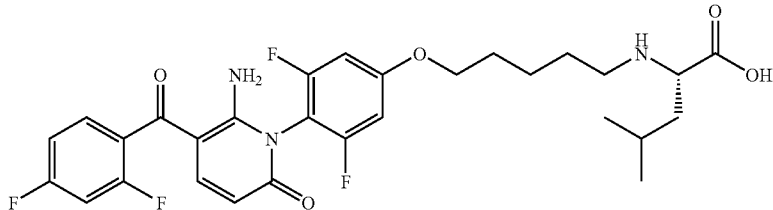

From Example 54. To a solution of tert-butyl N-(5-{4-[6-amino-5-(2,4-difluorobenzoyl)-2-oxopyridin-1(2H)-yl]-3,5-difluorophenoxy}pentyl)-L-leucinate (21 mg, 0.04 mmol) in DCM (2.5 ml) was added TFA (2.5 ml). The mixture was stirred at room temperature for 20 hours, before concentrating under reduced pressure. The residue was dissolved in minimal MeOH and azeotroped with 1:1 toluene/DCM three times. The title compound was afforded as a cream coloured solid as the mono-TFA salt (21 mg, 92% yield).

LC/MS: m/z 634 [M+H]$^+$. $^1$H NMR (300 MHz, DMSO-d$_6$) δ: 10.14 (1H, br s), 8.21 (1H, br s), 7.57 (1H, m), 7.46 (1H, m), 7.34 (1H, dd, J=9.6, 2.4 Hz), 7.21 (1H, m), 7.06 (2H, d, J=10.2 Hz), 5.73 (1H, d, J=9.9 Hz), 4.10 (2H, t, J=5.7 Hz), 3.40 (1H, m), 2.84 (2H, t, J=6.6 Hz), 1.79-1.48 (9H, m), 0.90 (6H, t, J=6.3 Hz).

The following examples were prepared in a similar manner:

Example 117

N-[2-(4-{6-amino-5-[(2,4-difluorophenyl)carbonyl]-2-oxopyridin-1(2H)-yl}phenyl)ethyl]-L-leucine

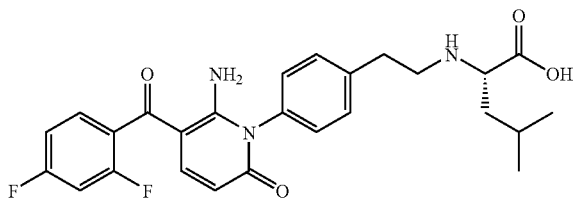

From Example 60. LC/MS: m/z 484 [M+H]$^+$. $^1$H NMR (300 MHz, DMSO-d$_6$) δ: 10.06 (1H, br s), 9.17 (2H, br s), 7.55-6.94 (8H, m), 5.72 (1H, d, J=9.6 Hz), 4.05-3.93 (1H, m), 3.40-3.10 (3H, m), 1.85-1.65 (4H, m), 0.95 (6H, d, J=5.7 Hz).

Example 118

(2S)-{[2-(4-{6-amino-5-[(4-fluorophenyl)carbonyl]-2-oxopyridin-1 (2H-yl}phenyl)ethyl]amino}(phenyl)ethanoic acid

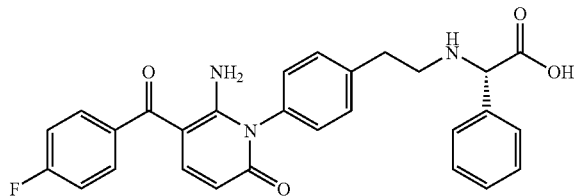

From Example 62. LC/MS: m/z 486 [M+H]$^+$. $^1$H NMR (300 MHz, DMSO-d$_6$) δ: 9.80 (2H, br s), 7.70-7.20 (14H, m), 5.70 (1H, d, J=9.6 Hz), 5.24 (1H, s), 3.20-2.90 (4H, m).

Measurement of Biological Activities p38 MAP Kinase Activity

The ability of compounds to inhibit p38 MAP a Kinase activity was measured in an assay performed by Upstate (Dundee UK). In a final reaction volume of 25 μL, p38 MAP Kinase a (5-10 mU) is incubated with 25 mM Tris pH 7.5, 0.002 mMEGTA, 0.33 mg/mL myelin basic protein, 10 mM MgAcetate and [g-33P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

Duplicate data points are generated from a ⅓ log dilution series of a stock solution in DMSO. Nine dilutions steps are made from a top concentration of 10 μM, and a 'no compound' blank is included. The standard radiometric filter-binding assay is performed at an ATP concentration at, or close to, the Km. Data from scintillation counts are collected and subjected to free-fit analysis by Prism software. From the curve generated, the concentration giving 50% inhibition is determined and reported.

LPS-Stimulation of THP-1 Cells

THP-1 cells were plated in 100 μl at a density of 4×10$^4$ cells/well in V-bottomed 96 well tissue culture treated plates and incubated at 37° C. in 5% CO$_2$ for 16 hrs. 2 hrs after the addition of the inhibitor in 1 OOP, of tissue culture media, the cells were stimulated with LPS (E. coli strain 005:B5, Sigma) at a final concentration of 1 μg/ml and incubated at 37° C. in 5% $CO_2$ for 6 hrs. TNF-α levels were measured from cell-free supernatants by sandwich ELISA (R&D Systems #QTA00B).

LPS-Stimulation of Human Whole Blood

Whole blood was taken by venous puncture using heparinised vacutainers (Becton Dickinson) and diluted in an equal volume of RPMI 1640 tissue culture media (Sigma). 100 μl was plated in V-bottomed 96 well tissue culture treated plates. 2 hrs after the addition of the inhibitor in 100 μl of RPMI 1640 media, the blood was stimulated with LPS (*E. coli* strain 005:B5, Sigma) at a final concentration of 100 ng/ml and incubated at 37° C. in 5% $CO_2$ for 6 hrs. TNF-α levels were measured from cell-free supernatants by sandwich ELISA (R&D Systems #QTA00B)

$IC_{50}$ values were allocated to one of three ranges as follows:

Range A: IC50<100 nM
Range B: 100 nM<IC50<1000 nM
Range C: IC50>1000 nM

Results Table

| Example | Inhibitor activity versus p38 MAPKa | Inhibitor activity versus THP-1 TNFα release | Inhibitor activity versus human whole blood TNFα release |
|---|---|---|---|
| 1 | B | C | NT |
| 2 | B | C | NT |
| 3 | B | C | C |
| 4 | B | C | NT |
| 5 | B | C | NT |
| 6 | B | C | NT |
| 7 | A | C | NT |
| 8 | A | B | NT |
| 9 | A | B | C |
| 10 | A | B | NT |
| 11 | A | B | C |
| 12 | A | B | NT |
| 13 | A | A | NT |
| 14 | A | A | NT |
| 15 | A | A | C |
| 16 | A | A | NT |
| 17 | A | A | NT |
| 18 | A | A | NT |
| 19 | A | A | C |
| 20 | A | A | B |
| 21 | A | A | C |
| 22 | A | A | B |
| 23 | A | B | NT |
| 24 | A | B | NT |
| 25 | A | B | C |
| 26 | A | B | NT |
| 27 | B | B | C |
| 28 | A | A | NT |
| 29 | A | B | NT |
| 30 | A | A | NT |
| 31 | A | A | NT |
| 32 | A | A | NT |
| 33 | A | A | NT |
| 34 | B | C | NT |
| 35 | B | C | NT |
| 36 | A | A | C |
| 37 | A | B | NT |
| 38 | A | A | C |
| 39 | A | B | NT |
| 40 | A | A | NT |
| 41 | B | A | C |
| 42 | A | A | B |
| 43 | A | A | NT |
| 44 | B | A | NT |
| 45 | A | A | NT |
| 46 | B | A | B |
| 47 | A | A | B |
| 48 | A | A | C |
| 49 | A | B | C |
| 50 | A | A | NT |
| 51 | A | A | NT |
| 52 | A | A | B |
| 53 | A | A | B |
| 54 | A | A | NT |
| 55 | B | A | NT |
| 56 | B | C | NT |
| 57 | B | A | B |
| 58 | B | A | B |
| 59 | B | A | B |
| 60 | B | A | NT |
| 61 | B | A | NT |
| 62 | B | B | NT |
| 63 | C | A | NT |
| 64 | C | B | NT |
| 65 | B | A | NT |
| 66 | B | B | NT |
| 67 | B | B | C |
| 68 | NT | NT | NT |
| 69 | NT | NT | NT |
| 70 | NT | NT | NT |
| 71 | A | C | NT |
| 72 | A | NT | NT |
| 73 | A | NT | NT |
| 74 | A | NT | NT |
| 75 | B | NT | NT |
| 76 | B | NT | NT |
| 77 | A | NT | NT |
| 78 | B | NT | NT |
| 79 | B | NT | NT |
| 80 | A | NT | NT |
| 81 | B | NT | NT |
| 82 | A | NT | NT |
| 83 | A | NT | NT |
| 84 | A | NT | NT |
| 85 | A | NT | NT |
| 86 | C | NT | NT |
| 87 | B | NT | NT |
| 88 | A | NT | NT |
| 89 | A | NT | NT |
| 90 | A | NT | NT |
| 91 | A | NT | NT |
| 92 | A | NT | NT |
| 93 | A | NT | NT |
| 94 | A | NT | NT |
| 95 | A | NT | NT |
| 96 | A | NT | NT |
| 97 | A | NT | NT |
| 98 | A | NT | NT |
| 99 | A | NT | NT |
| 100 | A | NT | NT |
| 101 | A | NT | NT |
| 102 | A | NT | NT |
| 103 | A | NT | NT |
| 104 | A | NT | NT |
| 105 | B | NT | NT |
| 106 | A | NT | NT |
| 107 | A | NT | NT |
| 108 | A | NT | NT |
| 109 | A | NT | NT |
| 110 | B | NT | NT |
| 111 | B | NT | NT |
| 112 | NT | NT | NT |
| 113 | NT | NT | NT |
| 114 | NT | NT | NT |
| 115 | NT | NT | NT |
| 116 | A | NT | NT |
| 117 | A | NT | NT |
| 118 | A | NT | NT |

Broken Cell Carboxylesterase Assay

Any given compound of the present invention wherein $R_1$ is an ester group may be tested to determine whether it meets the requirement that it be hydrolysed by intracellular esterases, by testing in the following assay.

Preparation of Cell Extract

U937 or Hut78 tumour cells (~$10^9$) were washed in 4 volumes of Dulbeccos PBS (~1 liter) and pelleted at 525 g for 10 min at 4-C. This was repeated twice and the final cell pellet was resuspended in 35 ml of cold homogenising buffer (Trizma 10 mM, NaCl 130 mM, $CaCl_2$ 0.5 mM pH 7.0 at 25° C.). Homogenates were prepared by nitrogen cavitation (700 psi for 50 min at 4° C.). The homogenate was kept on ice and supplemented with a cocktail of inhibitors at final concentrations of:

Leupeptin 1 µM
Aprotinin 0.1 µM
E64 8 µM
Pepstatin 1.5 µM
Bestatin 162 µM
Chymostatin 33 µM After clarification of the cell homogenate by centrifugation at 525 g for 10 min, the resulting supernatant was used as a source of esterase activity and was stored at −80° C. until required.

Measurement of Ester Cleavage

Hydrolysis of esters to the corresponding carboxylic acids can be measured using the cell extract, prepared as above. To this effect cell extract (~30 µg/total assay volume of 0.5 ml) was incubated at 37° C. in a Tris-HCl 25 mM, 125 mM NaCl buffer, pH 7.5 at 25° C. At zero time the ester (substrate) was then added at a final concentration of 2.5 µM and the samples were incubated at 37° C. for the appropriate time (usually 0 or 80 min). Reactions were stopped by the addition of 3× volumes of acetonitrile. For zero time samples the acetonitrile was added prior to the ester compound. After centrifugation at 12000 g for 5 min, samples were analysed for the ester and its corresponding carboxylic acid at room temperature by LCMS (Sciex API 3000, HP1100 binary pump, CTC PAL). Chromatography was based on an AceCN (75×2.1 mm) column and a mobile phase of 5-95% acetonitrile in water/0.1% formic acid.

Rates of hydrolysis are expressed in pg/mL/min.

Table 1 presents data showing that several amino acid ester motifs, conjugated to various intracellular enzyme inhibitors by several different linker chemistries are all hydrolysed by intracellular carboxyesterases to the corresponding acid.

TABLE 1

| Structure of amino acid ester conjugate | R | Linker | Hydrolysis Rate Range U937Cells (pg/ml/min) | Preparation of amino ester conjugate |
|---|---|---|---|---|
| 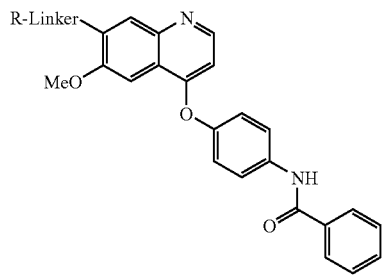 | 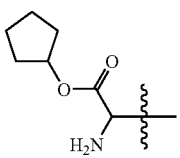 | —CH2CH2O— | 100-1000 | WO2006117552 |
| 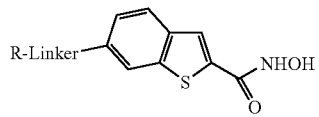 | 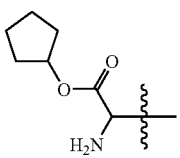 | —(CH$_2$)$_3$O—⌬—CH$_2$NHCH$_2$— | 1000-50000 | WO2006117548 |
| 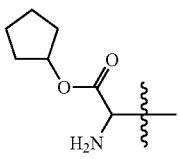 | 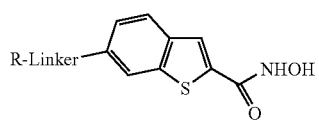 | —CH$_2$—⌬—CH$_2$NHCH$_2$— | >50000 | WO2006117549 |
| 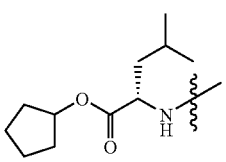 | 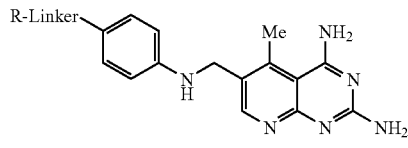 | —CH2CH2O— | >50000 | WO2006117567 |

| Structure of amino acid ester conjugate | R | Linker | Hydrolysis Rate Range U937Cells (pg/ml/min) | Preparation of amino ester conjugate |
|---|---|---|---|---|
| 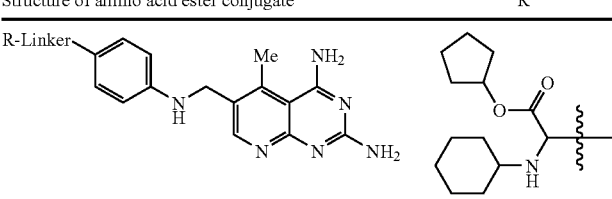 | 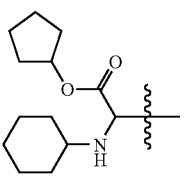 | —CH2CH2O— | 1000-50000 | WO2006117567 |
| 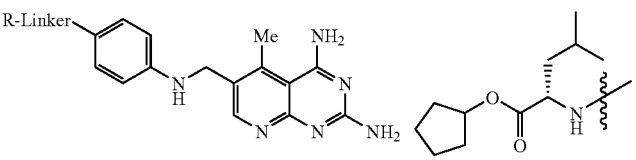 | 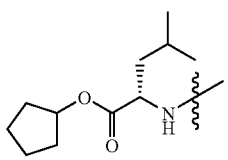 | —CH2— | 1000-50000 | WO2006117567 |
| 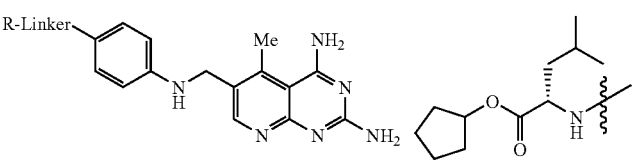 | 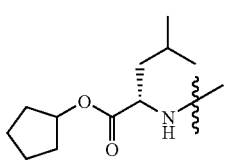 | —CO— | >50000 | WO2006117567 |
| 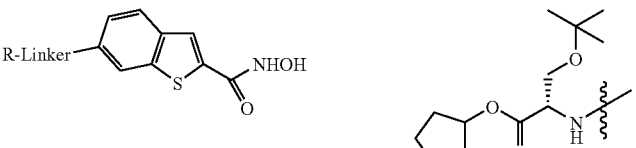 | 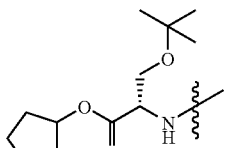 | —CH2—⟨phenyl⟩—CH2NHCH2— | >50000 | WO2006117549 |
| 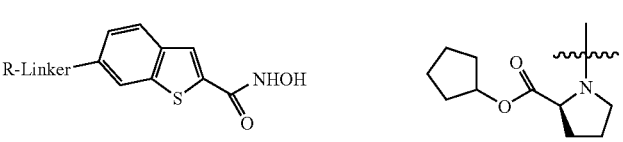 | 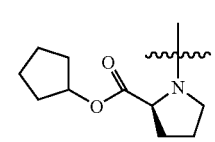 | —CH2—⟨phenyl⟩—CH2NHCH2— | >50000 | WO2006117549 |

The invention claimed is:

1. A compound of formula (I):

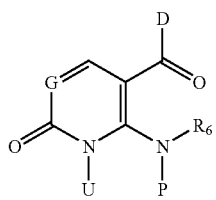

(I)

wherein:

G is —N= or —CH=

D is an optionally substituted mono- or bi-cyclic aryl or heteroaryl radical having 5-13 ring members;

$R_6$ is hydrogen or optionally substituted $C_1$-$C_3$ alkyl;

P represents hydrogen and U represents a radical of formula (IA); or U represents hydrogen and P represents a radical of formula (IA);

-A-(CH$_2$)$_z$—X$^1$-L$^1$-Y—NH—CHR$_1$R$_2$ (IA)

wherein

A represents an optionally substituted divalent mono- or bicyclic carbocyclic or heterocyclic radical having 5-13 ring members;

z is 0 or 1;

Y is a bond, —C(=O)—, —S(=O)$_2$—, —C(=O)NR$_3$—, —C(=S)—NR$_3$, —C(=NH)NR$_3$ or —S(=O)$_2$NR$_3$— wherein R$_3$ is hydrogen or optionally substituted $C_1$-$C_6$ alkyl;

L$^1$ is a divalent radical of formula -(Alk$^1$)$_m$(Q)$_n$(Alk$^2$)$_p$- wherein m, n and p are independently 0 or 1, Q is (i) an optionally substituted divalent mono- or bicyclic carbocyclic or heterocyclic radical having 5-13 ring members, or (ii), in the case where both m and p are 0, a divalent radical of formula —X$^2$-Q$^1$- or -Q$^1$-X$^2$— wherein X$^2$ is —O—, S— or NR$^4$— wherein R$^4$ is hydrogen or optionally substituted $C_1$-$C_3$ alkyl, and Q$^1$ is an optionally substituted divalent mono- or bicyclic carbocyclic or heterocyclic radical having 5-13 ring members, Alk$^1$ and Alk$^2$ independently represent optionally substituted divalent $C_3$-$C_7$ cycloalkyl radicals, or optionally substituted straight or branched, $C_1$-$C_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl; and X$^1$ represents a bond; —C(=O); or —S(=O)$_2$—; —NR$_4$C(=O)—, —C(=O)NR$_4$—, —NR$_4$C(=O)NR$_5$—, —NR$_4$S(=O)$_2$—, or —S(=O)$_2$NR$_4$— wherein R$_4$ and R$_5$ are independently hydrogen or optionally substituted C$_1$-C$_6$ alkyl;

R$_1$ is a carboxylic acid group (—COOH), or an ester group which is hydrolysable by one or more intracellular esterase enzymes to a carboxylic acid group; and R$_2$ is the side chain of a natural or non-natural alpha amino acid.

2. A compound as claimed in claim 1 wherein D is optionally substituted phenyl, or pyridinyl.

3. A compound as claimed in claim 1 wherein R$_6$ is hydrogen or methyl.

4. A compound as claimed in claim 1 wherein P is hydrogen and U is a radical of formula (IA) as defined in claim 1.

5. A compound as claimed in claim 1 wherein A is optionally substituted 1,4 phenylene or selected from those of

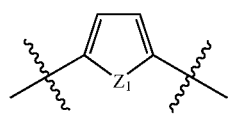

A

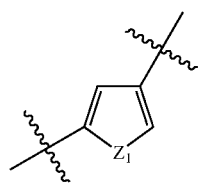

B

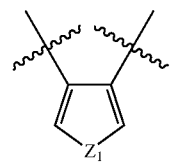

C

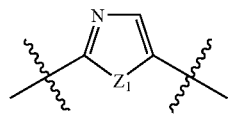

D

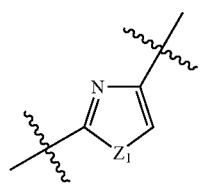

E

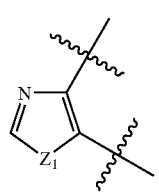

F

-continued

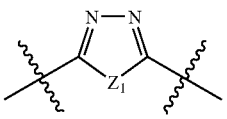

G

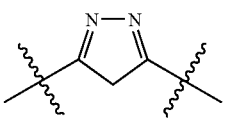

H

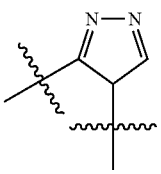

I

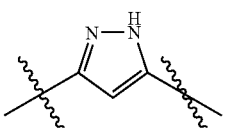

K

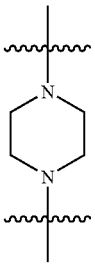

L

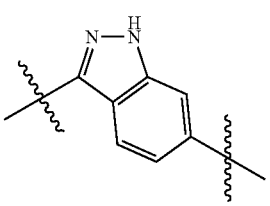

M

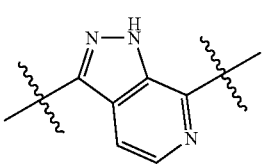

N

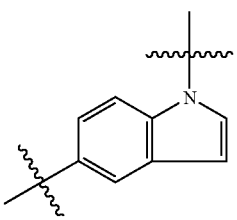

O

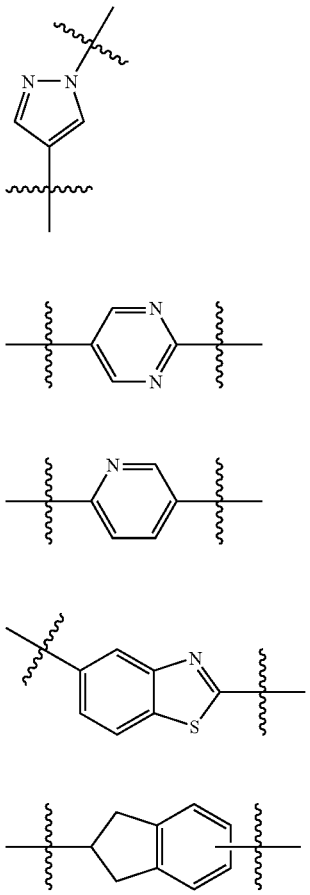

formulae A-X, optionally substituted:

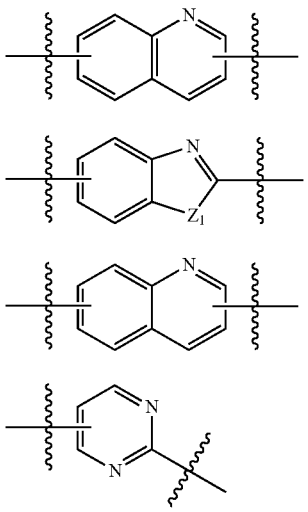

wherein $Z_1$ is NH, S or O.

6. A compound as claimed in claim 1 which has formula (IIA), (IIB) and (IIC):

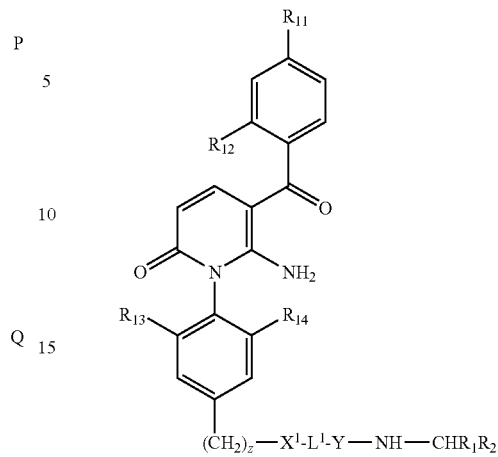
(IIA)

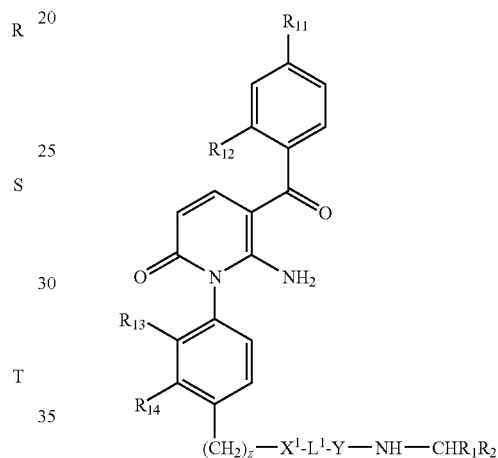
(IIB)

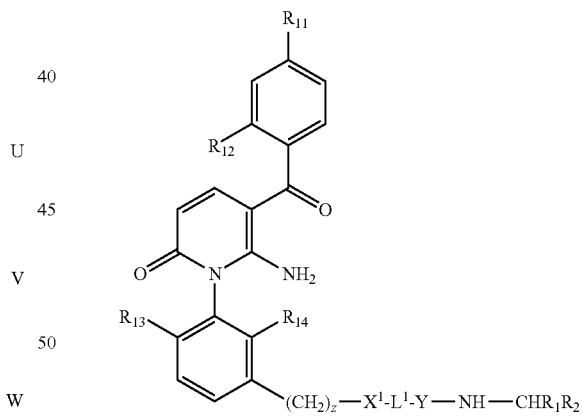
(IIC)

wherein
$R_{11}$=F, $R_{12}$=H, $R_{13}$=H and $R_{14}$=H; or
$R_{11}$=F, $R_{12}$=F, $R_{13}$=H and $R_{14}$=H; or
$R_{11}$=F, $R_{12}$=H, $R_{13}$=F and $R_{14}$=F; or
$R_{11}$=F, $R_{12}$=F, $R_{13}$=F and $R_{14}$=F; or
$R_{11}$=F, $R_{12}$=F, $R_{13}$=F and $R_{14}$=H
and wherein z, $X^1$, $L^1$, Y, $R^1$ and $R^2$ are as defined in claim 1.

7. A compound as claimed in claim 1 wherein z is 0.

8. A compound as claimed in claim 1 wherein Y is —C(═O), —S(═O)$_2$—, —C(═S)—NR$_3$, —C(═NH)—NR$_3$ or —S(═O)$_2$NR$_3$— wherein $R_3$ is hydrogen or $C_1$-$C_6$ alkyl.

9. A compound as claimed in claim 1 wherein Y is a bond.

10. A compound as claimed in claim 1 wherein, in the radical L$^1$, Alk$^1$ and Alk$^2$, when present, are selected from —CH$_2$—, —CH$_2$CH$_2$—, —CH$_2$CH$_2$CH$_2$—, and cyclopropylene, cyclopentylene, and cyclohexylene.

11. A compound as claimed in claim 1 wherein, in the radical L$^1$, m and p are 0.

12. A compound as claimed in claim 1 wherein, in the radical L$^1$, n and p are 0 and m is 1.

13. A compound as claimed in claim 1 wherein, in the radical L$^1$, m, n and p are all 0.

14. A compound as claimed in claim 1 wherein the radical —Y-L$^1$-X$^1$-[CH$_2$]$_z$— is selected from —C(=O)—, —C(=O)NH—, —(CH$_2$)$_v$—, —(CH$_2$)$_v$O—, —C(=O)—(CH$_2$)$_v$—, —C(=O)—(CH$_2$)$_v$O—, —C(=O)—NH—(CH$_2$)$_w$—, —C(=O)—NH—(CH$_2$)$_w$O—

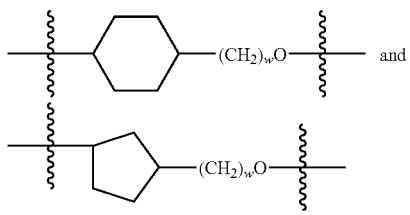

and wherein v is 1, 2, 3 or 4 and w is 1, 2 or 3.

15. A compound as claimed in claim 1 wherein the radical —Y-L$^1$-X$^1$-[CH$_2$]$_z$—, is —CH$_2$—, —CH$_2$CH$_2$—, —CH$_2$CH$_2$CH$_2$—, —CH$_2$CH$_2$CH$_2$CH$_2$—, —CH$_2$O—, —CH$_2$CH$_2$O—, —CH$_2$CH$_2$CH$_2$O—, —CH$_2$CH$_2$CH$_2$CH$_2$O—, —C(=O)—CH$_2$—, —C(=O)—CH$_2$O—, —C(=O)—NH—CH$_2$—, or —C(=O)—NH—CH$_2$O—.

16. A compound as claimed in claim 1 wherein R$_1$ is an ester group of formula —(C=O)OR$_{14}$ wherein R$_{14}$ is R$_8$R$_9$R$_{10}$C— wherein
    (i) R$_8$ is hydrogen or optionally substituted (C$_1$-C$_3$)alkyl-(Z$^1$)$_a$—[(C$_1$-C$_3$)alkyl]$_b$- or (C$_2$-C$_3$)alkenyl-(Z$^1$)$_a$-[(C$_1$-C$_3$)alkyl]$_b$— wherein a and b are independently 0 or 1 and Z$^1$ is —O—, —S—, or —NR$_{11}$— wherein R$_{11}$ is hydrogen or (C$_1$-C$_3$)alkyl; and R$_9$ and R$_{10}$ are independently hydrogen or (C$_1$-C$_3$)alkyl-;
    (ii) R$_8$ is hydrogen or optionally substituted R$_{12}$R$_{13}$N—(C$_1$-C$_3$)alkyl- wherein R$_{12}$ is hydrogen or (C$_1$-C$_3$)alkyl and R$_{13}$ is hydrogen or (C$_1$-C$_3$)alkyl; or R$_{12}$ and R$_{13}$ together with the nitrogen to which they are attached form an optionally substituted monocyclic heterocyclic ring of 5- or 6-ring atoms or bicyclic heterocyclic ring system of 8 to 10 ring atoms, and R$_9$ and R$_{10}$ are independently hydrogen or (C$_1$-C$_3$)alkyl-; or
    (iii) R$_8$ and R$_9$ taken together with the carbon to which they are attached form an optionally substituted monocyclic carbocyclic ring of from 3 to 7 ring atoms or bicyclic carbocyclic ring system of 8 to 10 ring atoms, and R$_{10}$ is hydrogen.

17. A compound as claimed in claim 16 wherein wherein R$_{14}$ is methyl, ethyl, n- or iso-propyl, n-, sec- or tert-butyl, cyclohexyl, allyl, phenyl, benzyl, 2-, 3- or 4-pyridylmethyl, N-methylpiperidin-4-yl, tetrahydrofuran-3-yl or methoxyethyl.

18. A compound as claimed in claim 16 wherein R$_{14}$ is cyclopentyl.

19. A compound as claimed in claim 1 wherein R$_2$ is hydrogen.

20. A compound as claimed in claim 1 wherein R$_2$ is phenylethyl, tert-butoxymethyl, cyclohexylmethyl, pyridin-3-ylmethyl, sec-butyl, tert-butyl, 1-benzylthio-1-methylethyl, 1-methylthio-1-methylethyl, or 1-mercapto-1-methylethyl.

21. A compound as claimed in claim 1 wherein R$_2$ is phenyl, benzyl, iso-butyl, cyclohexyl or t-butoxymethyl.

22. A compound as claimed in claim 1 wherein R$_1$ is an ester group of formula —(C=O)OR$_{14}$ wherein R$_{14}$ is cyclopentyl, and R$_2$ is phenyl, benzyl, iso-butyl, cyclohexyl or t-butoxymethyl.

23. A compound as claimed in claim 1 selected from the group consisting of
    Cyclopentyl (S)-(3-{4-[6-Amino-5-(2,4-difluoro benzoyl)-2-oxo-2H-pyridin-1-yl]-3,5-difluorophenoxy}propylamino)phenyl acetate;
    Cyclopentyl (S)-2-(3-{4-[6-Amino-5-(2,4-difluoro benzoyl)-2-oxo-2H-pyridin-1-yl]-3,5-difluorophenoxy}propylamino)-4-methyl pentanoate;
    Cyclopentyl (2R)-[(3-{4-[6-amino-5-(2,4-difluorobenzoyl)-2-oxopyridin-1(2H)-yl]-3,5-difluorophenoxy}propyl)amino](phenyl)acetate;
    2-Morpholin-4-ylethyl N-(3-{4-[6-amino-5-(2,4-difluorobenzoyl)-2-oxopyridin-1(2H)-yl]-3,5-difluorophenoxy}propyl)-L-leucinate;
    2 (Dimethylamino)ethyl N-(3-{-4-[6-amino-5-(2,4-difluorobenzoyl)-2-oxopyridin-1(2H)-yl]-3,5-difluorophenoxy}propyl)-L-leucinate;
    Cyclopentyl N-[2-(4-{6-amino-5-[(4-fluorophenyl)carbonyl]-2-oxopyridin-1(2H)-yl}phenyl)ethyl]-L-leucinate;
    Cyclopentyl N-(5-{4-[6-amino-5-(2,4-difluorobenzoyl)-2-oxopyridin-1(2H)-yl]-3,5-difluorophenoxy}pentyl)-L-leucinate;
    Cyclopentyl N-[3-(4-{6-amino-5-[(4-fluorophenyl)carbonyl]-2-oxopyridin-1(2H)-yl}phenyl)propyl]-L-leucinate;
    Cyclopentyl (2S)-4-amino-2-[(3-{4-[6-amino-5-(2,4-difluorobenzoyl)-2-oxopyridin-1(2H)-yl]-3,5-difluorophenoxy}propyl)amino]butanoate;
    Cyclopentyl N-(5-{4-[6-amino-5-(4-fluorobenzoyl)-2-oxopyridin-1(2H)-yl]-3,5-difluorophenoxy}pentyl)-L-leucinate;
    Cyclopentyl N-[2-(4-{6-amino-5-[(2,4-difluorophenyl)carbonyl]-2-oxopyridin-1(2H)-yl}phenyl)ethyl]-L-leucinate;
    tert-Butyl N-[2-(4-{6-amino-5-[(2,4-difluorophenyl)carbonyl]-2-oxopyridin-1(2H)-yl}phenyl)ethyl]-L-leucinate;
    Cyclopentyl (2S)-{[2-(4-{6-amino-5-[(4-fluorophenyl)carbonyl]-2-oxopyridin-1(2H)-yl}phenyl)ethyl]amino}(phenyl)ethanoate;
    Cyclopentyl N-[2-(4-{6-amino-5-[(4-methylphenyl)carbonyl]-2-oxopyridin-1(2H)-yl}phenyl)ethyl]-L-leucinate; and
    Cyclopentyl N-[2-(4-{6-amino-5-[(4-chlorophenyl)carbonyl]-2-oxopyridin-1(2H)-yl}phenyl)ethyl]-L-leucinate.

24. A compound as claimed in claim 1 which is in the form of a pharmaceutically acceptable salt.

25. A pharmaceutical composition comprising a compound as claimed in claim 1, together with a pharmaceutically acceptable carrier.

26. A method of inhibiting the activity of a p38 MAP kinase enzyme comprising contacting the enzyme with an amount of a compound as claimed in claim 1 effective for such inhibition.

27. A method for the treatment of autoimmune or inflammatory disease selected from Crohns disease, inflammatory bowel disease, ulcerative colitis, and rheumatoid arthritis, which comprises administering to a subject suffering from such disease an effective amount of a compound as claimed in claim 1.

28. The method as claimed in claim 27 wherein the disease is rheumatoid arthritis.

* * * * *